US012578320B2

(12) United States Patent
M'Saad

(10) Patent No.: US 12,578,320 B2
(45) Date of Patent: Mar. 17, 2026

(54) METHODS AND SYSTEMS FOR PHYSICAL EXPANSION AND IMAGING OF BIOLOGICAL SAMPLES

(71) Applicant: Yale University, New Haven, CT (US)

(72) Inventor: Ons M'Saad, New Haven, CT (US)

(73) Assignee: Yale University, New Haven, CT (US)

( * ) Notice: Subject to any disclaimer, the term of this patent is extended or adjusted under 35 U.S.C. 154(b) by 682 days.

(21) Appl. No.: 17/905,864

(22) PCT Filed: Mar. 12, 2021

(86) PCT No.: PCT/US2021/022212
§ 371 (c)(1),
(2) Date: Sep. 8, 2022

(87) PCT Pub. No.: WO2021/183956
PCT Pub. Date: Sep. 16, 2021

(65) Prior Publication Data
US 2023/0132184 A1     Apr. 27, 2023

Related U.S. Application Data

(60) Provisional application No. 62/989,158, filed on Mar. 13, 2020.

(51) Int. Cl.
*G01N 33/483* (2006.01)
*G01N 1/04* (2006.01)
*G01N 21/17* (2006.01)

(52) U.S. Cl.
CPC ........... *G01N 33/4833* (2013.01); *G01N 1/04* (2013.01); *G01N 21/17* (2013.01); *G01N 2021/1765* (2013.01)

(58) Field of Classification Search
CPC ...... G01N 33/4833; G01N 1/04; G01N 21/17; G01N 2021/1765; G01N 1/00; G01N 1/28; G01N 2001/282; G01N 1/30; G01N 2001/302; G01N 2001/305
See application file for complete search history.

(56) References Cited

U.S. PATENT DOCUMENTS

| | | |
|---|---|---|
| 10,309,879 B2 | 6/2019 | Chen et al. |
| 10,317,321 B2 | 6/2019 | Tillberg et al. |
| 2015/0144490 A1 | 5/2015 | Deisseroth et al. |
| 2016/0305856 A1 | 10/2016 | Boyden et al. |
| 2017/0089811 A1 | 3/2017 | Tillberg et al. |
| 2017/0219465 A1 | 8/2017 | Deisseroth et al. |
| 2019/0064037 A1 | 2/2019 | Boyden et al. |
| 2020/0271556 A1 | 8/2020 | Sarkar et al. |
| 2023/0132184 A1 | 4/2023 | M'Saad |

FOREIGN PATENT DOCUMENTS

| | | | | |
|---|---|---|---|---|
| WO | WO-2018157074 A1 * | 8/2018 | ....... | G01N 33/57415 |
| WO | 2019199579 A1 | 10/2019 | | |

OTHER PUBLICATIONS

Tillberg et al. 2019 (Expansion microscopy: scalable and convenient super-resolution microscopy; Annual Revies of Cell and Developmental Biology 35:683-701). (Year: 2019).*
Karagiannis et al. 2018 (Expansion microscopy: development and neuroscience applications; Current Opinion in Neurobiology 50: 56-63) (Year: 2018).*
International Search Report and Written Opinion, International Patent Application No. PCT/US2021/022212, Jul. 21, 2021.
Buffa, R., et al., "a-b,unsatureaed aldehyde of hyaluronan-synthesis, anlysis and applications", Carbohydrate Polymers, 134:293-299, 2015.
M'Saad, O., et al., "Light microscopy of proteins in their ultra-structural context", Nature Communications, 2020, vol. 11, No. 1, 3850, 15 pages.
Wiersma, J.A., et al, "High strength poly(meth)acrylamide copolymer hydrogels", Polymer Bulletin, 33: 615-622, 1994.

* cited by examiner

*Primary Examiner* — Mary Maille Lyons
(74) *Attorney, Agent, or Firm* — Saul Ewing LLP; Sean Ritchie; Kathryn Doyle

(57) ABSTRACT
Methods and systems for physical expansion and imaging of biological samples are described herein. In one aspect of the disclosure, a method for preparing a biological sample for the purpose of generating images of its ultrastructure with an imaging instrument includes a) physically expanding the sample by at least a factor of two in at least one dimension; and b) bulk labeling a plurality of components of the sample with at least one reagent to introduce contrast.

20 Claims, 68 Drawing Sheets

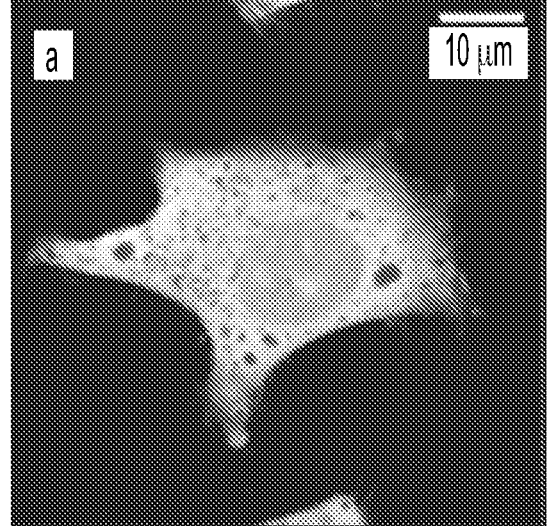
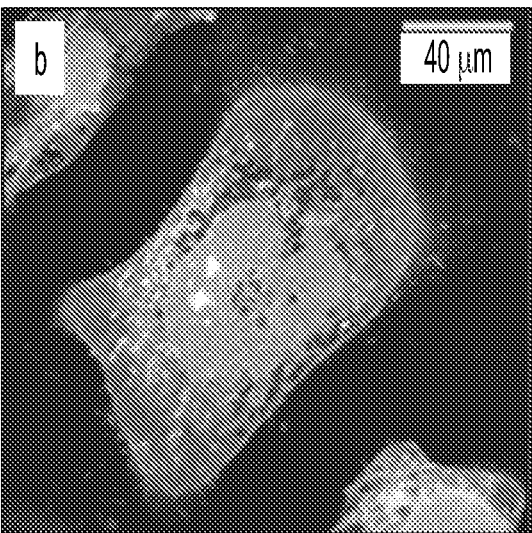
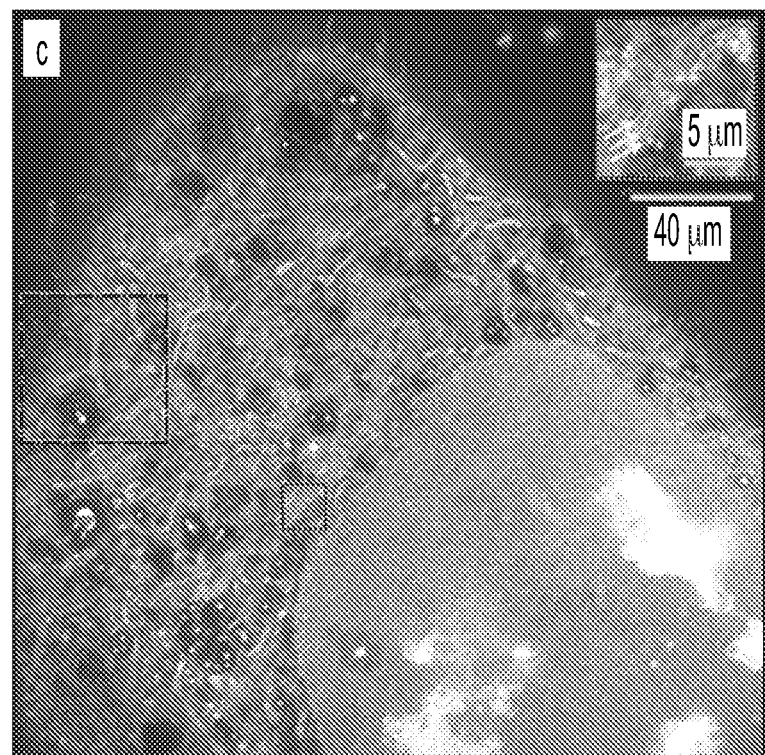
FIG. 1

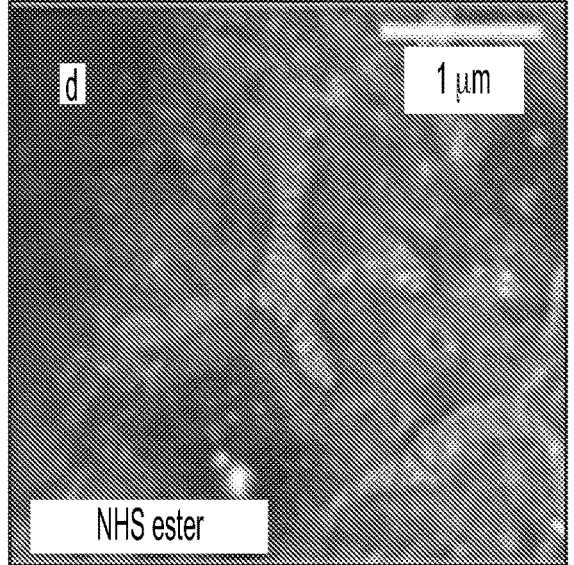
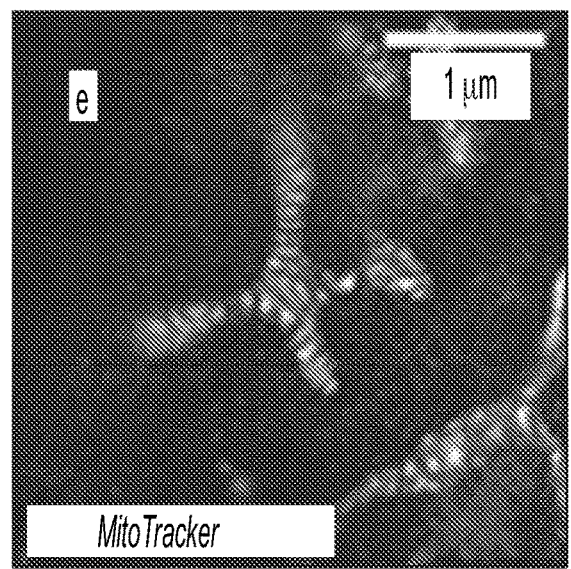
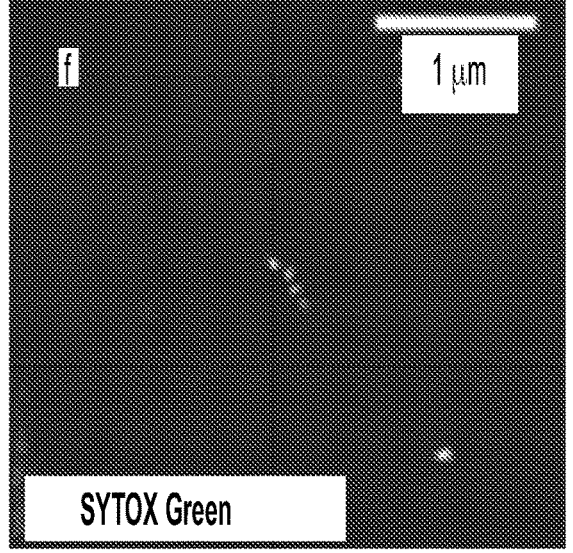
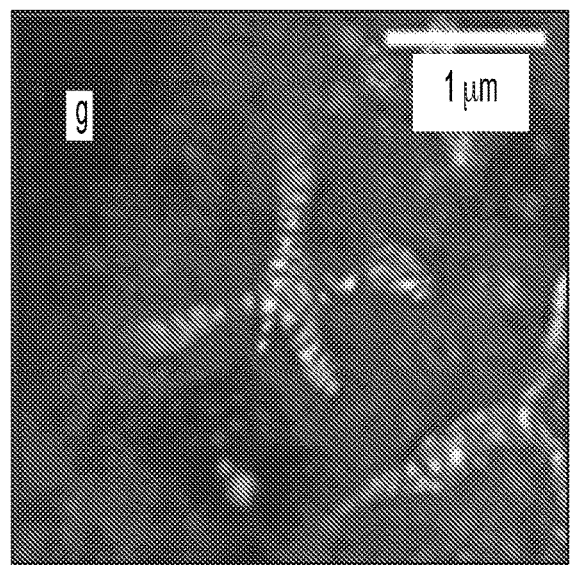
FIG. 1
CONTINUED

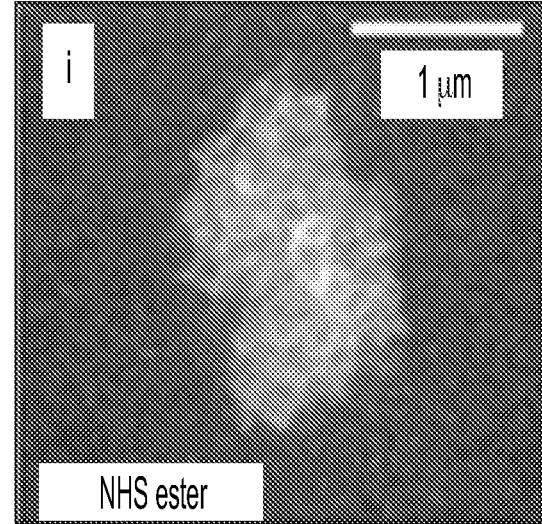
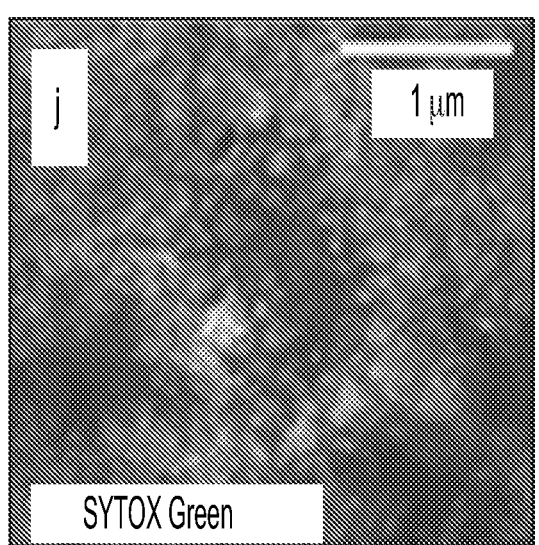
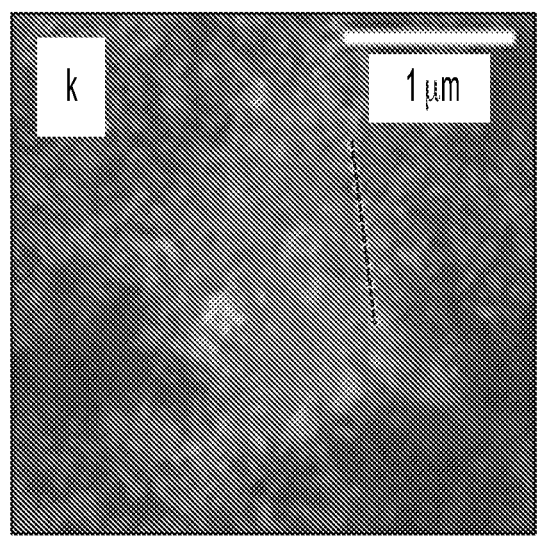
FIG. 1
CONTINUED

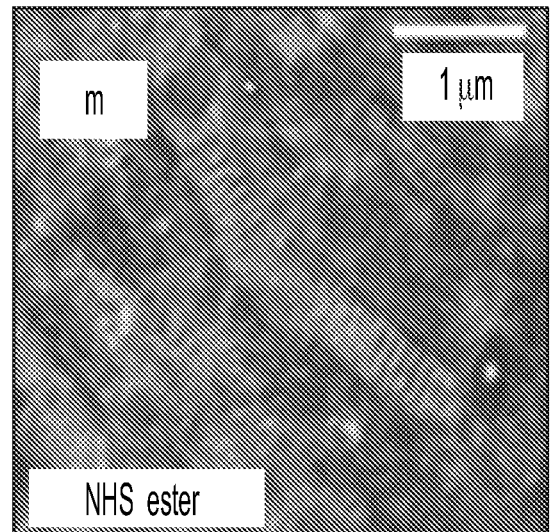
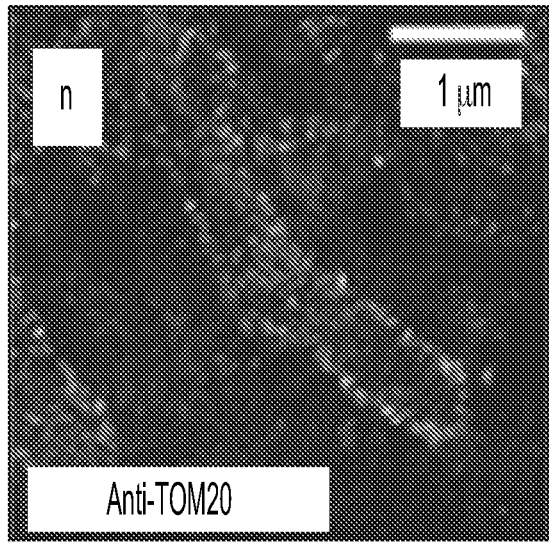
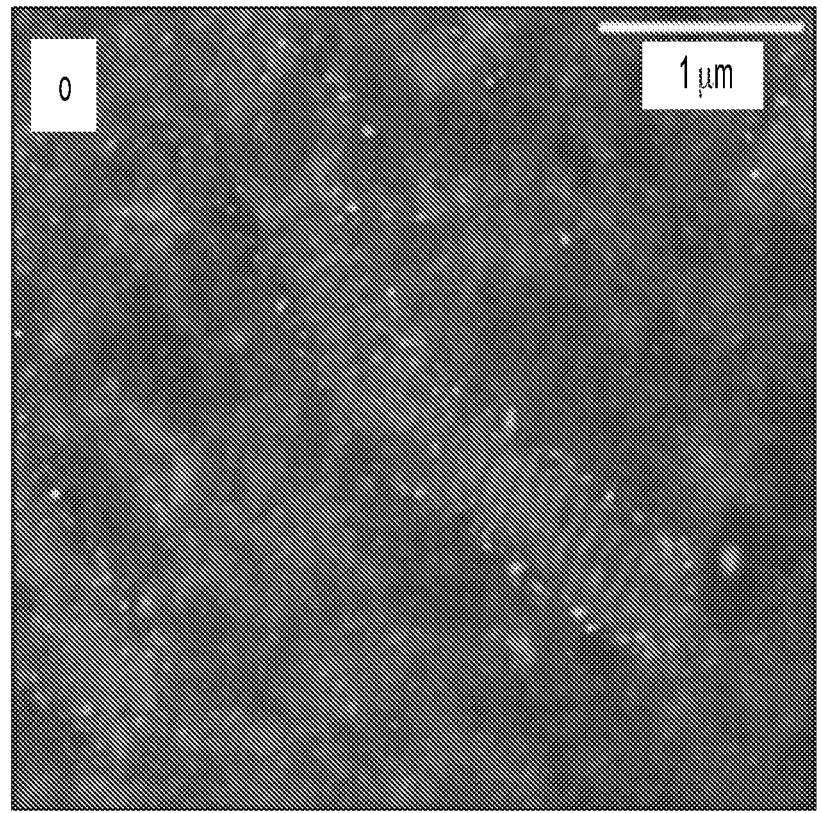
FIG. 1
CONTINUED

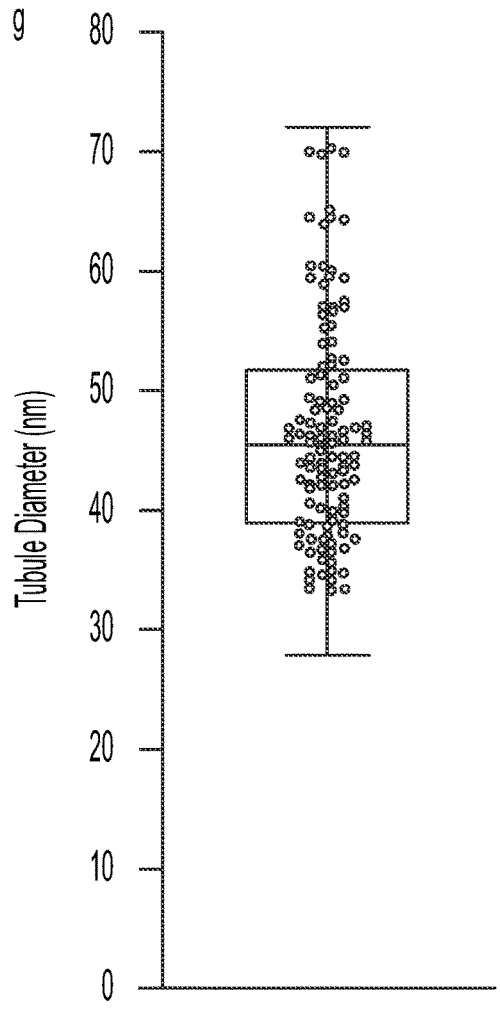
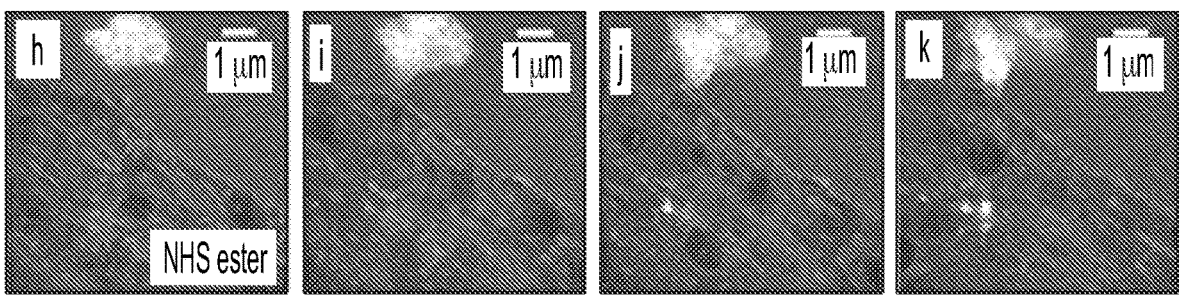
FIG. 2
CONTINUED

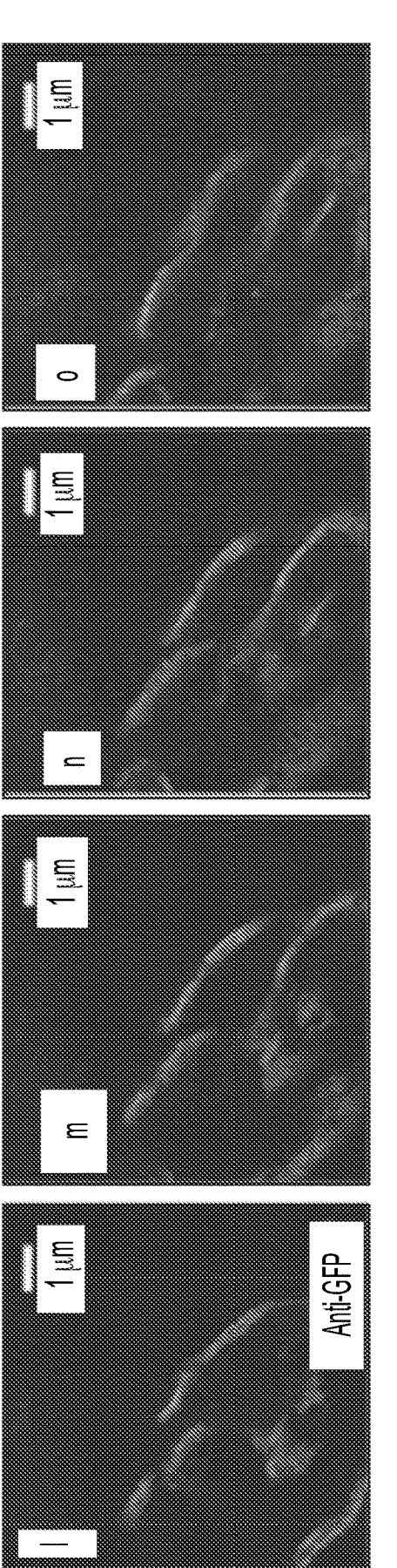
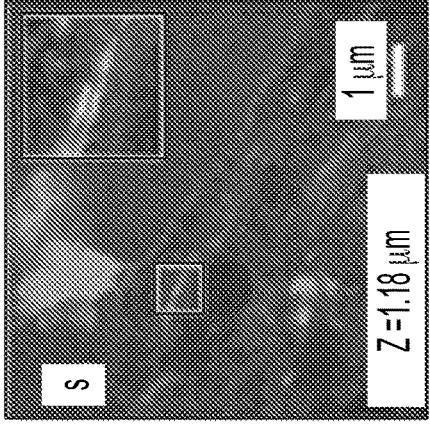
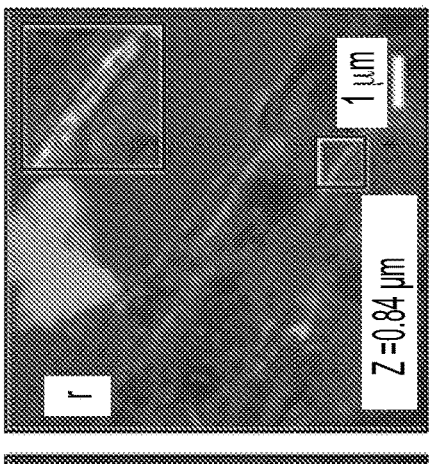
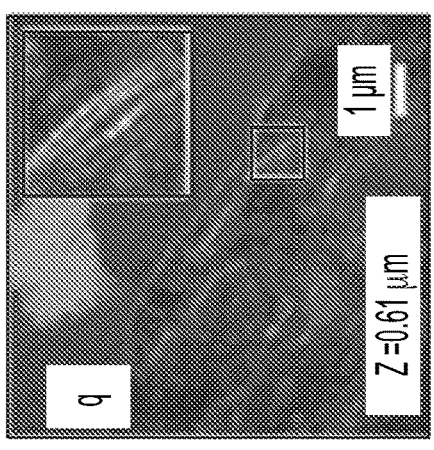
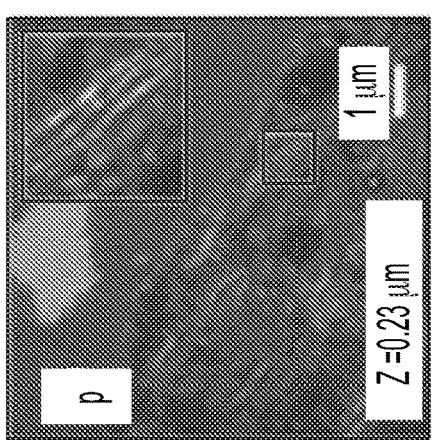
FIG. 2
CONTINUED

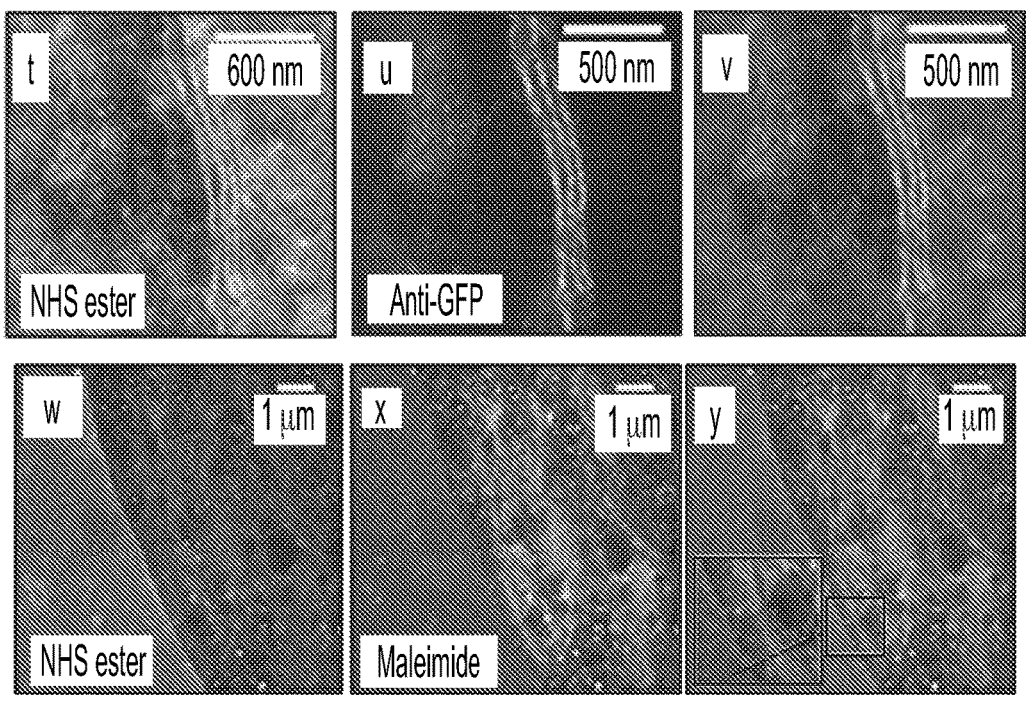
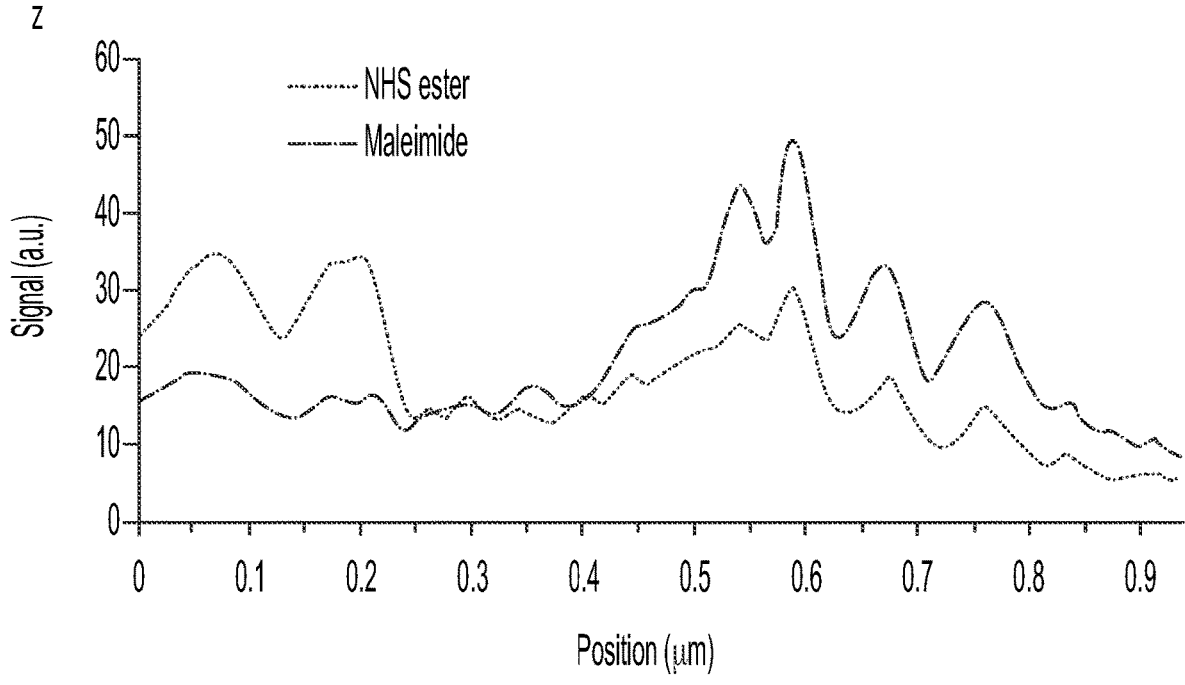
FIG. 2
CONTINUED

| Experiment number | Expansion factor |
|---|---|
| Experiment 1 | 14.67 |
| Experiment 2 | 14.33 |
| Experiment 3 | 13.13 |
| Experiment 4 | 13.49 |
| Experiment 5* | 21.03 |
* The cleavable crosslinker N,N'-Cystaminebisacrylamide (BAC) at a concentration of 0.1% (w/w) was used in the final hydrogel instead of BIS
FIG. 6
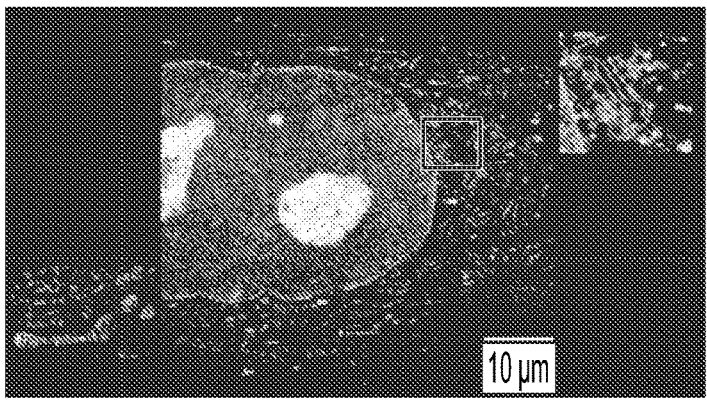
FIG. 7
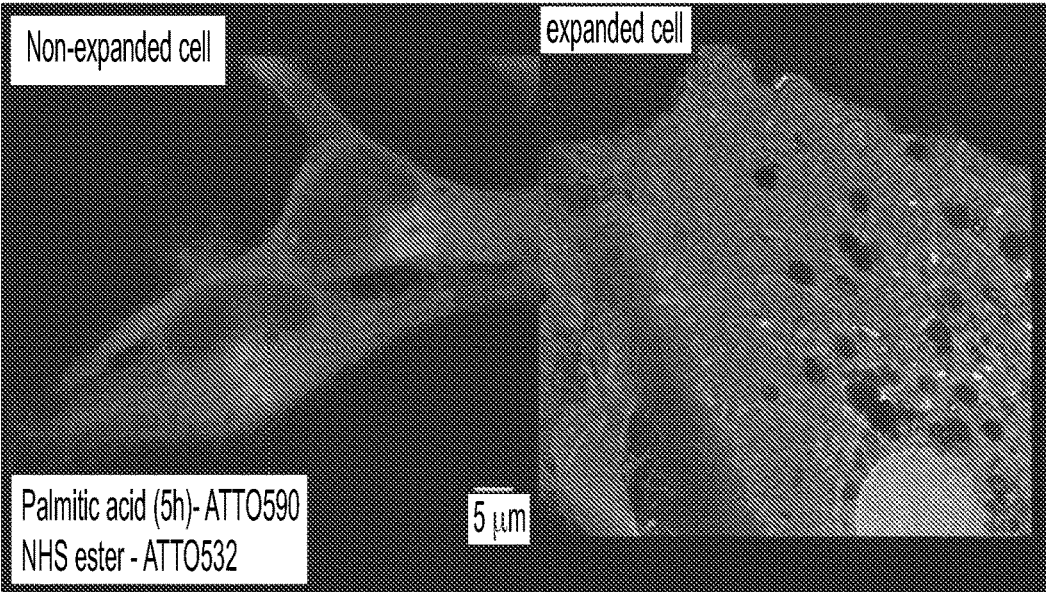
FIG. 8

PanExM expansion isotropy
Fluorescence microscopy
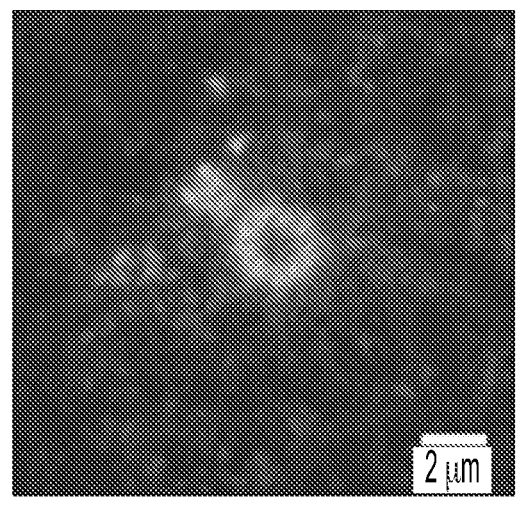
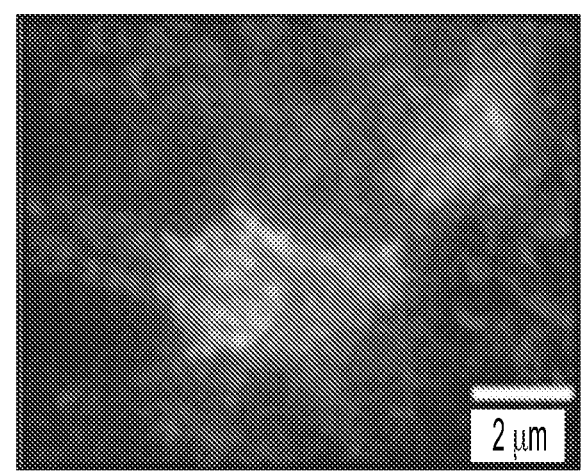
Diameter = ~2.2 μm
Expansion factor = 14
Centriole diameter/expansion factor = 157 nm
Electron microscopy
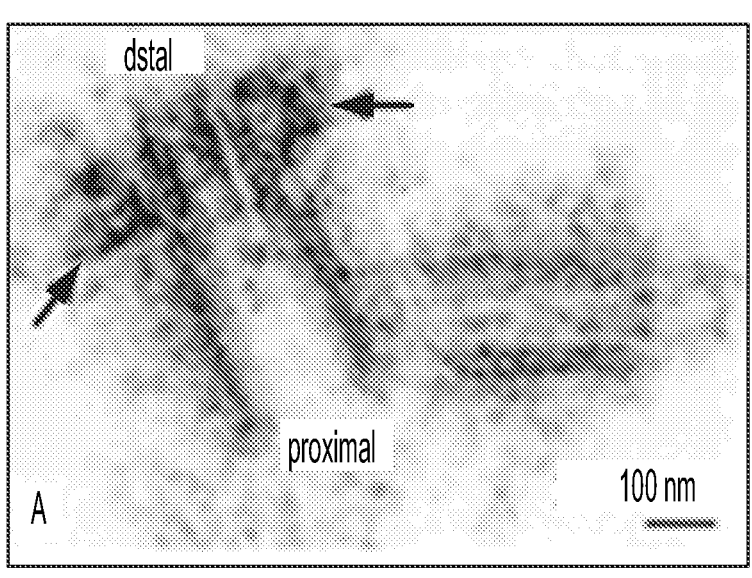
Delattre M. et al., *Journal of Cell Science*, (2007)
FIG. 11

Fluorescence microscopy                    Electron microscopy
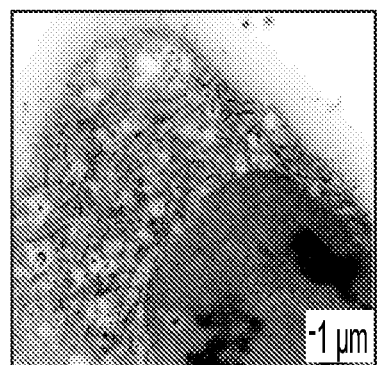 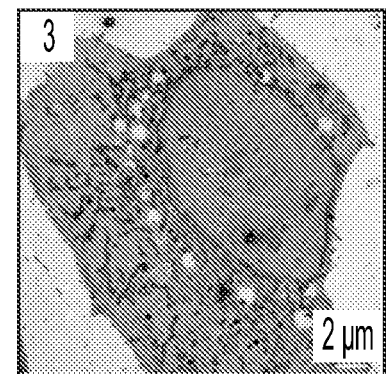
NHSester-ATTO594                    Peddie J.et al., *Ultramicroscopy* (2014)
63X/1.4 NA oil objective
FIG. 12

Fluorescence microscopy
Electron microscopy
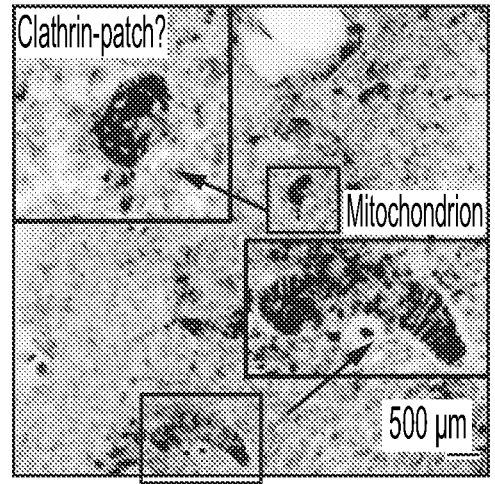
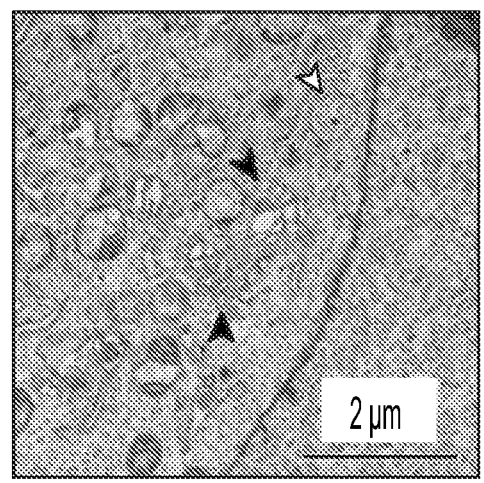
NHSester-ATTO594
100X/1.4 NA oil objective
Mousnier J.et al., *Journal of Virology* (2014)
FIG. 13

A
HYDROGEL EMBEDDING BY
FIXATIVE MODIFICATION
Protein
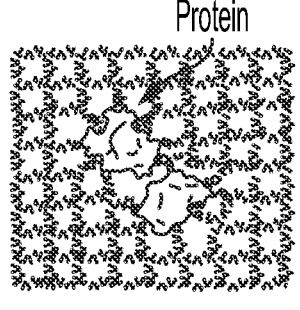
1st expansion gel
O   =
Lysine residue
1st expansion gel
B
FIRST EXPANSION
Denatured Protein
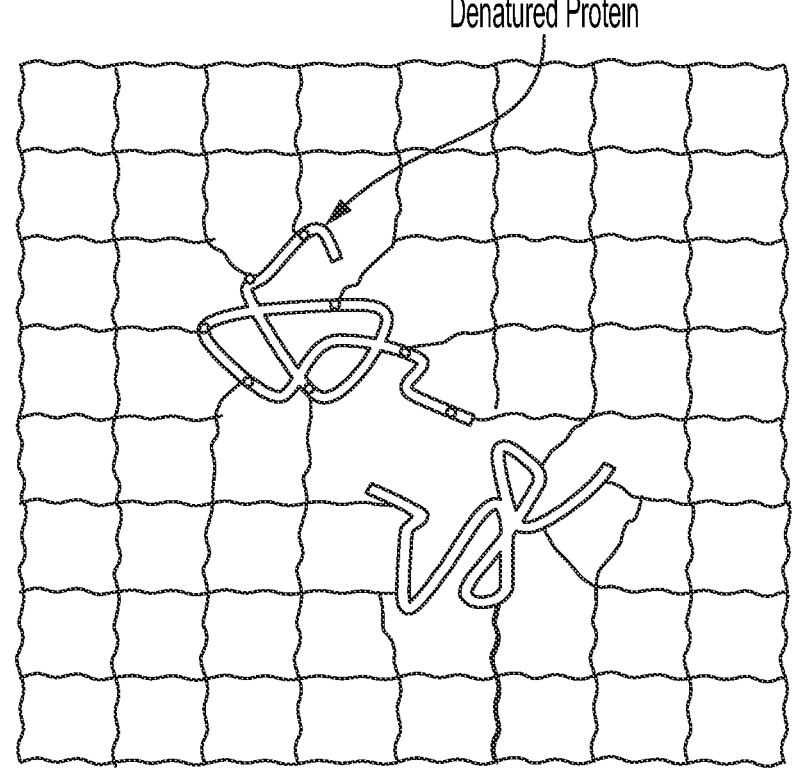
FIG. 22

C
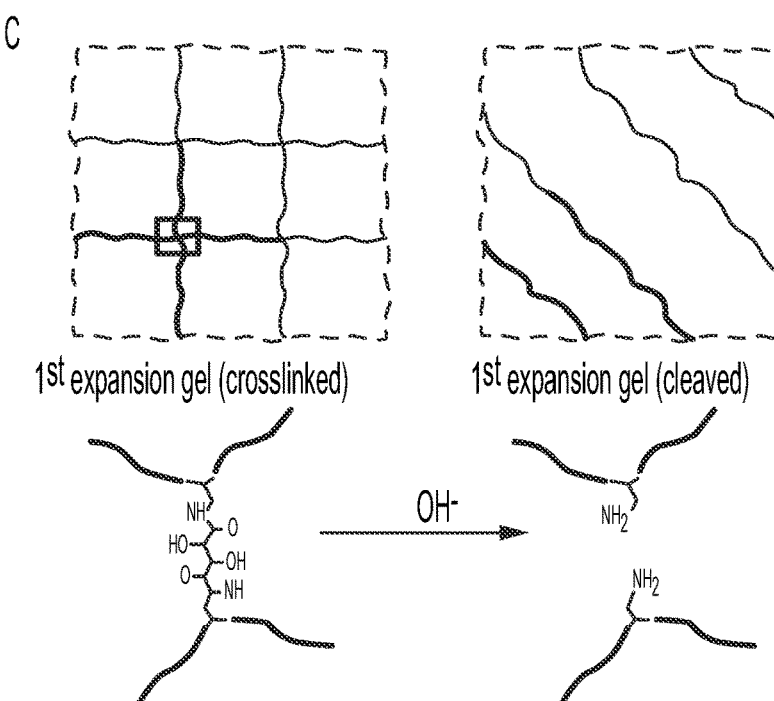
1st expansion gel (crosslinked)    1st expansion gel (cleaved)
D
EMBEDDING IN 2nd SWELLABLE GEL
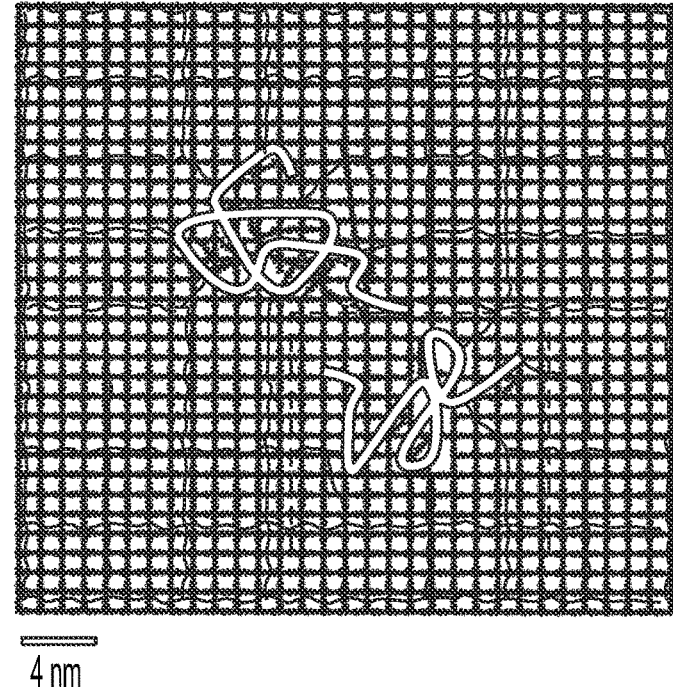
4 nm
FIG. 22
CONTINUED E
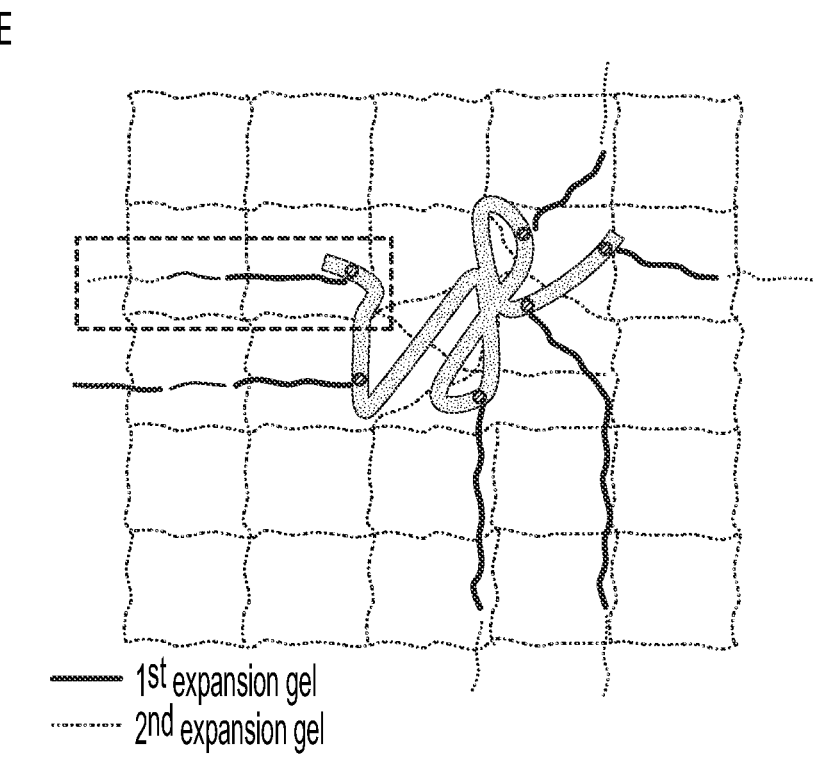
—————— 1st expansion gel
············ 2nd expansion gel
F
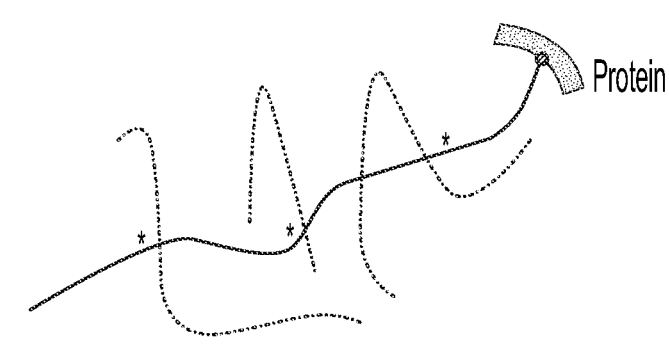
Protein
FIG. 22
CONTINUED

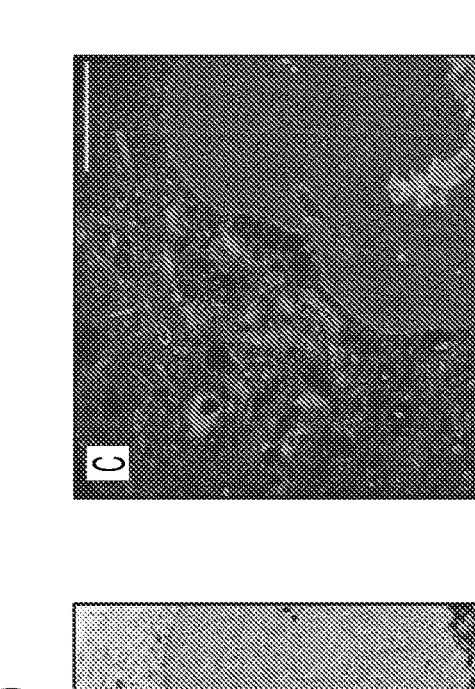
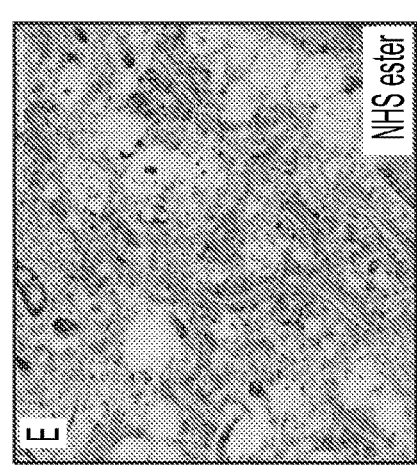
CONVENTIONAL IMMUNOFLUORESCENCE
NOVEL ULTRASTRUCTURAL CONTEXT ("pan-stain")
OVERLAY
NHS ester
Anti-GFP
FIG. 25

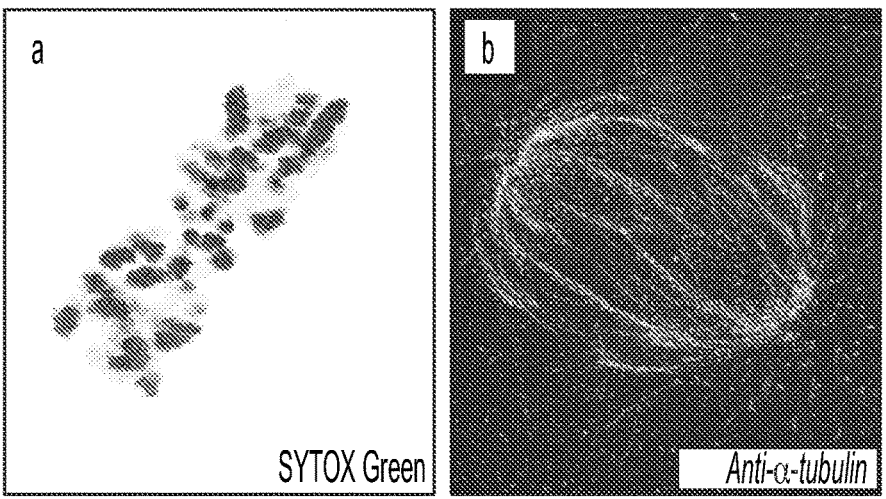
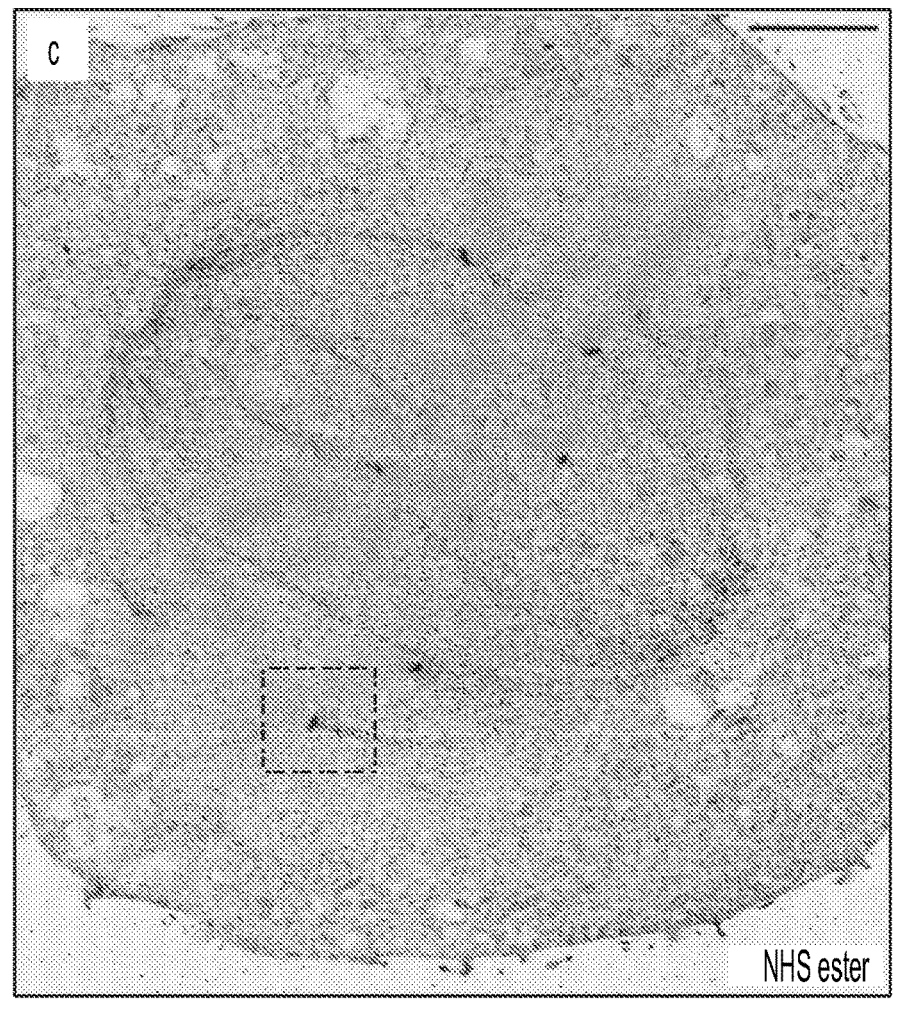
FIG. 29

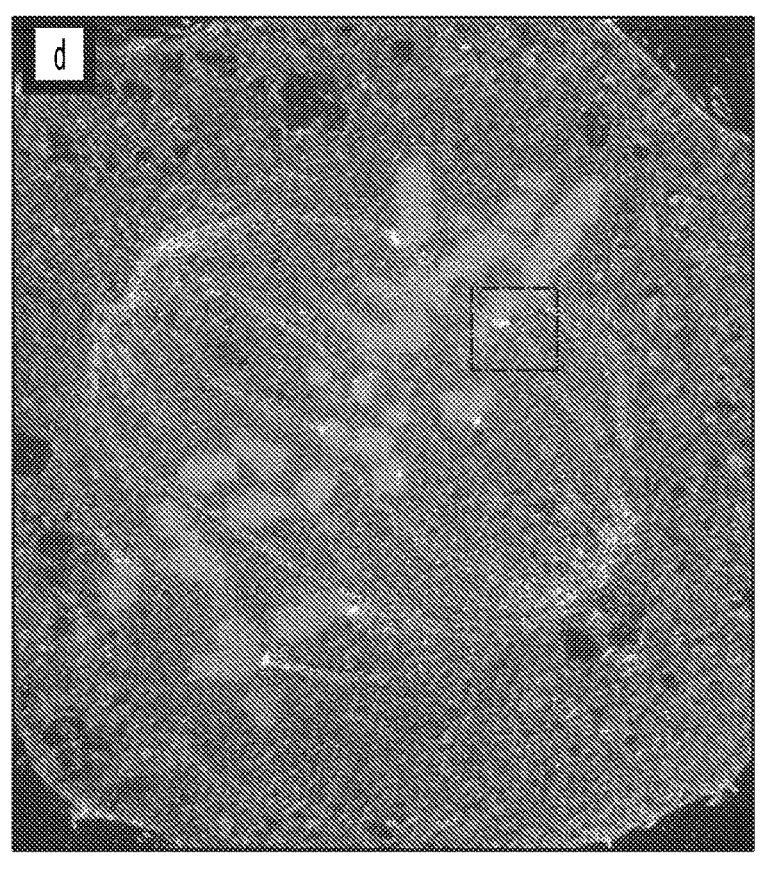
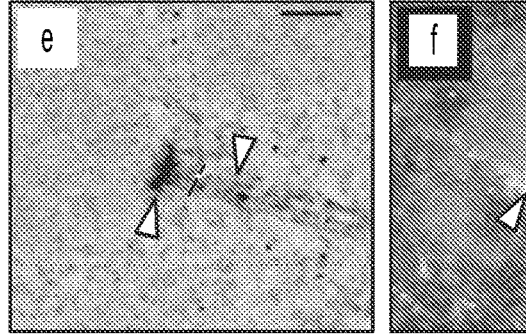
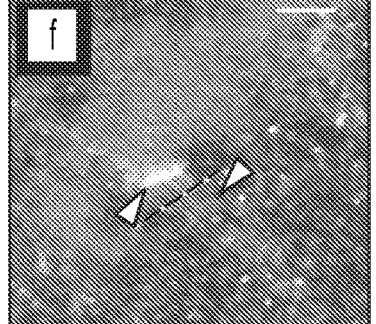
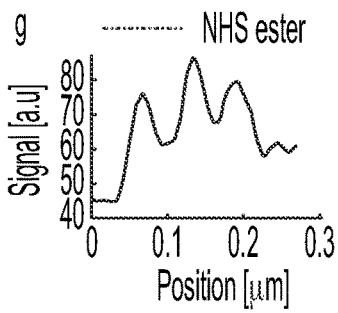
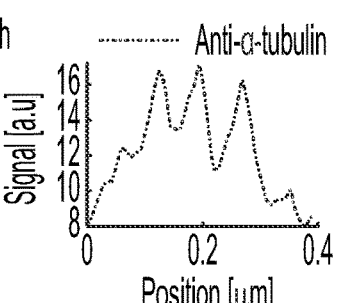
FIG. 29
CONTINUED

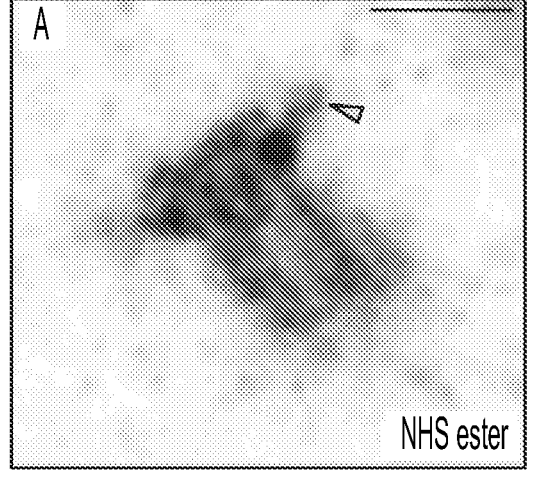
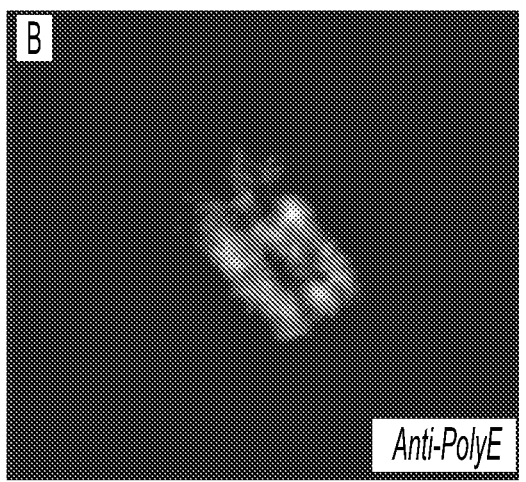
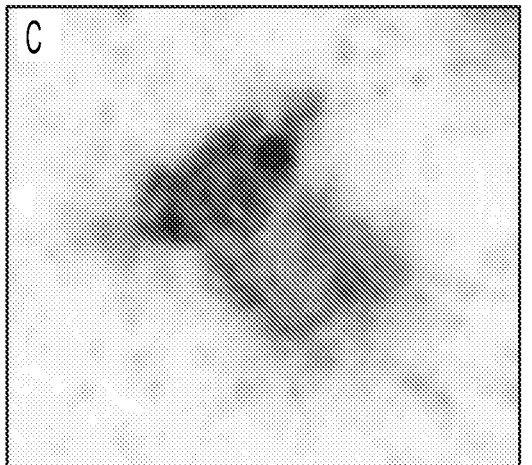
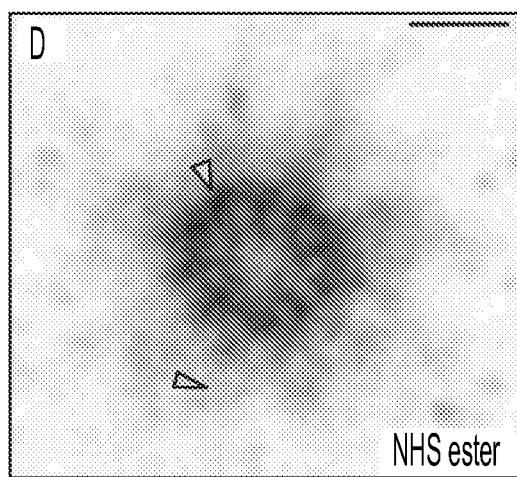
FIG. 30

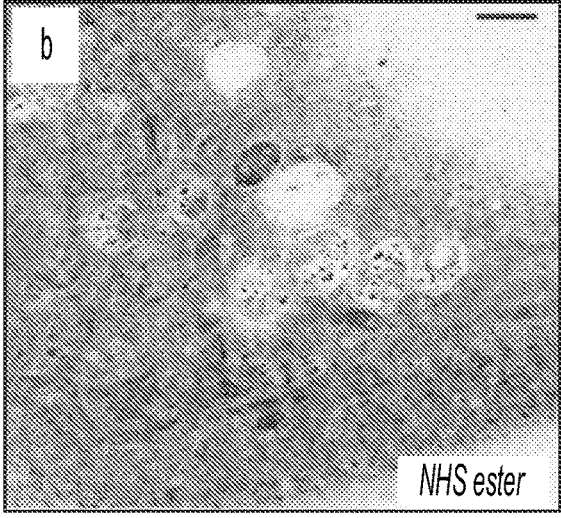
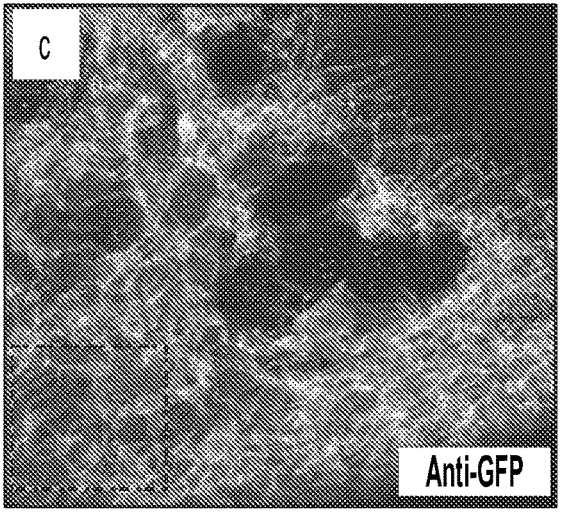
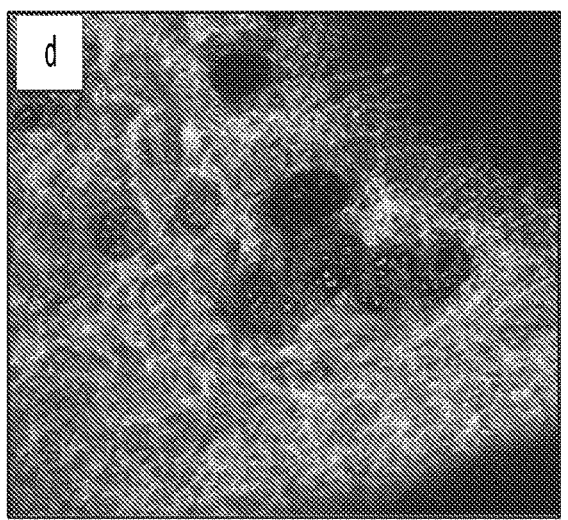
FIG. 31

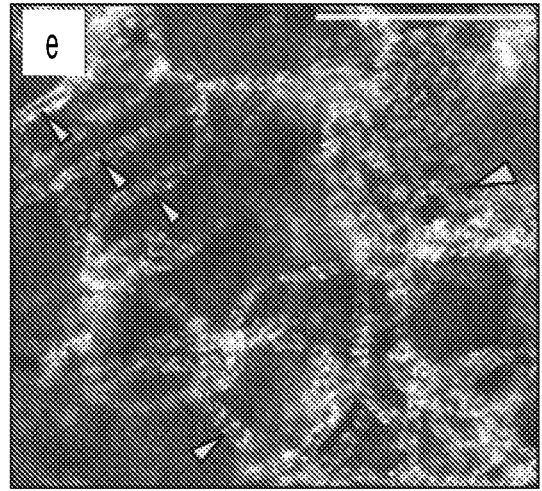
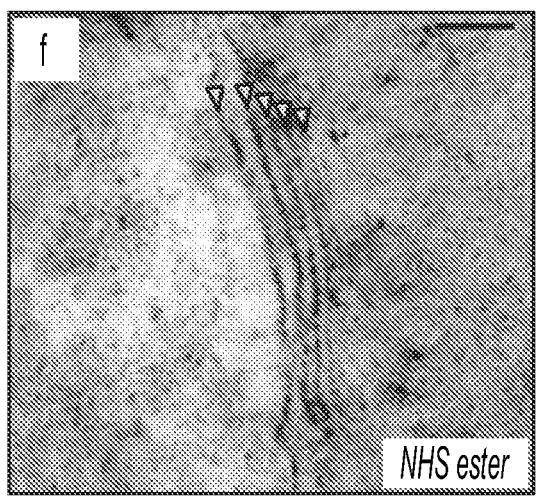
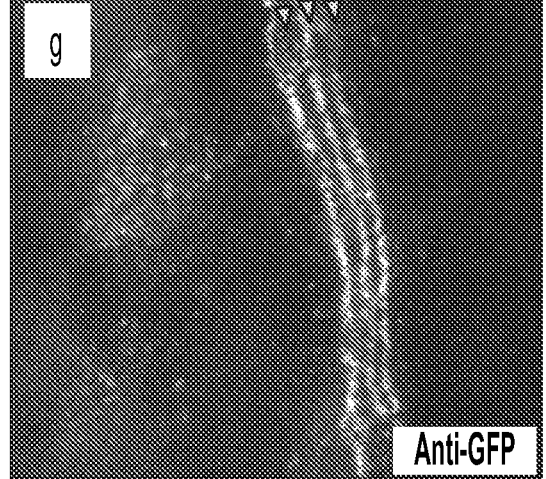
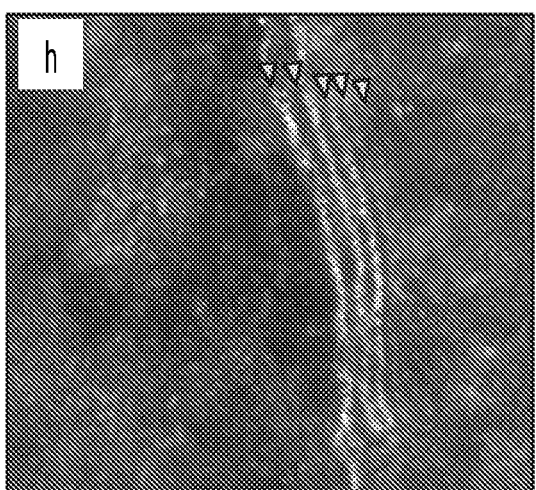
FIG. 31
CONTINUED

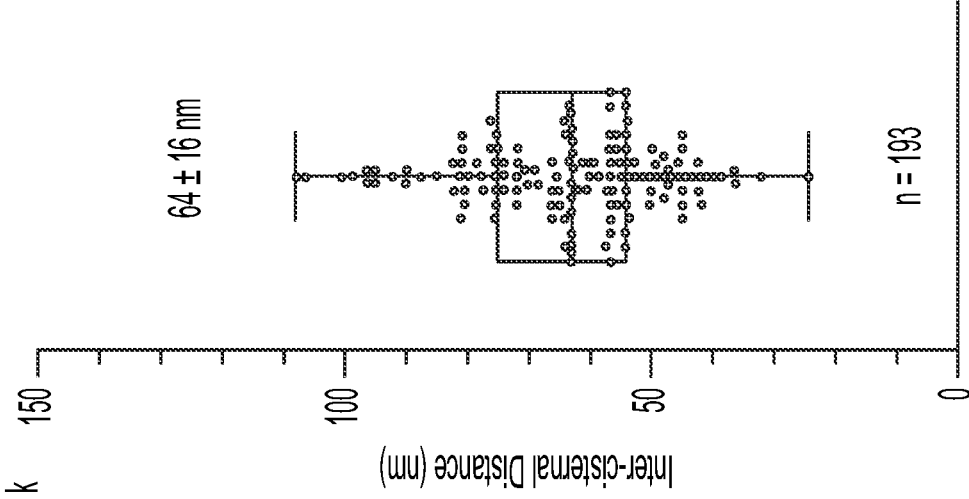
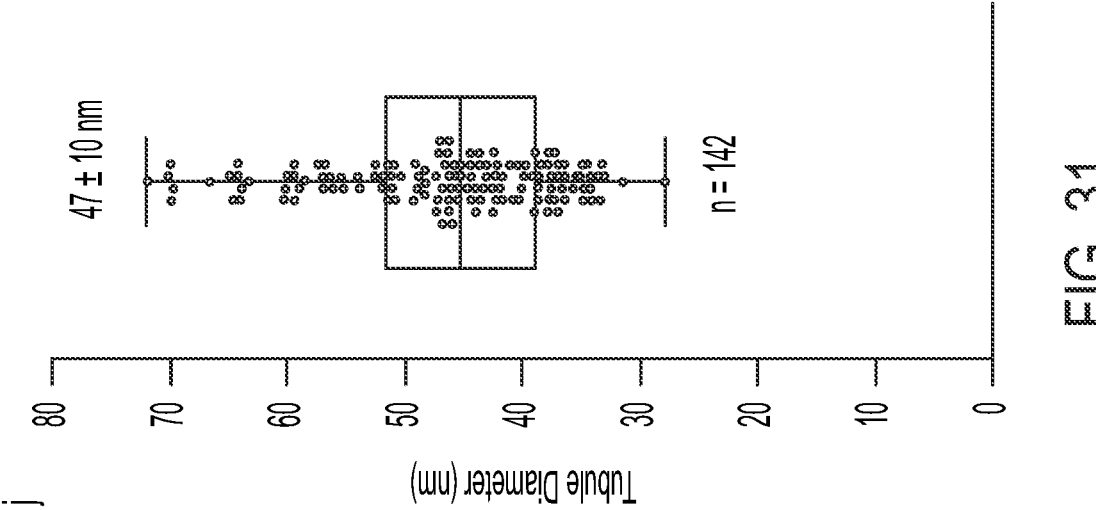
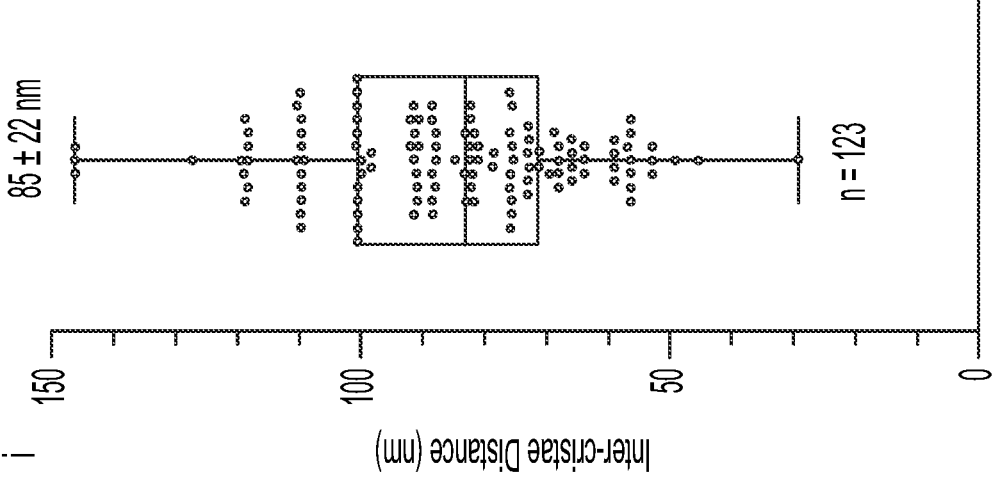
FIG. 31
CONTINUED

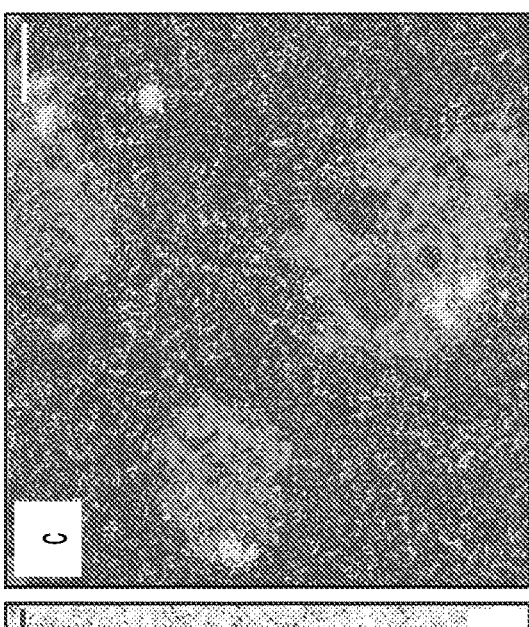
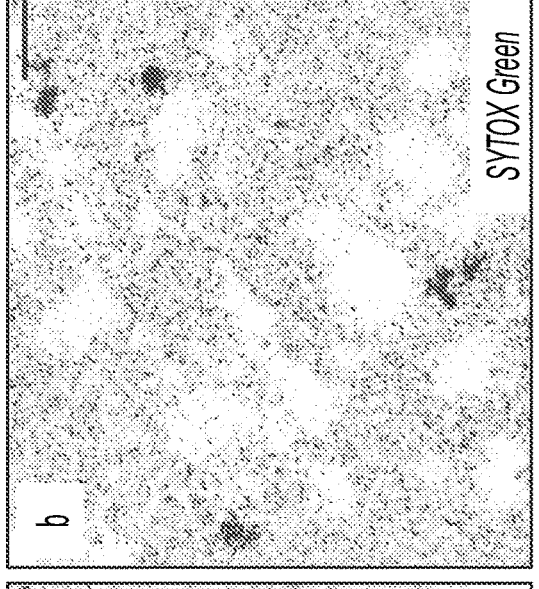
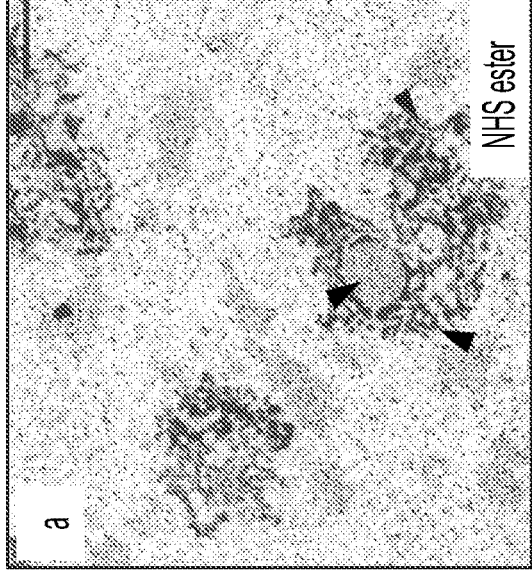
FIG. 35

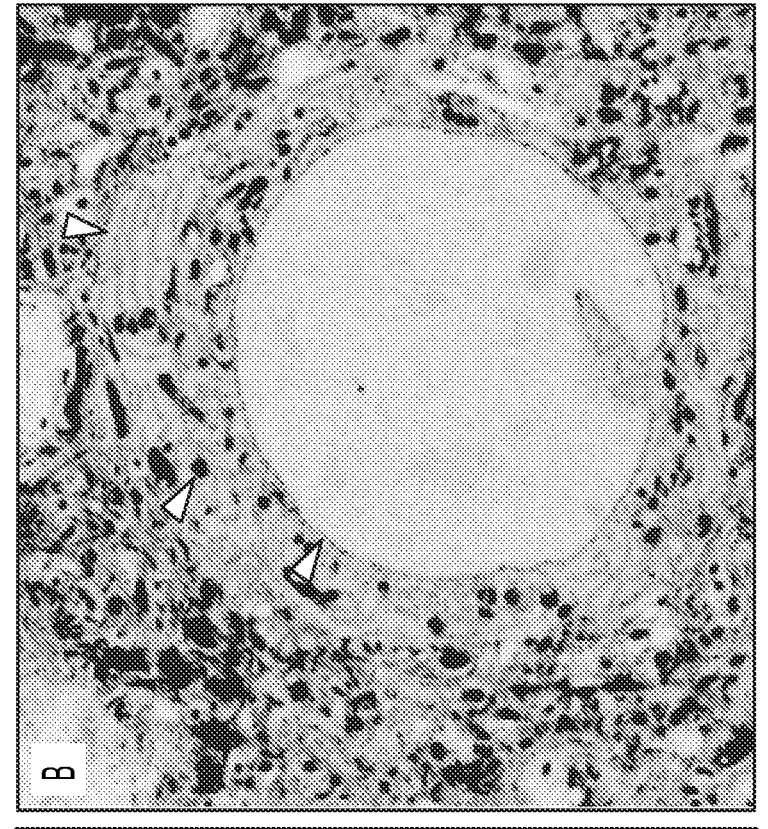
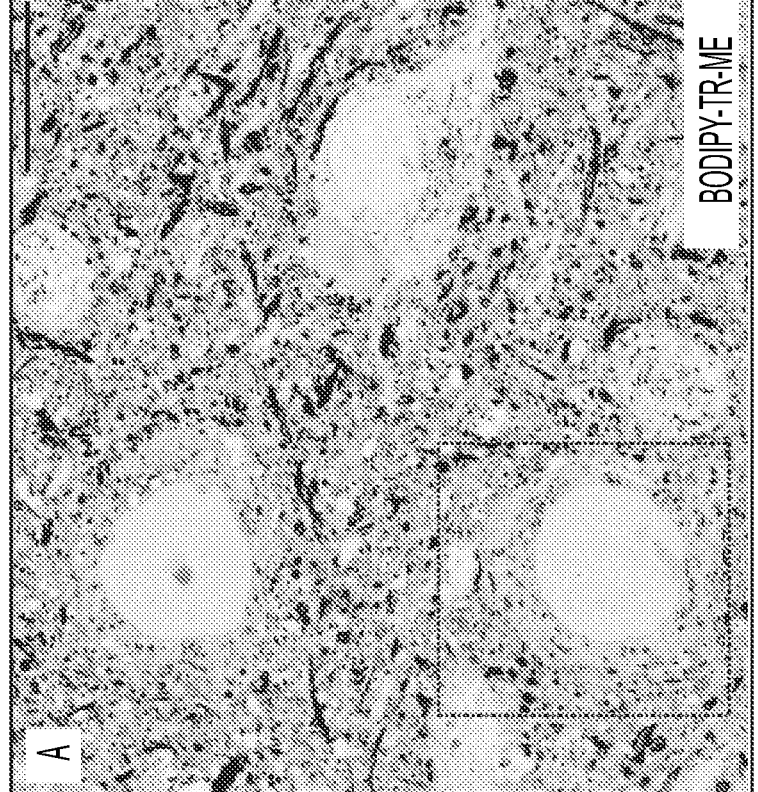
FIG. 38

C

| Experiment number | Expansion factor |
|---|---|
| Experiment 1 | 13.5 |
| Experiment 2 | 14.3 |
| *Experiment 3\** | *21.0* |
| Experiment 4 | 14.7 |
| Experiment 5 | 13.1 |
| Experiment 6 | 14.3 |
| Experiment 7 | 15.7 |

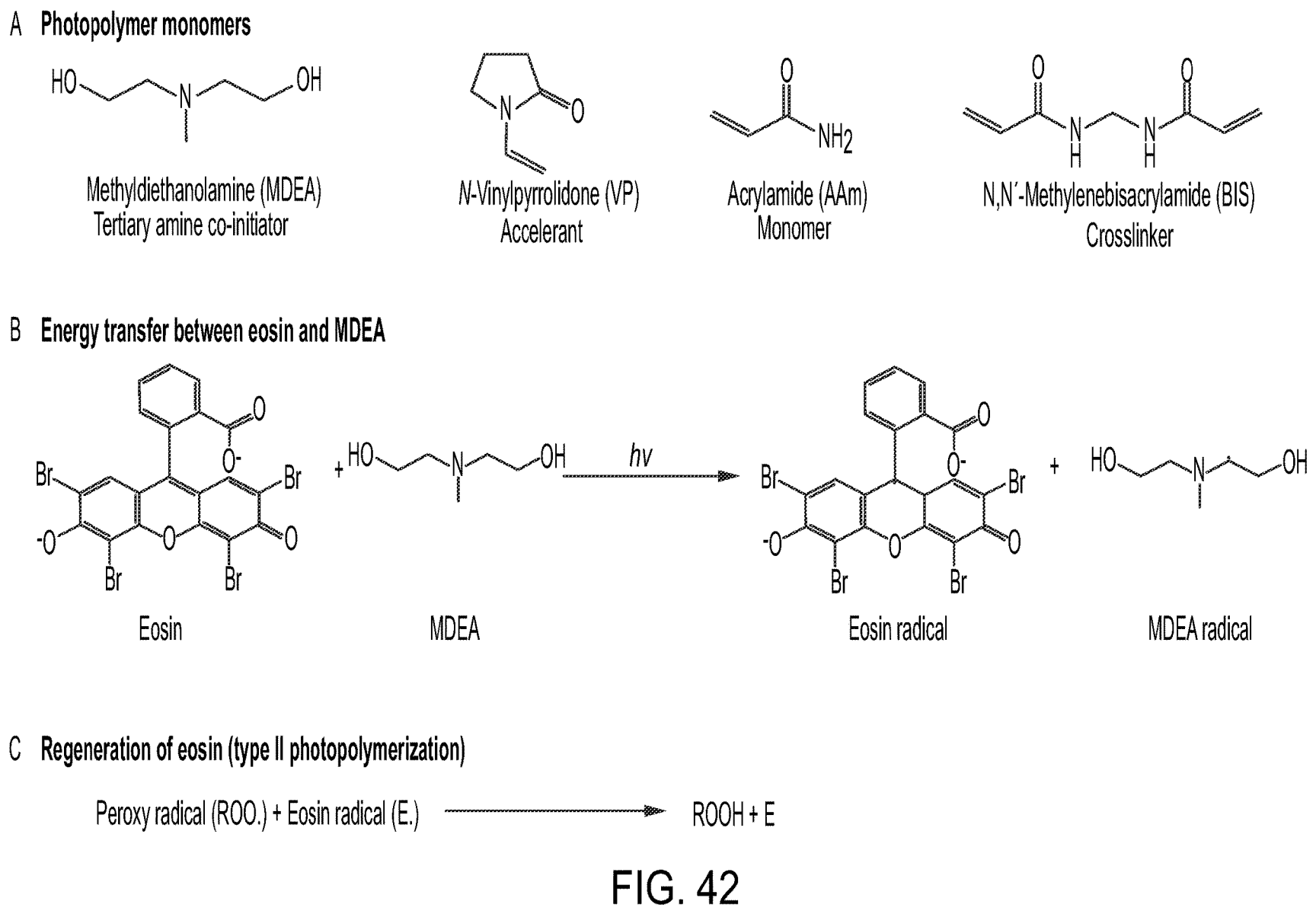

A  Photopolymer monomers

N-Vinylpyrrolidone (VP)
Accelerant

Acrylamide (AAm)
Monomer

N,N'-Methylenebisacrylamide (BIS)
Crosslinker

Methyldiethanolamine (MDEA)
Tertiary amine co-initiator

B  Energy transfer between eosin and MDEA

MDEA          Eosin radical

Eosin          MDEA radical

C  Regeneration of eosin (type II photopolymerization)

Peroxy radical (ROO.) + Eosin radical (E.)  ⟶  ROOH + E

FIG. 42

PHASE-CONTRAST    FLUORESCENCE    OVERLAY

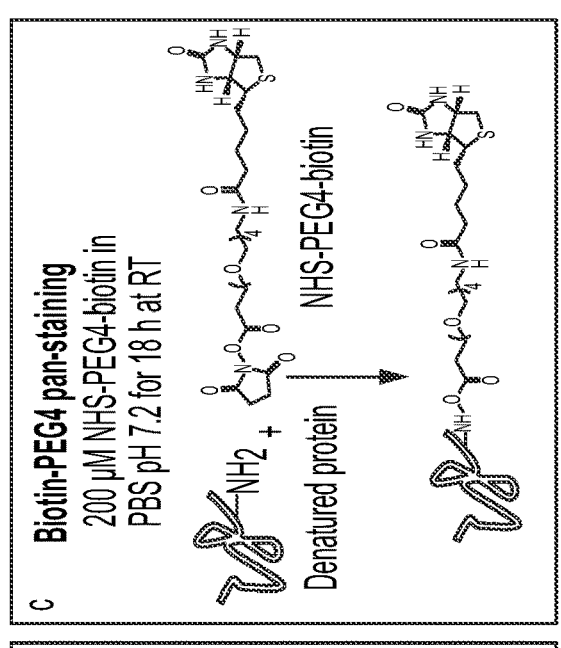
c    Biotin-PEG4 pan-staining
200 μM NHS-PEG4-biotin in
PBS pH 7.2 for 18 h at RT
NHS-PEG4-biotin
—NH₂ +
Denatured protein
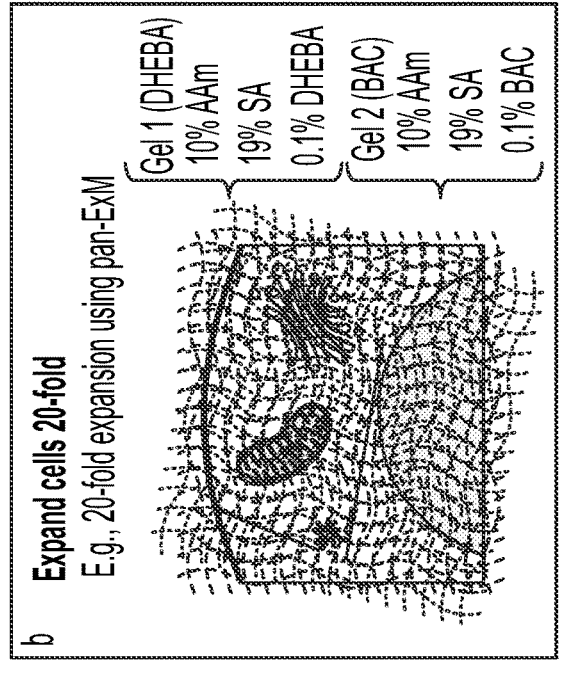
b    Expand cells 20-fold
E.g., 20-fold expansion using pan-ExM
Gel 1 (DHEBA)
10% AAm
19% SA
0.1% DHEBA
Gel 2 (BAC)
10% AAm
19% SA
0.1% BAC
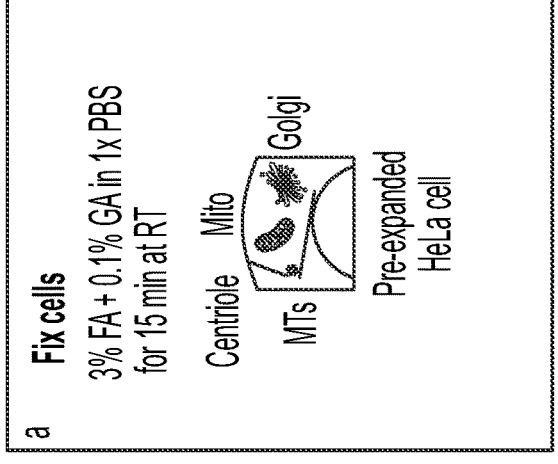
a    Fix cells
3% FA + 0.1% GA in 1x PBS
for 15 min at RT
Centriole    Mito    Golgi
MTs
Pre-expanded
HeLa cell
FIG. 48

D   Expand cells 100-fold
E.g., 100-fold expansion using pan-ExM
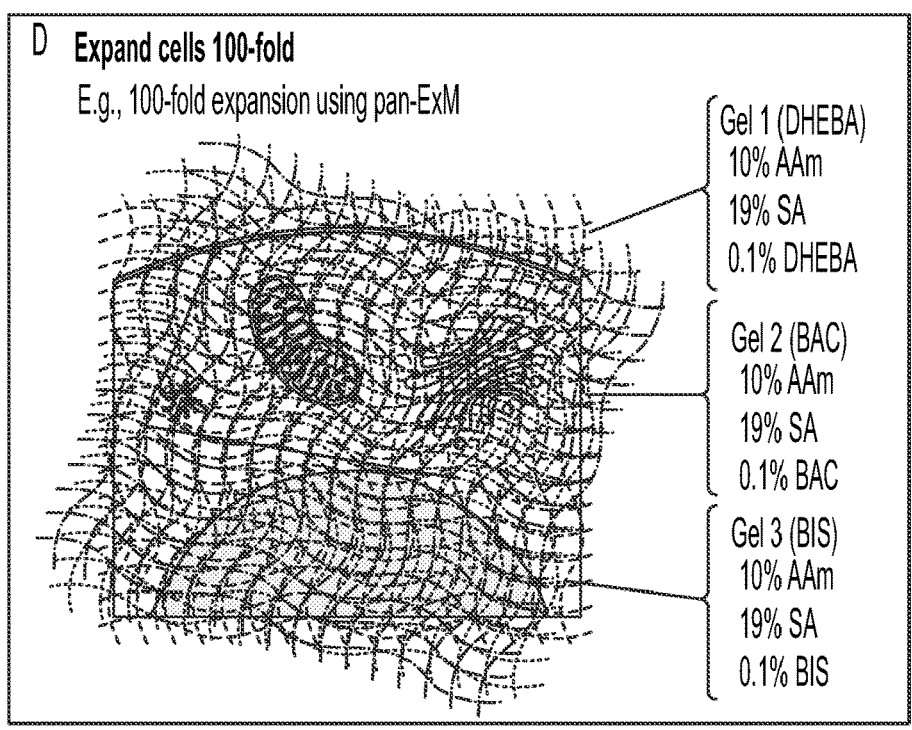
Gel 1 (DHEBA)
10% AAm
19% SA
0.1% DHEBA
Gel 2 (BAC)
10% AAm
19% SA
0.1% BAC
Gel 3 (BIS)
10% AAm
19% SA
0.1% BIS
E   Amplification of pan-stain with biotin dendrimers and eosin-ST
E-a 1 -20 µg/mL (20-360 nM) streptavidin-eosin
E-b 20 - 1000 µg/mL (2-70 nM) biotin-dendrimer
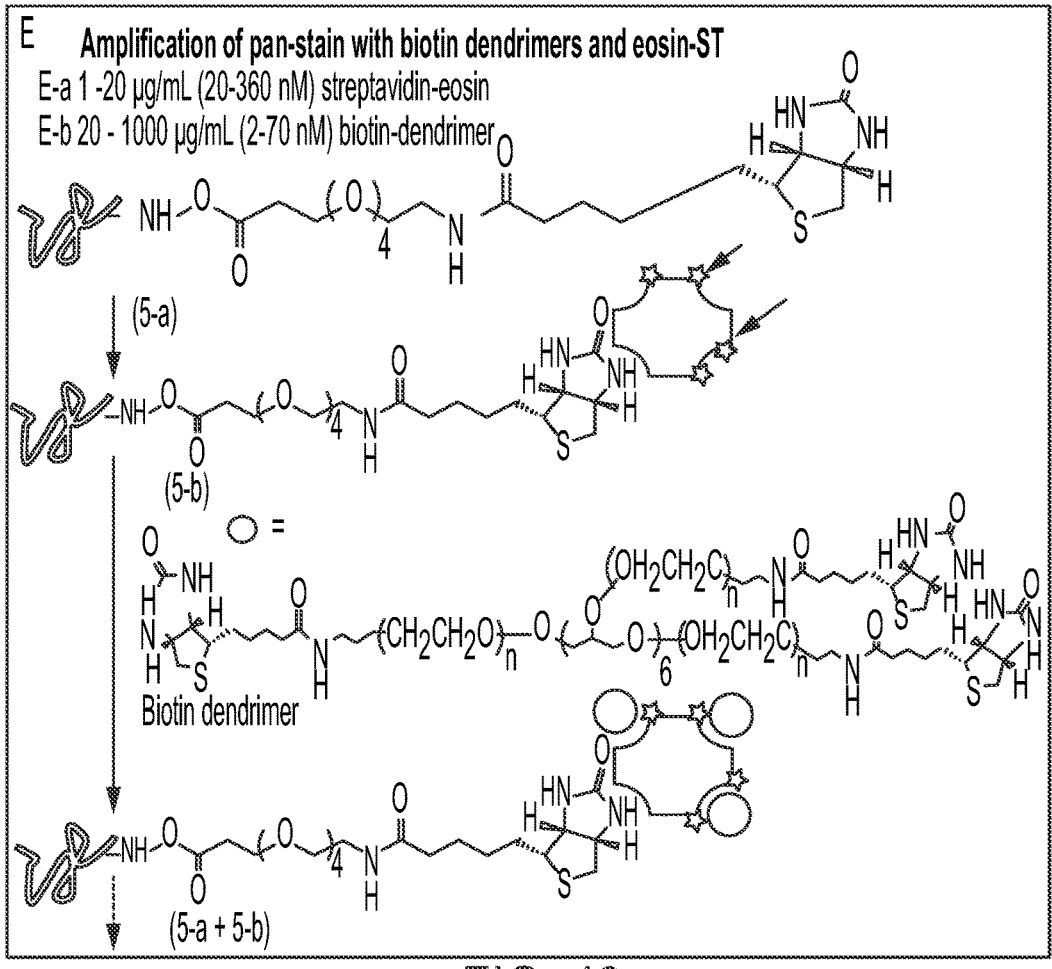
FIG. 48
CONTINUED

F    Polymerization-based signal amplification and polymer dye labeling

F-a Incubation in photo-polymerizable monomer solution

F-b Irradiation for 30 min with 530 nm light at 55 mW/cm$^2$

F-c Staining with 1 mg/mL Evans blue in PBS for 20 min

40% AAm
2% BIS
210 mM MDEA
35 mM VP 530 nm; 55 mW/cm2

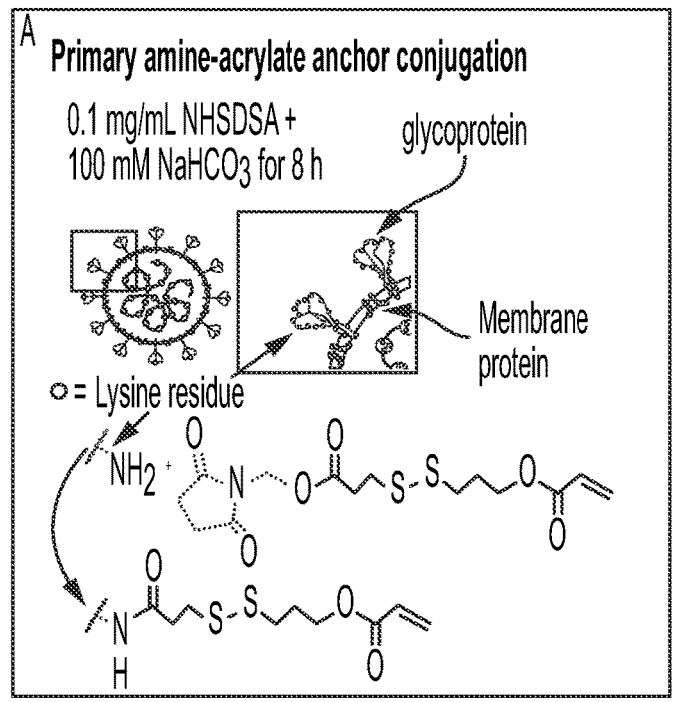
A Primary amine-acrylate anchor conjugation
0.1 mg/mL NHSDSA + 100 mM NaHCO$_3$ for 8 h
glycoprotein
Membrane protein
○ = Lysine residue
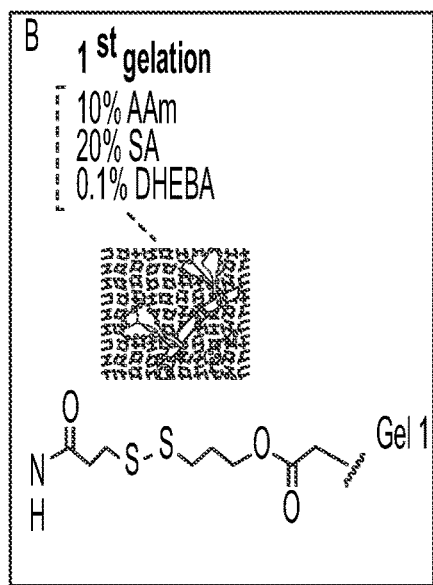
B 1$^{st}$ gelation
10% AAm
20% SA
0.1% DHEBA
Gel 1
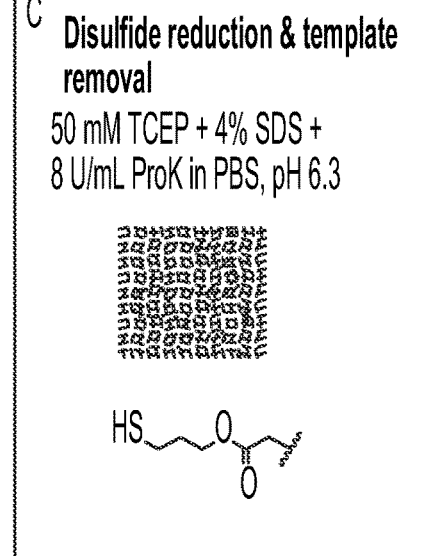
C Disulfide reduction & template removal
50 mM TCEP + 4% SDS + 8 U/mL ProK in PBS, pH 6.3
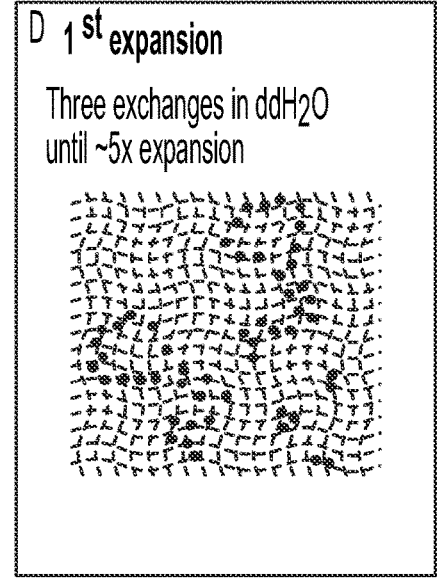
D 1$^{st}$ expansion
Three exchanges in ddH$_2$O until ~5x expansion
FIG. 50

METHODS AND SYSTEMS FOR PHYSICAL EXPANSION AND IMAGING OF BIOLOGICAL SAMPLES

STATEMENT REGARDING FEDERALLY SPONSORED RESEARCH OR DEVELOPMENT

This invention was made with government support under DK045735 and OD020142 awarded by National Institutes of Health. The government has certain rights in the invention.

CROSS-REFERENCE TO RELATED APPLICATIONS

This application is a national phase application under 35 U.S.C. § 371 of International Application No. PCT/US2021/022212, filed Mar. 12, 2021, which claims the benefit of priority under 35 U.S.C. § 119 (e) to U.S. Provisional Patent Application Ser. No. 62/989,158, filed Mar. 13, 2020. The entire contents of the applications are hereby incorporated by reference herein in their entireties.

BACKGROUND OF THE INVENTION

Fluorescence microscopy provides the benefits of high contrast imaging and high precision labeling. However, fluorescence microscopy is limited in the scope of a sample image, particularly imaging proteins in an ultrastructural context of a cell. Individual types of proteins can be labeled, which creates contrast and enables users to image them. The rest of the sample, however, remains unlabeled and thereby invisible in the fluorescence microscope. Labeling the rest of the sample to reveal this context does not provide a solution because it cannot be labeled at a sufficiently high density to reveal fine structures (ultrastructure) of the cell. Additionally, the optical resolution of fluorescence microscopy is not sufficient to reveal these fine structures. Related microscopy fields experience similar limitations. In electron microscopy (EM), three-dimensional images of a sample are feasible; however, three-dimensional images require days to weeks of continuous data acquisition in order to generate these images of a sample.

SUMMARY

The disclosure described herein provides light microscopy imaging methods for revealing cellular ultrastructures. The methods described herein combine the physical expansion of a sample with unspecific labeling of large portions of the expanded sample. Expanding the sample allows the user to bulk label the de-crowded sample at much higher densities than before and, if the factor of expansion is sufficiently large, enlarges the fine structures to a scale where structures can be resolved without the need for electron microscopy (EM) or specific labeling (e.g., immunofluorescence).

In one aspect of the disclosure, a method for preparing a biological sample for the purpose of generating images of its ultrastructure with an imaging instrument includes (a) physically expanding the sample by at least a factor of two in at least one dimension; and (b) bulk labeling a plurality of components of the sample with at least one reagent to introduce contrast.

This aspect can include a variety of embodiments. In one embodiment, the sample includes cellular components, a cell, a tissue section, a biofilm, a patient-derived sample, or a combination thereof.

In another embodiment, the sample is chemically fixed, cryo-preserved, unfixed, or a combination thereof.

In another embodiment, the imaging instrument includes a fluorescence light microscope, a transmitted light microscope, a reflected light microscope, a scattered light microscope, a super-resolution microscope, a cell phone camera, a camera, an ultrasound, an X-ray, a magnetic resonance, an electron microscope, or a combination thereof.

In another embodiment, the reagent to introduce contrast includes a fluorescent dye, a non-fluorescent dye, a metallic particle, a quantum dot, a dielectric particle, or a combination thereof.

In another embodiment, the reagent to introduce contrast is the initiator or catalyst of an amplification reaction. In some cases, the amplification reaction is in situ hybridization-based, click-chemistry based, enzyme-mediated, peroxidase-based, polymerization-based, or uses chromogenic or chemiluminescent substrates.

In another embodiment, at least one of the reagents bulk-labels proteins, post-translational protein modifications, amino acids, synthetic amino acids, synthetic metabolites, lipids, nucleotides, nucleic acids, carbohydrates, or a combination thereof.

In another embodiment, at least one of the reagents is an amine-reactive, a thiol-reactive, a carboxyl-reactive, a tyrosine-reactive, a glutamine-reactive, a lipophilic probe, or a combination thereof.

In another embodiment, at least one of the reagents is succinimidyl ester (including N-Hydroxysuccinimide (NHS) esters), isocyanate, isothiocyanate, benzoyl fluoride, carboxylic ester, tetrafluorophenyl (TFP) ester, sulfodichlorophenol (SDP) ester, carbonyl azide, or sulfonyl chloride, or an aldehyde-containing reagent including coumarins, pyrenes, o-phthaldialdehyde (OPA), odoacetamides, maleimides, 2-thiopyridine, 3-arylpropiolonitrile, benzylic halides, bromomethylketones, hydrazines, hydroxylamines, amines, or a combination thereof.

In another embodiment, at least two bulk labels are used to create multichannel images.

In another embodiment, sample features are automatically identified from the images by computational means.

In another embodiment, the sample is expanded by a factor of 12 to 24 in each direction.

In another embodiment, at least one additional reagent labels a cellular component specifically.

In another aspect, a method for preparing a biological sample includes (a) fixing the sample; (b) embedding the biological sample in a swellable polymer containing fixative-modifying monomers; (c) disrupting chemical bonds within the biological sample; (d) expanding the sample in a solvent; and (e) labeling the sample with at least one bulk label and expanding the sample in another solvent.

This aspect can have a variety of embodiments. In one embodiment, at least one of the reagents is an amine-reactive fixative and the swellable polymer contains at least one amine-functionalized monomer. In some cases, the amine-reactive fixative is heat-reversible such as formaldehyde (FA), or base-cleavable such as dimethyl suberimidate (DMS), dimethyl pimelimidate (DMP), and dimethyl adipimidate (DMA), or a combination thereof. In some cases, the at least one amine-functionalized monomer is acrylamide (AAm), allylamine (ADP), 2-vinylpyridine (2-VP), N-(2-Aminoethyl)acrylamide hydrochloride, 2-aminoethyl methacrylate hydrochloride, or a combination thereof.

In another embodiment, at least one of the reagents is thiol-cleavable and the swellable polymer contains at least one thiol-reactive monomer. In some cases, the thiol-cleavable fixative is dithiobis(succinimidyl propionate) (DSP), 1,5-difluoro-2,4-dinitrobenzene (DFDNB), succinimidyl 3-(2-pyridyldithio)propionate (SPDP), succinimidyl 6-(3(2-pyridyldithio)propionamido)hexanoate (LC-SPDP), or 4-succinimidyloxycarbonyl-alpha-methyl-α(2-pyridyldi-thio)toluene (SMPT), or a combination thereof. In some cases, the thiol-reactive monomer is pyridyl disulfide ethyl methacrylate (PDSMA), pyridyl disulfide ethyl acrylamide (PDSAAm), or a combination thereof.

In another embodiment, the swellable hydrogel is cross-linked with polymer crosslinkers such as piperazine diacry-lamide with concentrations between 0.001% and 0.2%.

In another embodiment, the sample is denatured with anionic detergents such as sodium dodecyl sulfate or chao-tropic reagents such as urea and guanidine hydrochloride, or a combination thereof.

In another aspect, a method for preparing a biological sample includes (a) embedding the sample in a non-swellable polymer where the polymer chains are covalently attached to molecules of the sample; (b) embedding the sample in a swellable hydrogel where the polymer chains are not anchored to molecules of the sample; (c) disrupting chemical bonds within the sample; (d) expanding the sample in a solvent where the majority of a proteome of the sample is retained predominantly by entanglement of a protein-polymer hybrid of step (a) with a swellable network of step (b); and (e) labeling the sample with at least one bulk label and expanding the sample in another solvent.

This aspect can include a variety of embodiments. In one embodiment, the non-swellable polymer is not crosslinked.

In another embodiment, the non-swellable polymer is between 0.01% and 80% w/w polymer. In another embodi-ment, the non-swellable polymer is crosslinked with non-cleavable crosslinkers at concentrations below 0.5% w/w.

In another embodiment, the non-swellable polymer is crosslinked with cleavable crosslinkers that are dissolved before, during, or after step (c).

In another embodiment, the non-swellable polymer con-tains a,b-unsaturated aldehyde polymers.

In another embodiment, the swellable hydrogel is cross-linked with polymer crosslinkers such as piperazine diacry-lamide with concentrations between 0.001% and 0.2%.

In another embodiment, the sample is denatured with anionic detergents such as sodium dodecyl sulfate or chao-tropic reagents such as urea and guanidine hydrochloride, or a combination thereof.

In another aspect, a method for preparing a biological sample can include (a) fixing the sample; (b) embedding the sample in a swellable polymer containing fixative-modify-ing monomers; (c) disrupting chemical bonds within the sample; (d) expanding the sample in a solvent; (e) re-embedding the sample in a neutral polymer crosslinked with cleavable crosslinkers; (f) re-embedding the sample in another swellable polymer crosslinked with a crosslinker different than the crosslinkers in the swellable polymer and the neutral polymer; (g) cleaving the first and second hydro-gel crosslinkers; and h) labeling the sample with at least one bulk label and expanding the sample in a solvent.

This aspect can include a variety of embodiments. In one embodiment, a majority of a proteome of the sample is retained predominantly by entanglement of protein-polymer hybrids in a polymer network and not covalent crosslinking.

In another aspect, a method for preparing a biological sample includes (a) embedding the sample in a non-swellable polymer where the polymer chains are covalently attached to molecules of the sample; (b) embedding the sample in a swellable hydrogel where the polymer chains are not attached to molecules of the sample; (c) disrupting chemical bonds within the sample; (d) expanding the sample in a suitable solvent; (e) re-embedding the sample in a neutral polymer crosslinked with cleavable crosslinkers; (f) re-embedding the sample in a swellable polymer crosslinked with a crosslinker different than the crosslinkers in the polymers of step (e); (g) leaving hydrogel crosslinkers of step (e) and step (f); and (h) labeling the sample with at least one bulk label and expanding the sample in a suitable solvent.

This aspect can include a variety of embodiments. In one embodiment, a majority of a proteome of the sample is retained predominantly by entanglement of protein-polymer hybrids in a polymer network and not covalent crosslinking.

In another aspect, a method for preparing a biological sample can include (a) fixing the sample; (b) embedding the sample in a polymer containing fixative-modifying mono-mers; (c) disrupting chemical bonds within the sample; (d) modifying the polymer network by inserting additional molecules into the polymer network to increase its size; and (e) labeling the sample with at least one bulk label and expanding the sample in a solvent.

This aspect can include a variety of embodiments. In one embodiment, the polymer of step (b) is swellable.

In another embodiment, polymer chains are grown by reversible addition-fragmentation chain-transfer (RAFT) polymerization of hydrophilic monomers. In some cases, the polymer chains are grown by RAFT photopolymerization of a thiocarbonate-crosslinked polymer network in the pres-ence of hydrophilic monomers, a photocatalyst, and a light source.

In another embodiment, the polymer of step (b) is syn-thesized with cleavable crosslinkers.

In another embodiment, the polymer of step (b) contains monomer, crosslinker, or polymer insertion sites, or a com-bination thereof. In some cases, the insertion site is a polymerizable molecule enabling in situ polymerization of monomer inserts. In some cases, the insertion site is conju-gated to a bifunctional linear polymer.

In another embodiment, the in situ-formed polymer or inserted bifunctional linear polymer contain new monomer or polymer insertion sites, permitting successive round of in situ polymerization or bifunctional linear polymer insertion, or a combination thereof.

In another embodiment, the in situ-formed or inserted polymer chains are swellable.

In another embodiment, step (d) occurs before step (c) or after step (e).

In another aspect, a method for preparing a biological sample can include (a) embedding the sample in a non-swellable polymer where the polymer chains are covalently attached to molecules of the sample; (b) embedding the sample in a hydrogel where the polymer chains are not attached to molecules of the sample; (c) disrupting chemical bonds within the sample; (d) modifying the polymer net-work by inserting additional molecules into the polymer chains; and (e) labeling the sample with at least one bulk label and expanding the sample in a suitable solvent.

This aspect can include a variety of embodiments. In one embodiment, the polymer of step (d) is swellable.

In another embodiment, polymer chains are grown by reversible addition-fragmentation chain-transfer (RAFT) polymerization of hydrophilic monomers. In some cases, polymer chains are grown by RAFT photopolymerization of a thiocarbonate-crosslinked polymer network in the pres-ence of hydrophilic monomers, a photocatalyst, and a light source.

In another embodiment, the polymer of step (d) is synthesized with cleavable crosslinkers.

In another embodiment, the polymer of step (d) contains monomer, crosslinker, or polymer insertion sites, or a combination thereof. In some cases, the insertion site is a polymerizable molecule enabling in situ polymerization of monomer inserts. In some cases, the insertion site is conjugated to a bifunctional linear polymer.

In another embodiment, the in situ-formed polymer or inserted bifunctional linear polymer contain new monomer or polymer insertion sites, permitting successive round of in situ polymerization or bifunctional linear polymer insertion, or a combination thereof.

In another embodiment, the in situ-formed or inserted polymer chains are swellable.

In another embodiment, step (d) occurs before step (c) or after step (e).

In another aspect, a method for preparing a biological sample for visualizing cellular and sub-cellular structures below a resolution of a human eye using an unaided human eye can include a) physically expanding the sample by at least a factor of ten in at least one dimension; and b) bulk labeling a plurality of components of the sample with at least one reagent to introduce contrast visible by the unaided human eye.

This aspect can include a variety of embodiments. In one embodiment, the visible contrast is an organic or inorganic pigment, a synthetic or natural visible dye, or a metallic particle, or a combination thereof.

In another embodiment, the visible contrast is a substance of refractive index higher than 1.33, where the substance includes polymers, plastics, glass, liquids, solids, or a combination thereof.

In another embodiment, the reagent to introduce contrast is an initiator or catalyst of an amplification reaction, or a combination thereof. In some cases, the amplification reaction is in situ hybridization-based, click-chemistry based, enzyme-mediated, peroxidase-based, polymerization-based, or uses chromogenic or chemiluminescent substrates, or a combination thereof. In some cases, the chromogenic substrate is a peroxidase substrate such as tyramide conjugates, 3,3'-diaminobenzidine (DAB), 3,3',5,5'-tetramethylbenzidine (TMB), 3-amino-9-Ethylcarbazole (AEC), and 2,2'-azino-di-[3-ethylbenzthiazoline-6-sulfonic acid] (ABTS), or a combination thereof. In some cases, the reagent initiates polymerization-based signal amplification.

In some cases, the polymerization-based signal amplification is photo-initiated or enzyme-mediated, or a combination thereof. In some cases, the polymer formed is acrylamide, acrylate, or polyethylene glycol (PEG) based, or a combination thereof. In some cases, the photoinitiator is eosin dye. In some cases, the polymer formed via the polymerization is of a higher refractive index than a swellable polymer used for sample expansion. In some cases, the polymer formed via the polymerization-based signal amplification is stained with visible dyes. In some cases, the visible dye is an azo dye such as Evans Blue (T-1824) or Direct Red 81 (disodium 7-benzamido-4-hydroxy-3-[[4-[(4-sulphonatophenyl)azo]phenyl]azo]naphthalene sulphonate), or a combination thereof.

In another embodiment, the visualized structures are single cells, cellular organelles, or ultrastructural features, or a combination thereof.

In another embodiment, the sample visualized is microbial.

In another embodiment, the sample expands more than 25-fold.

In another embodiment, at least two bulk labels are used to create multichannel images.

In another embodiment, at least one additional reagent labels a cellular component specifically.

In another embodiment, an imaging instrument for imaging the sample is one of the a fluorescence light microscope, a transmitted light microscope, a reflected light microscope, a scattered light microscope, a super-resolution microscope, a cell phone camera, a camera, an ultrasound, an X-ray, a magnetic resonance, an electron microscope, or a combination thereof.

In another aspect, a method for preparing a sample can include (a) embedding the sample in a polymer network such that at least some molecules of the sample are covalently crosslinked to the polymer network; (b) physically expanding the polymer network by at least a factor of two in at least one dimension; and (c) labeling interfaces between the polymer network and the sample with a reagent to create an expanded representation of at least some sample components.

This aspect can include a variety of embodiments. In one embodiment, the sample components include individual proteins, protein complexes, bacteria, viruses, or a combination thereof.

In another embodiment, the sample is aldehyde-fixed during the polymer embedding step.

In another embodiment, the sample is crosslinked to the polymer network by a cleavable molecule which is cleaved, and its polymer-anchored component labeled to represent an interface of the polymer network and the sample. In some cases, the cleavable molecule contains an amino acid-reactive group, a hydrogel-reactive group, and a cleavable linker. In some cases, the cleavable linker is a disulfide bridge.

In another aspect, a method for preparing a sample includes (a) embedding the sample in a polymer network such that at least some molecules of the sample are covalently crosslinked to the polymer network; (b) modifying the polymer network by inserting additional molecules into the polymer network to enlarge the polymer network; and (c) labeling interfaces between the polymer network and the sample with a reagent in order to create an expanded representation of at least some sample components.

This aspect can include a variety of embodiments. In one embodiment, the polymer of step (c) is swellable.

In another embodiment, polymer chains are grown by reversible addition-fragmentation chain-transfer (RAFT) polymerization of hydrophilic monomers. In some cases, polymer chains are grown by RAFT photopolymerization of a thiocarbonate-crosslinked polymer network in the presence of hydrophilic monomers, a photocatalyst, and a light source. In some cases, the polymer of step (c) is synthesized with cleavable crosslinkers.

In another embodiment, the polymer of step (c) contains monomer, crosslinker, or polymer insertion sites, or a combination thereof. In some cases, the insertion site is a polymerizable molecule enabling in situ polymerization of monomer inserts. In some cases, where the insertion site is conjugated to a bifunctional linear polymer.

In another embodiment, the in situ-formed polymer or inserted bifunctional linear polymer contain new monomer or polymer insertion sites, permitting successive round of in situ polymerization or bifunctional linear polymer insertion, or a combination thereof.

In another embodiment, the in situ-formed or inserted polymer chains are swellable.

In another aspect, a method for preparing a sample includes (a) embedding the sample in a polymer network such that at least some molecules of the sample are covalently crosslinked to the polymer network; (b) physically expanding the polymer network by at least a factor of two in at least one dimension; (c) re-embedding the sample in a neutral polymer crosslinked with cleavable crosslinkers; (d) re-embedding the sample in a swellable polymer crosslinked with a crosslinker different than the crosslinkers in the polymers of step (a) and step (c); e) cleaving hydrogel crosslinkers of step (a) and step (c); and f) labeling interfaces between the polymer network and the sample with a reagent in order to create an expanded representation of at least some sample components.

This aspect can include a variety of embodiments. In one embodiment, the sample is crosslinked to the polymer network in step (a) by a cleavable molecule which is cleaved, and its polymer-anchored component labeled to represent an interface of the polymer network and the sample. In some cases, the cleavable molecule contains an amino acid-reactive group, a hydrogel-reactive group, and a cleavable linker. In some cases, the cleavable linker is a disulfide bridge.

In another embodiment, the sample is crosslinked to the polymer network in step (a) by a cleavable molecule which is cleaved after step (a), and its polymer-anchored component re-crosslinked to the polymer network in step (d) and subsequently cleaved and labeled to represent the interface. In some cases, the molecule contains an amino acid-reactive group, a hydrogel-reactive group, and a cleavable linker. In some cases, the cleavable linker is a disulfide bridge.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

8 box in D, revealing individual ER tubules, clearly resolved as hollow tubules (arrow heads), and a dense network of ER tubules (arrow). (g) distribution of ER tubule diameters (n=142, N=2 cells). (h)-(s) images from a 3D image stack featuring the Golgi complex next to the nucleus of a HeLa cell expressing Golgi-localized ManII-GFP. (h)-(k) NHS ester images at axial positions 0.23, 0.61, 0.84 and 1.18 μm, respectively. (l)-(o) anti-GFP images of the same fields of view as H-K. (p)-(s) overlay of (h)-(o). (t) STED super-resolution image showing the NHS ester channel of a Golgi stack in a ManII-GFP expressing HeLa cell. (u) anti-GFP STED image of the same area. (v) overlay of (t)-(u). (w)-(y) nuclear periphery of a HeLa cell (nucleus on the left) labeled with NHS ester and maleimide, revealing the cysteine-enriched Golgi complex. (w) NHS ester channel. (x) maleimide channel. (y) overlay of (w)-(x). The inset shows the zoomed-in white box. (z) line profile along the dashed line in y, revealing the change in NHS ester to maleimide staining across the Golgi and nucleus. All scales are corrected for the determined expansion factor. For box plots, median and interquartile range are shown with whiskers drawn down to the minimum and maximum values.

Figure 1:
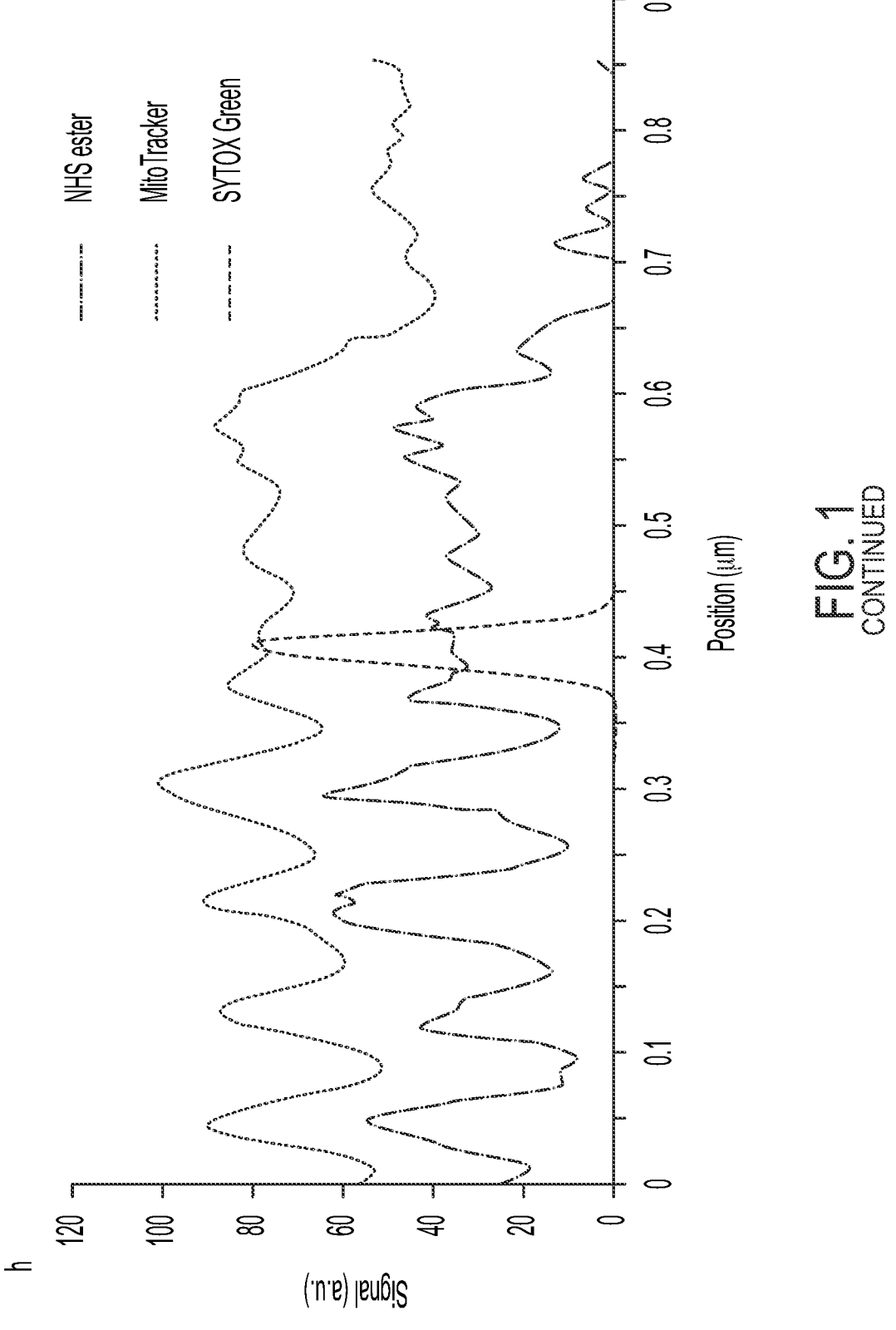
FIG. 1 provides images of samples expanded through an iterative expansion technique, according to an embodiment of the claimed invention. (a) Non-expanded HeLa cell. (b) HeLa cell expanded once. (c) pan-ExM expanded HeLa cell. The area in the orange box is shown in inset, revealing Golgi cisternae (arrow heads). The cells in (a)-(c) were labeled with NHS ester. (d) magnified box in (c), showing cristae in mitochondria. (e) MitoTracker Orange stain in the same area. (f) SYTOX™ Green stain showing DNA in mitochondrial nucleoids. (g) overlay of (d)-(f). (h), cross-section along the dashed line shown in (g). (i) NETS-ester rich area in a HeLa cell nucleus showing a nucleolus. (j) SYTOX Green DNA stain corresponding to area shown in (i). (k), overlay of (i)-(j). (l) cross-section along the dashed line shown in (k). (m) NHS ester-labeled mitochondrion. (n) same area as in (m), showing anti-TOM20 immunostaining and revealing the outer membrane of the mitochondrion. (o) overlay of M-N. Light scale bars show expansion-corrected values. Shaded scale bars are not corrected for the expansion factor.
Figure 1:
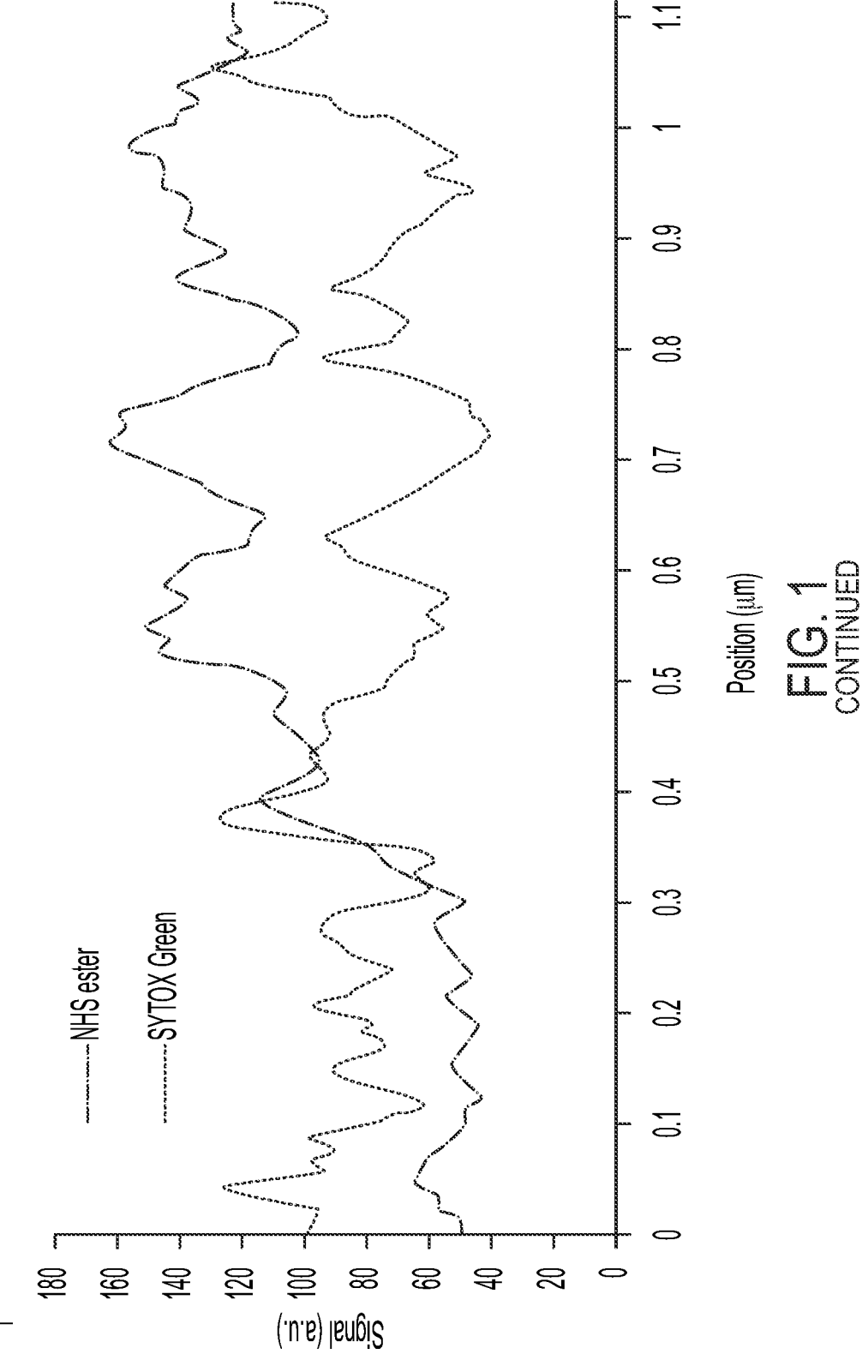
Figure 2:
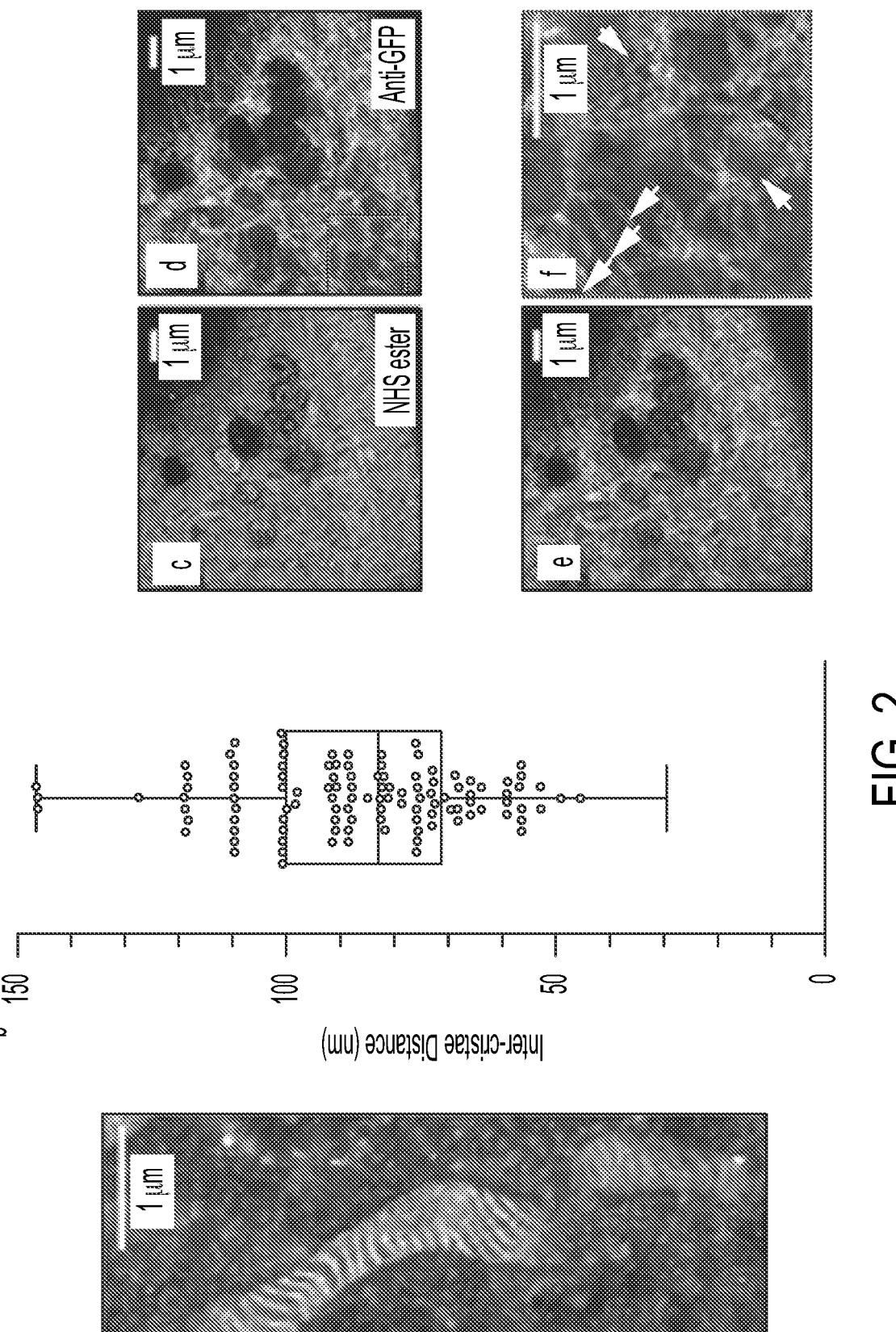
FIG. 2 are images of samples expanded through an iterative expansion technique, according to an embodiment of the claimed invention. (a) NETS-ester labeled mitochondrion in a HeLa cell revealing cristae. (b) distance distribution between neighboring cristae (n=123, N=4 experiments). (c) NHS ester channel of a HeLa cell expressing ER-membrane localized Sec61β-GFP. D), anti-GFP label in the same area revealing the ER. (e) overlay of (c)-(d). (f) zoomed-in anti-GFP image of the area denoted by the orange
Figure 3:
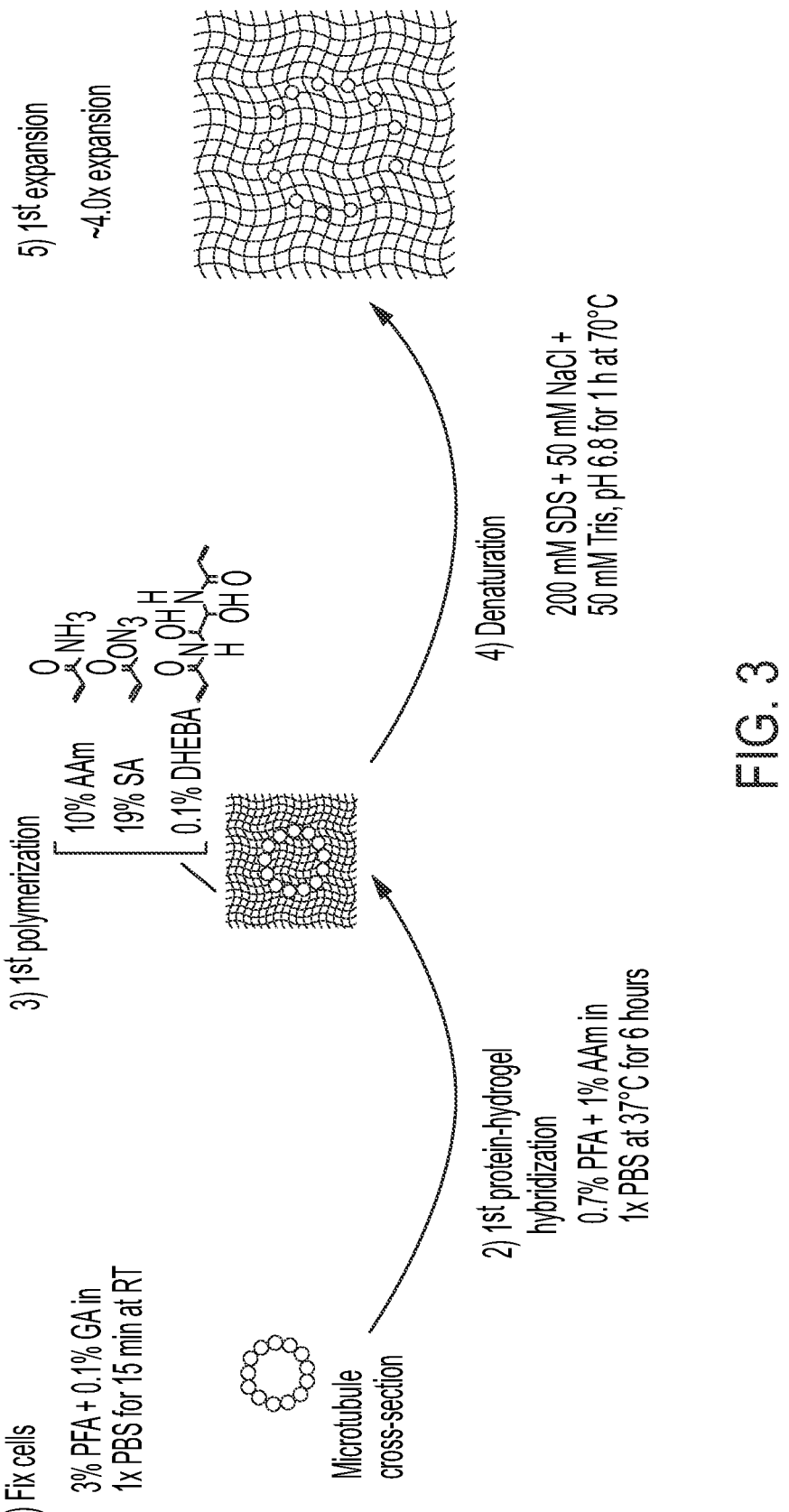
Figure 3:
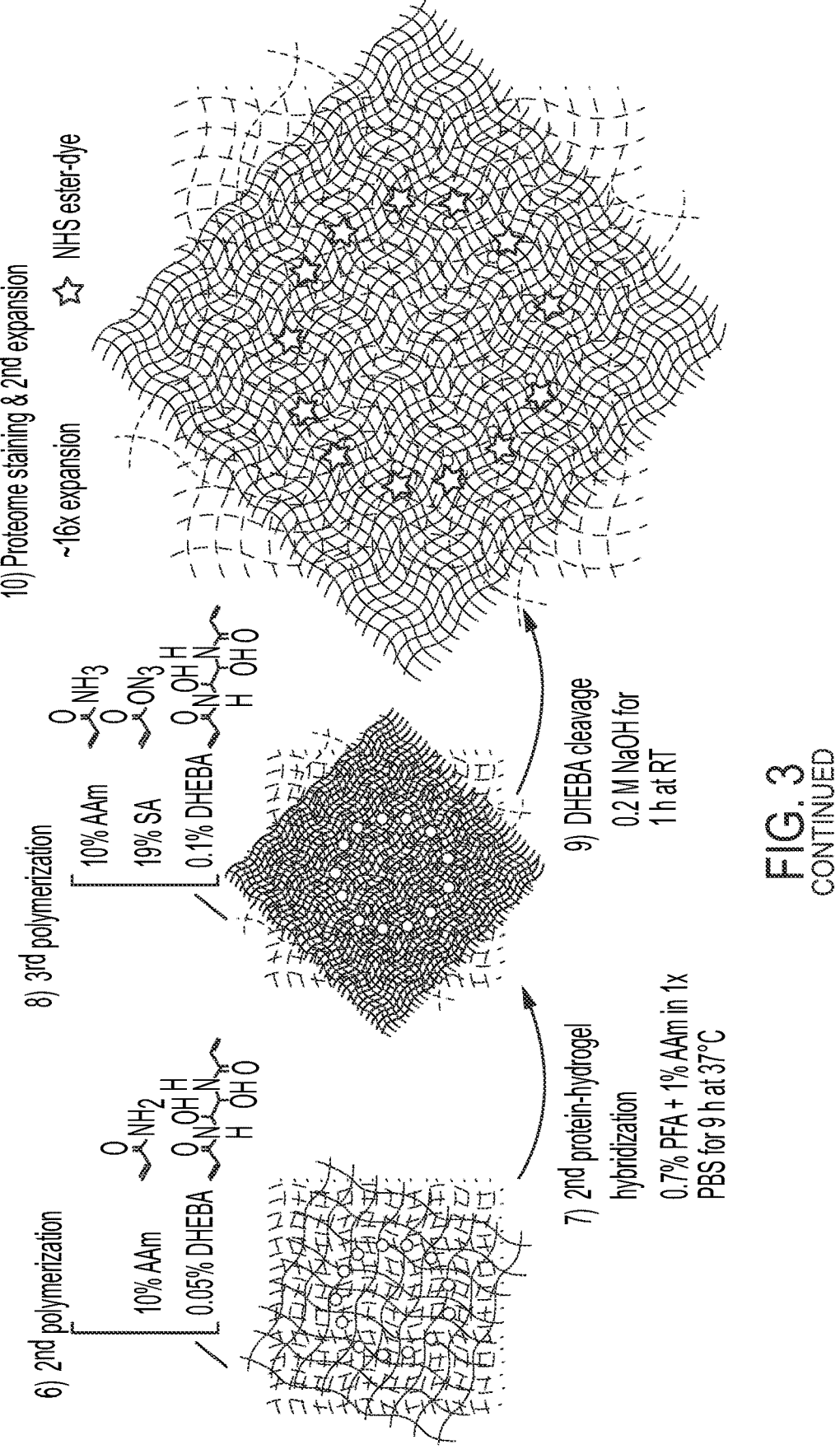

FIG. 3 depicts a schematic of sample expansion according to an embodiment of the claimed invention.

Figure 4:
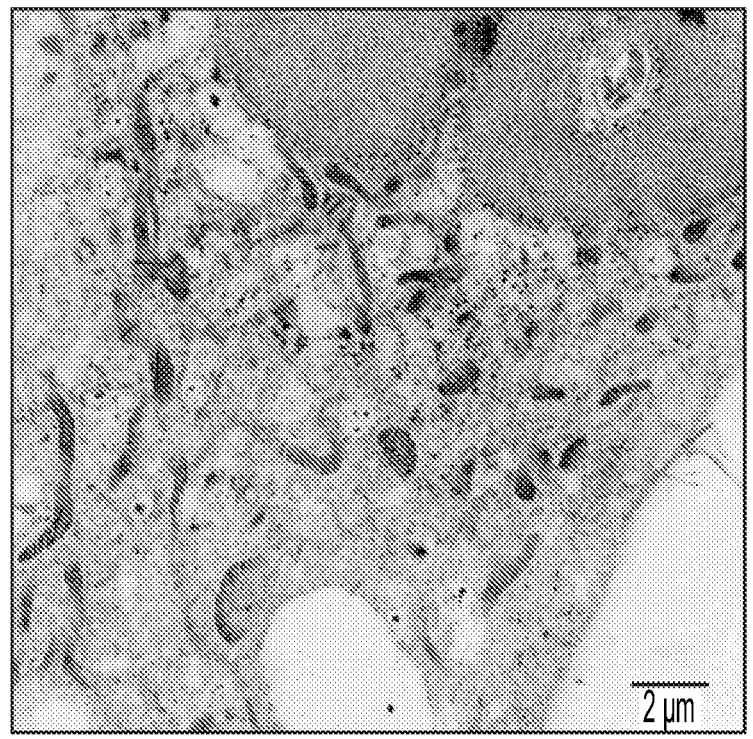

FIG. 4 is an image of a HeLa cell labeled with NHS ester displayed with an inverted color table resembling EM images.

Figure 5:
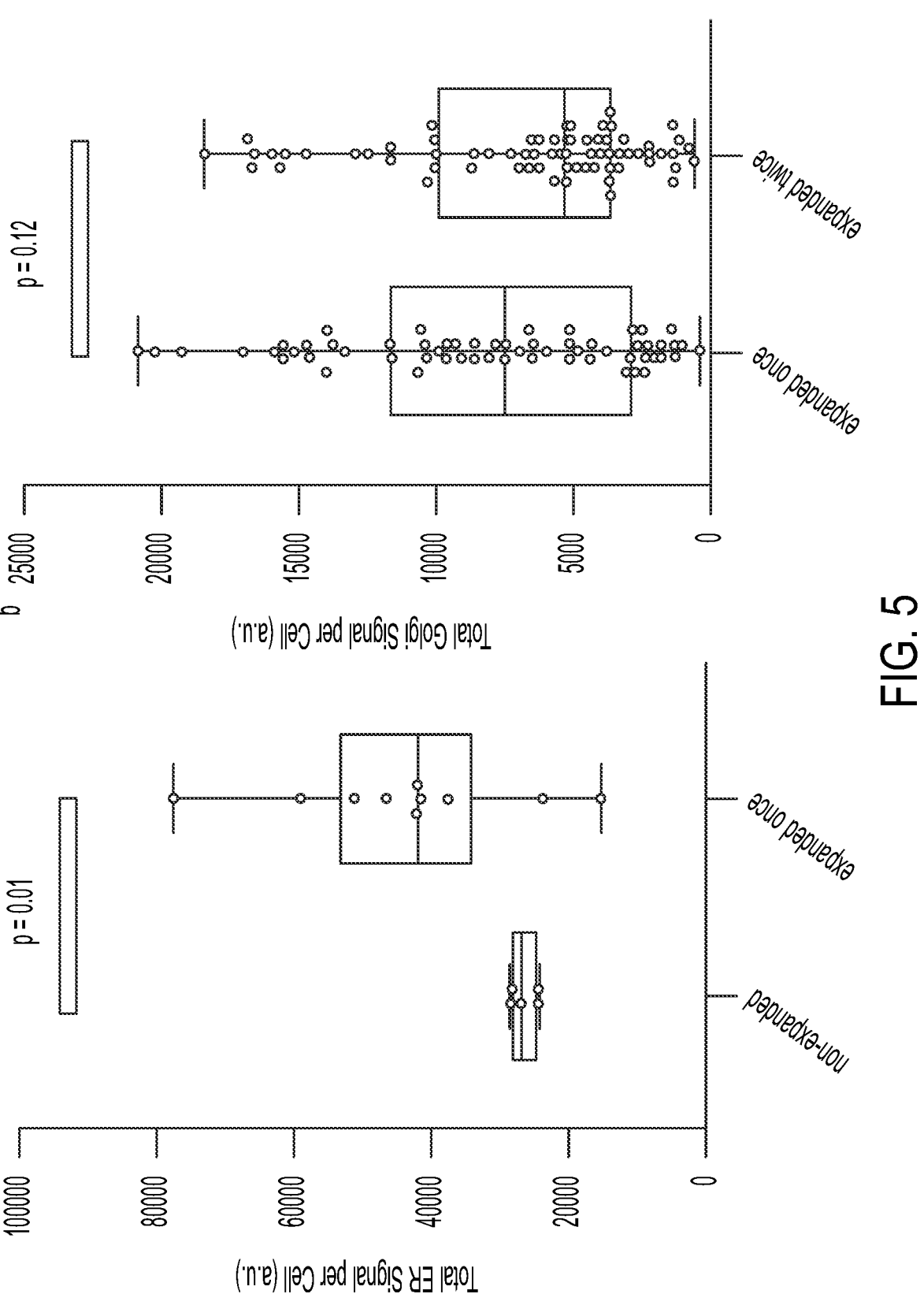

FIG. 5 depicts measurement of protein retention of samples according to an embodiment of the claimed invention. A), comparison of a non-expanded sample with a sample expanded once. (Non-expanded: n=2515 cells; Expanded once: n=294 cells.) b), comparison of a sample expanded once with a sample expanded twice. (Expanded once: n=60 cells; Expanded twice: n=67 cells.) Median and interquartile range are shown with whiskers drawn down to the minimum and maximum values.

FIG. 6 depicts a table of expansion factor results for samples according to an embodiment of the claimed invention.

FIG. 7 are images of expanded samples according to an embodiment of the claimed invention.

Figure 9:
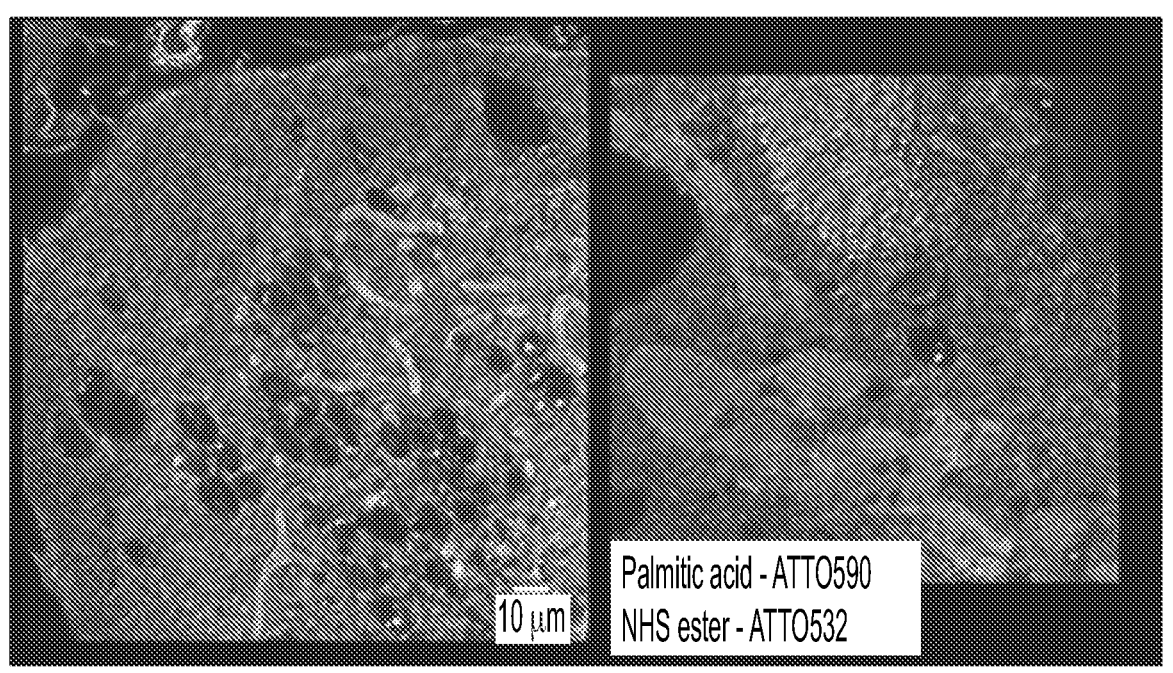
Figure 10:
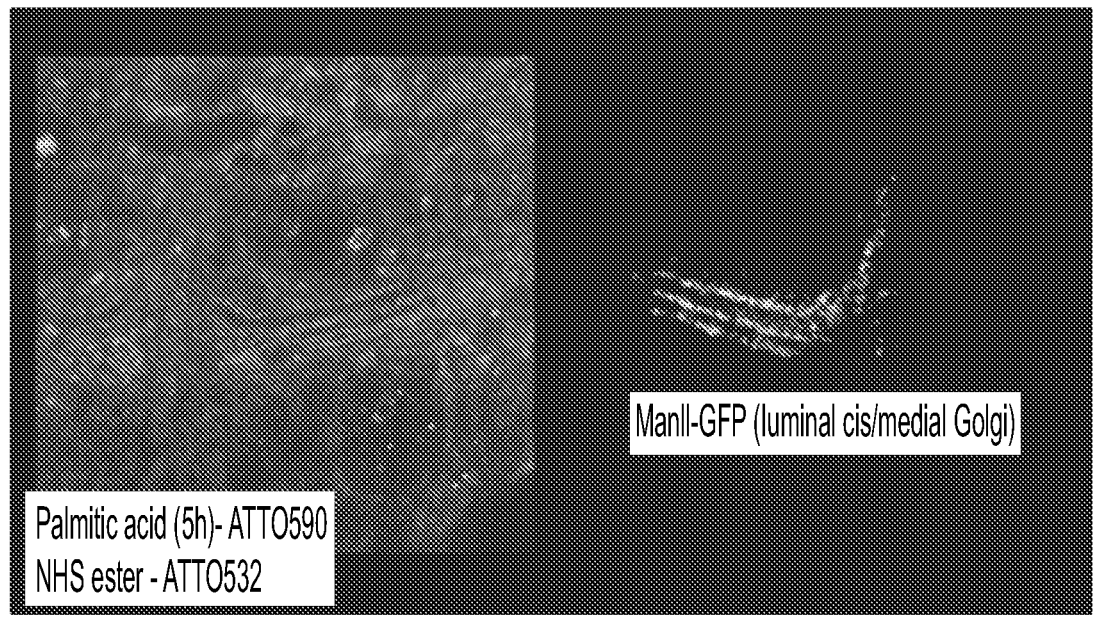

FIGS. 8-10 are images of labeled of palmitoylated proteome according to an embodiment of the claimed invention.

FIG. 11 are images of samples using different microscopy techniques according to an embodiment of the claimed invention.

FIGS. 12 and 13 are image comparisons of samples obtained with embodiments of the claimed invention (left side) with conventional microscopy images (right side).

FIGS. 14-17 are workflow processes according to embodiments of the claimed invention.

Figure 18:
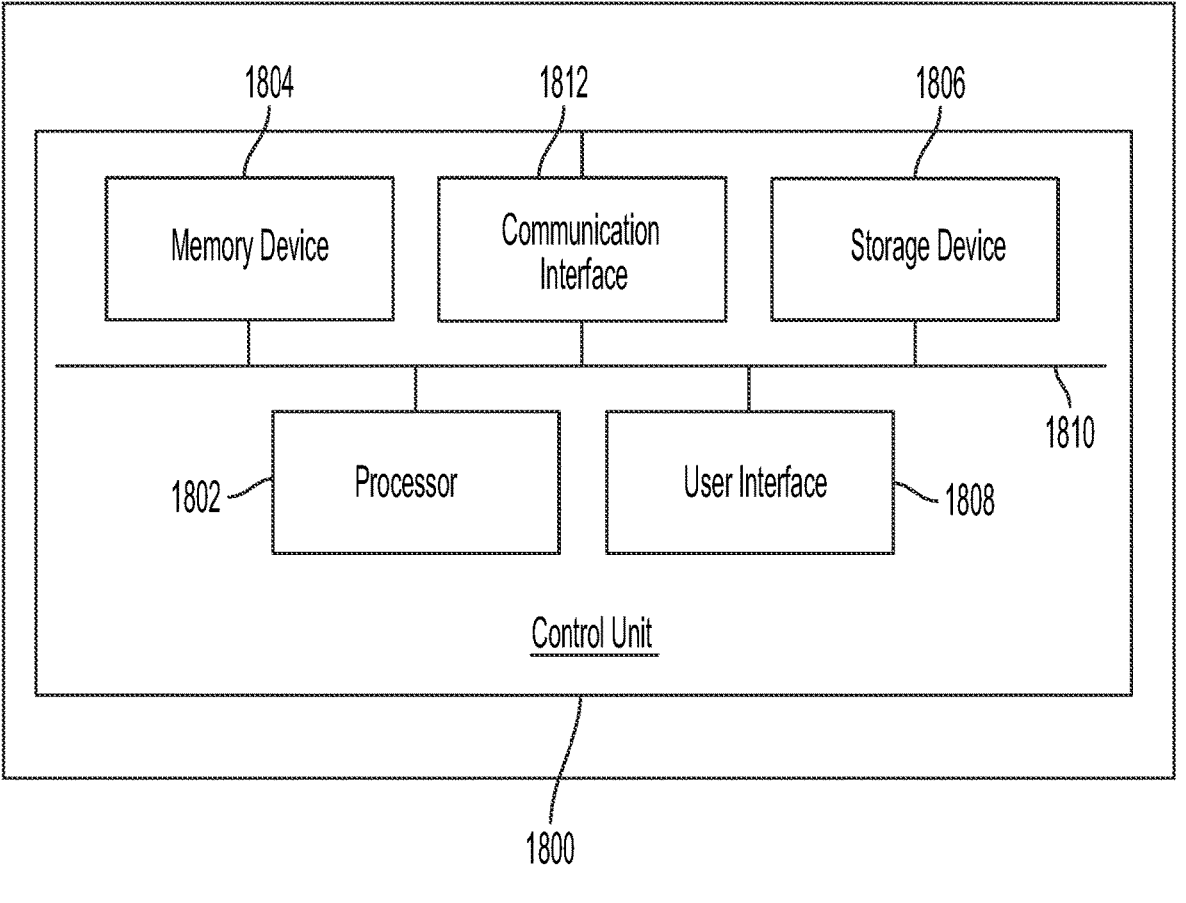

FIG. 18 illustrates a control system for sample expansion according to an embodiment of the claimed invention.

Figure 19:
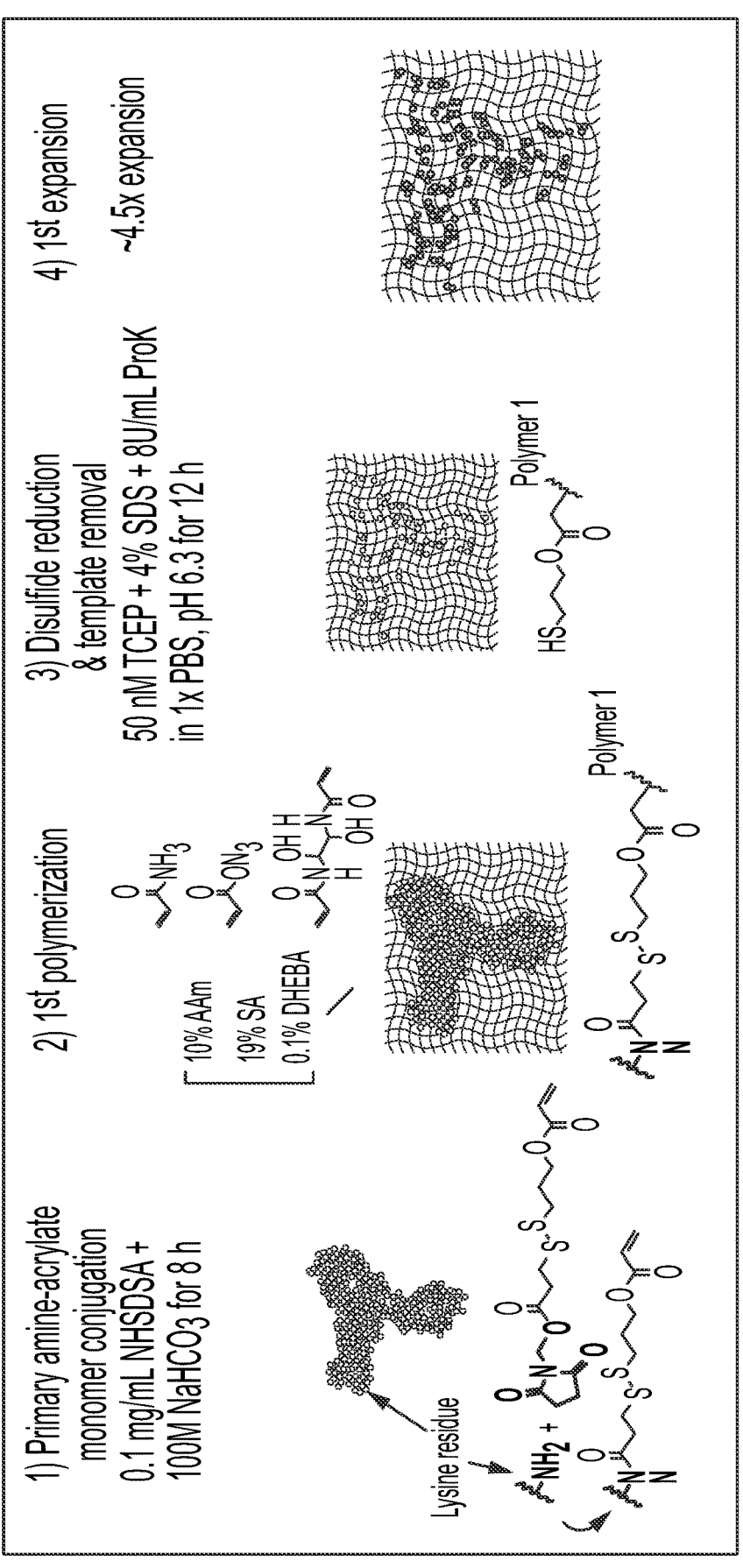
Figure 19:
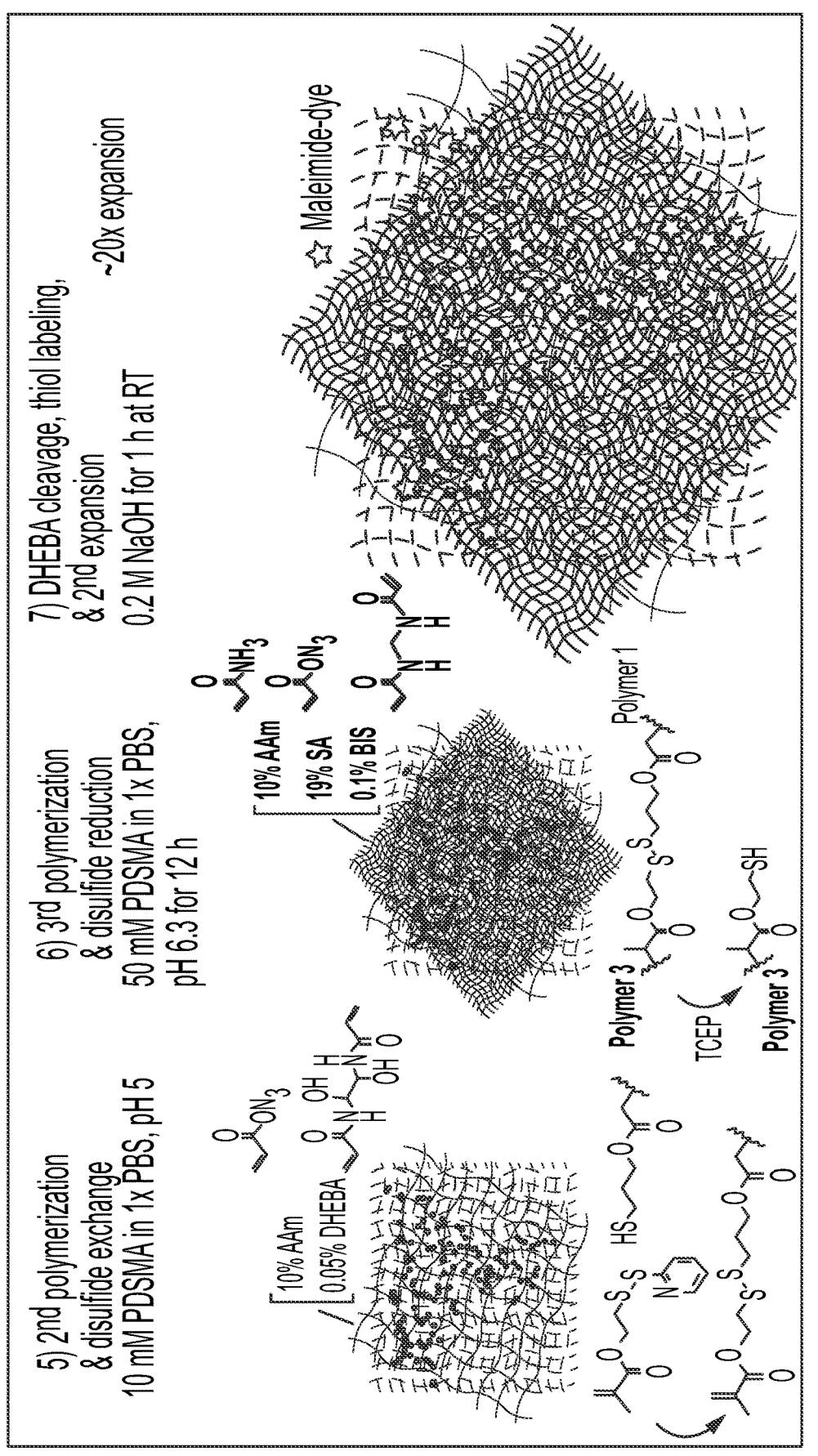

FIG. 19 illustrates a schematic for sample imprint expansion according to an embodiment of the claimed invention.

Figure 20:
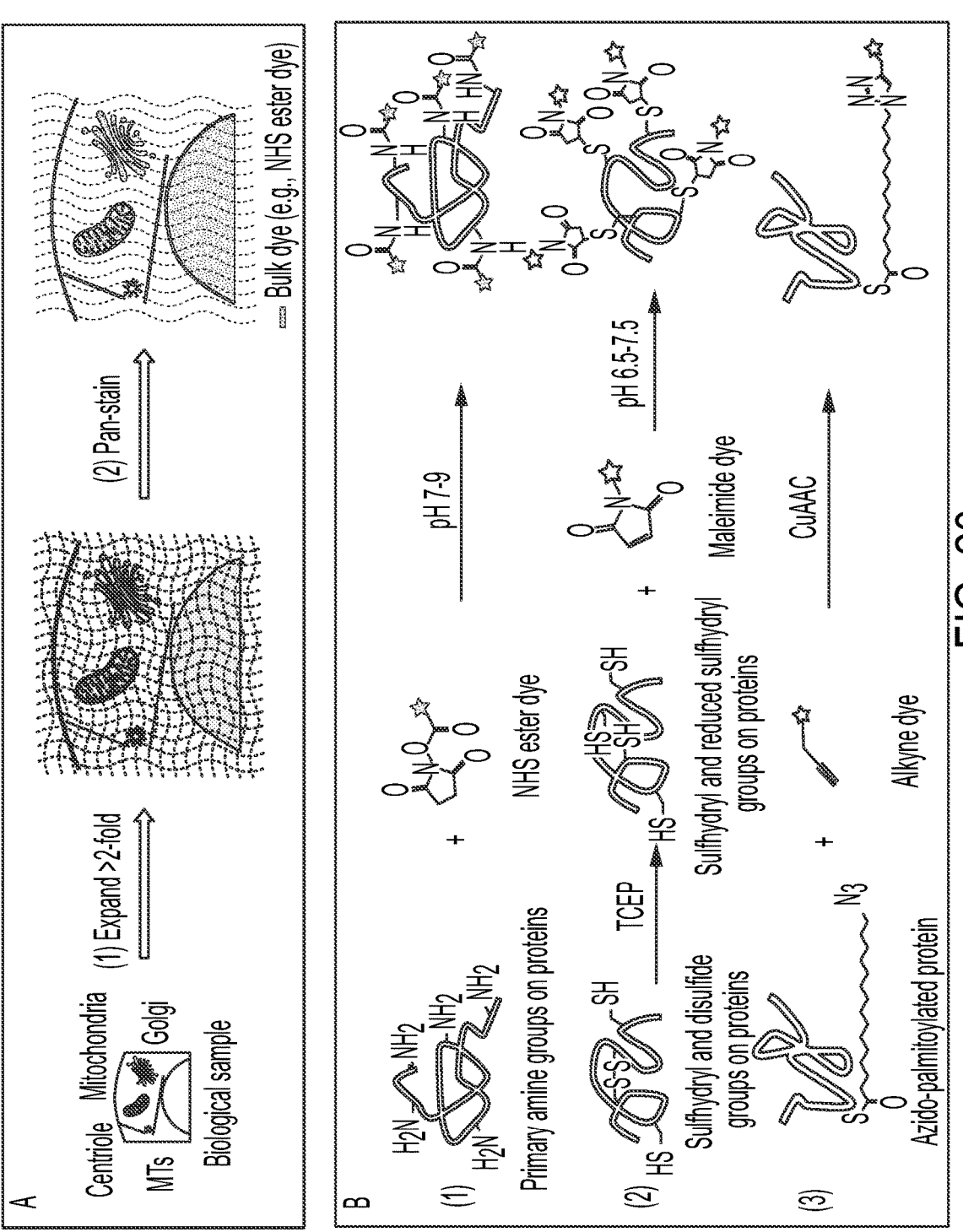

FIG. 20 is a schematic of the pan-expansion microscopy concept according to an embodiment of the claimed invention. Panel A depicts the procedure: in Step (1), the sample is physically expanded more than two-fold in every dimension. In Step (2), the sample is labeled in bulk, referred to herein as "pan-stained." Panel B depicts examples of pan-stainings: (1), reaction of primary amines (—NH2) on proteins using N-Hydroxysuccinimide (NETS) ester-conjugated dyes (star) yields proteins with stable protein-dye amide linkages. (2), reaction of sulfhydryl groups (—SH) on proteins using maleimide-conjugated dyes (star) after sample reduction with tris(2-carboxyethyl)phosphine (TCEP) yields proteins with stable protein-dye thioether linkages. (3), copper-catalyzed azide/alkyne cycloaddition (CuAAC) reaction of azido palmitoylated proteins with alkyne-conjugated dyes (star) yields proteins with stable triazole linkages.

Figure 21:
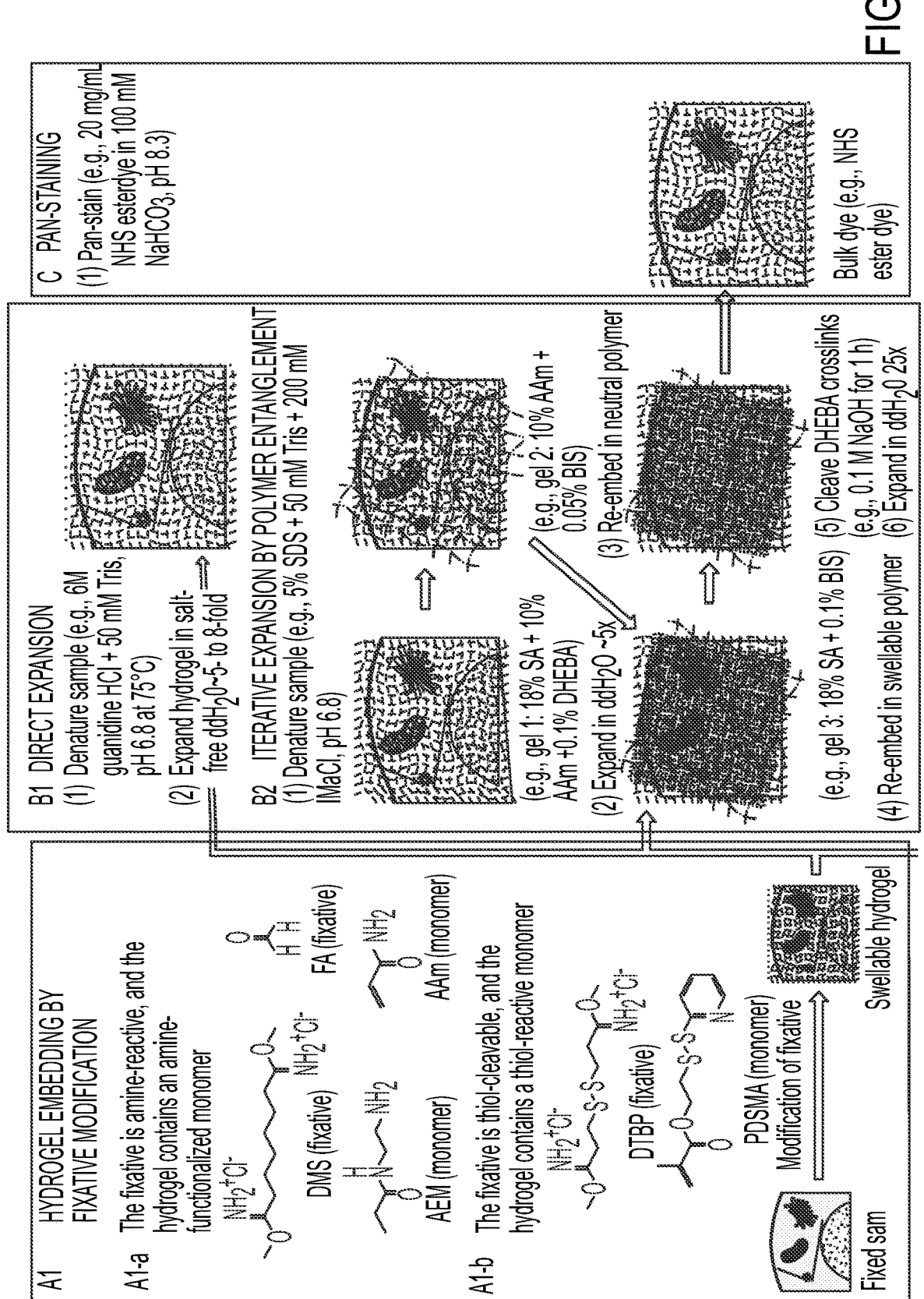
Figure 21:
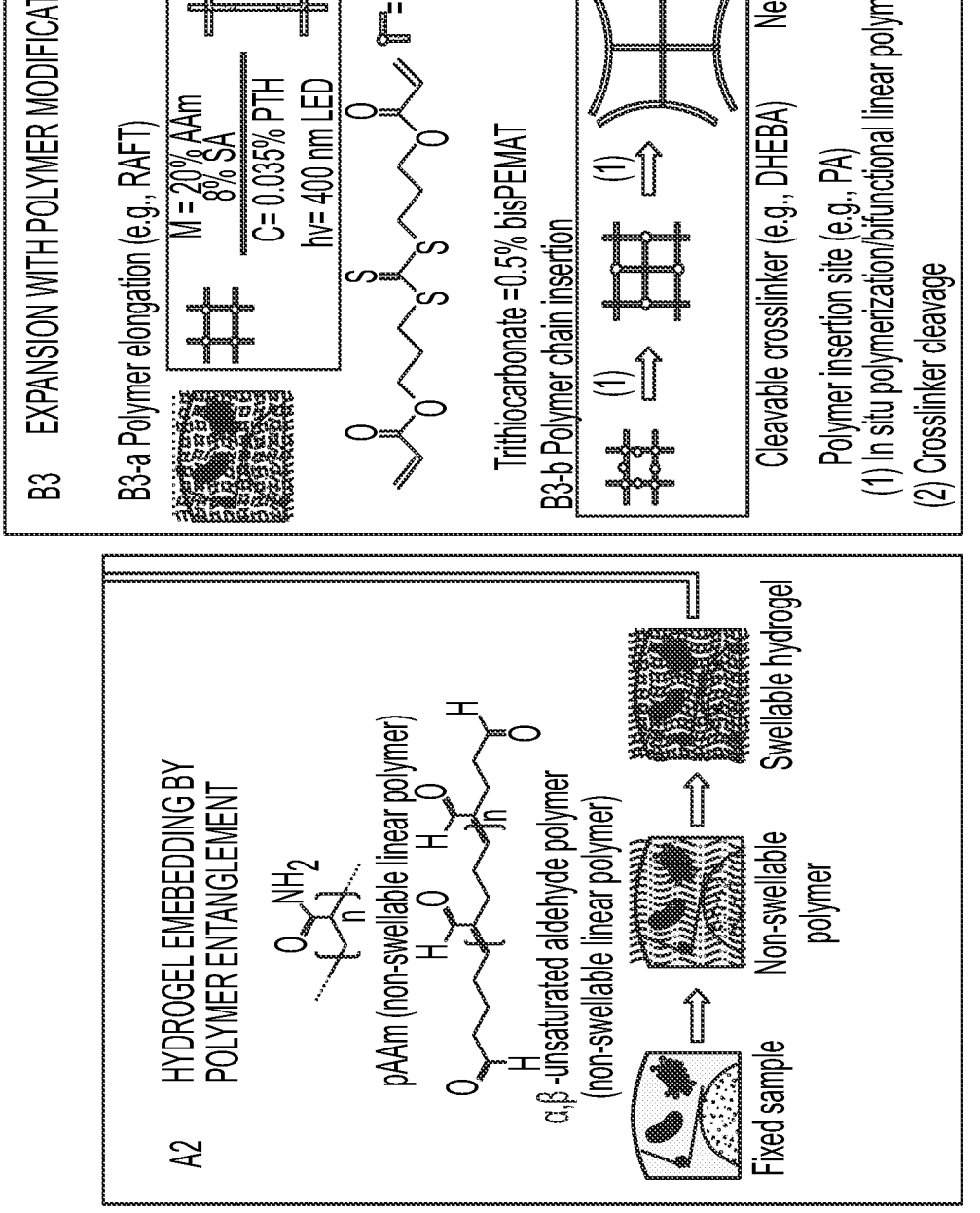

FIG. 21 is a schematic of pan-expansion microscopy protocols according to embodiments of the claimed invention. Panels A1-A2 depict two distinct sample-hydrogel embedding procedures. In Panel A1, the sample is first chemically fixed and then embedded in a hydrogel containing fixative-modifying monomers. In Panel A1-*a*, the sample is fixed with an amine-reactive fixative (e.g., 4% formaldehyde (FA) or 2% FA+2% dimethyl suberimidate (DMS)) and then embedded in swellable hydrogel containing an amine-functionalized monomer (e.g., 10% acrylamide (AAm) or 0.1% N-(2-aminoethyl)acrylamide hydrochloride (AEM) added to a hydrogel monomer solution of 20% sodium acrylate (SA) and 0.1% N,N'-methylenebis(acrylamide) (BIS)). In Panel A1-*b*, the sample is fixed with a thiol-cleavable fixative (e.g., 2% FA+0.5% dimethyl dithiobispropionimidate (DTBP)) and then embedded in a swellable hydrogel containing a thiol-reactive monomer (e.g., 1% pyridyl disulfide ethyl methacrylate (PDSMA) added to a hydrogel monomer solution of 20% sodium acrylate (SA) and 0.1% N,N'-methylenebis(acrylamide) (BIS)). In Panel A2, the sample is first embedded in a non-swellable polymer, which can be linear (e.g., 15% polyacrylamide (pAAm) or 0.2% a,b-unsaturated aldehyde polymer) or crosslinked (e.g., 15% pAAm+0.005% BIS or 15% pAAm+0.05% N,N'-(1,2-dihydroxythylene)bisacrylamide) (DHEBA)) and then embedded in a swellable hydrogel (e.g. 10% AAm+20% SA+0.1% BIS for 5-fold expansion or 10% AAm+18% SA+0.01% piperazine diacrylamide (PDA) for 8-fold expansion) such that the majority of the sample components is retained by entanglement of the non-swellable polymer with the swellable hydrogel. Panels B1-B3 depict three distinct sample expansion mechanisms that proceed sample denaturation. Sample homogenization can take many forms. It can be in the form of detergent and heat denaturation (e.g., 5% sodium dodecyl sulfate (SDS)+50 mM tris(hydroxymethyl)aminomethane (Tris)+200 mM NaCl, pH 6.8 at 75° C.) or chaotropic and heat denaturation (e.g., 6 M guanidine HCl+50 mM Tris, pH 6.8 at 75° C.). In Panel B1, the hydrogels from Panels A1-A2 are denatured and directly expanded in deionized water without further modifications. In Panel B2, the hydrogels from Panels A1-A2 are denatured and expanded iteratively to achieve a higher expansion factor. Loss of sample components is minimal because the sample is retained by polymer entanglements of the re-embedment gels. In more detail, the ~5-fold expanded hydrogel (synthesized with a cleavable crosslinker such as DHEBA) is re-embedded in a neutral hydrogel (e.g., 10% AAm+0.05% DHEBA) to hold it in its expanded form and re-embedded again in a swellable hydrogel (e.g., 10% AAm+20% SA+0.1% BIS). The crosslinks of the first and second hydrogels are cleaved to allow the second swellable hydrogel to expand another factor of ~5 for a total sample expansion of ~25-fold. In Panel B3, the hydrogel with the embedded sample is denatured and modified chemically such that it grows in polymer content and size. In Panel B3-*a*, this modification is in the form of polymer chain elongation. The polymer chains of the hydrogel are crosslinked with a trithiocarbonate (e.g., 0.5% bis [(2-propionate)ethyl methacrylate] trithiocarbonate (bis-PEMAT); orange dot) and elongated by reversible addition-fragmentation chain-transfer (RAFT) polymerization of hydrophilic monomers (M; where M=20% AAm+8% SA).

This polymerization reaction occurs in presence of a photocatalyst (C; where C=0.035% phenothiazine (PTH)) and is exposed to 400 nm LED light irradiation in a de-oxygenated environment for over 6 h. The resulting modified hydrogel is larger in size in the original hydrogel and its expansion factor is dependent on the nature and concentrations of chosen monomers as well as the conversion rate of the polymerization reaction. In Panel B3-*b*, polymer network modification is in the form of polymer chain insertion. In this example, the sample-embedded hydrogel is crosslinked with a cleavable crosslinker (e.g. N,N'-(1,2-dihydroxyethylene)bisacrylamide (DHEBA); light blue dot) and synthesized with latent polymer insertion sites (e.g. the clickable monomer propargyl acrylate (PA); orange dot). In Step (1), the latent polymer insertion site is either converted to a polymerizable molecule, via click reaction with an azide-acrylate (e.g., azide-PEG-acrylate), or left intact. In Step (2), in the case of polymer insertion by in situ polymerization, the polymer insertion sites are rendered polymerizable and the hydrogel is incubated in a solution of monomers (e.g., 10% AAm+10% SA) which are polymerized with the polymerizable insertion sites in situ. In the case of bifunctional linear polymer insertion, the insertion sites are left intact, and a bifunctional linear polymer (e.g., a poly(acrylamide-co-acrylic acid) polymer with two azido groups at each extremity) is used to insert new polymer chains in the hydrogel. In both cases, after polymer chain insertion, the crosslinks of the original hydrogel are cleaved, and the modified hydrogel is allowed to extend in water. In Panel C, the expanded hydrogels from Panels B1-B3 are pan-stained (e.g., using 20 mg/mL N-hydroxysuccinimide (NHS) ester dye in 100 mM NaHCO$_3$) and washed with deionized water to achieve maximum sample expansion.

FIG. 22 depicts the mechanism of iterative expansion by polymer entanglement according to an embodiment of the claimed invention. Panel A shows schematic of two proteins embedded in first expansion gel before sample denaturation and expansion. The dot represents acrylamide monomer modification of the sample fixative. Panel B depicts a schematic of proteins denatured and expanded in the first expansion hydrogel. Panel C depicts a schematic representing dissolution of the first expansion hydrogel: base hydrolysis of N,N'-(1,2-dihydroxyethylene)bisacrylamide (DHEBA) converts the crosslinked first expansion hydrogel network (dotted box) into long and linear polymer chains capable of forming entanglements. Panel D shows a schematic of proteins embedded in the final expansion hydrogel after the first expansion and re-embedding in a neutral polyacrylamide hydrogel (not drawn for simplicity). Panel E depicts a schematic of a protein-polymer hybrid entangled in final expansion gel after crosslinker dissolution of the first expansion gel. Panel F illustrates the definition of polymer entanglement: a polymer chain is likely entangled if it crosses an arbitrary plane 3 times (asterisks).

Figure 23:
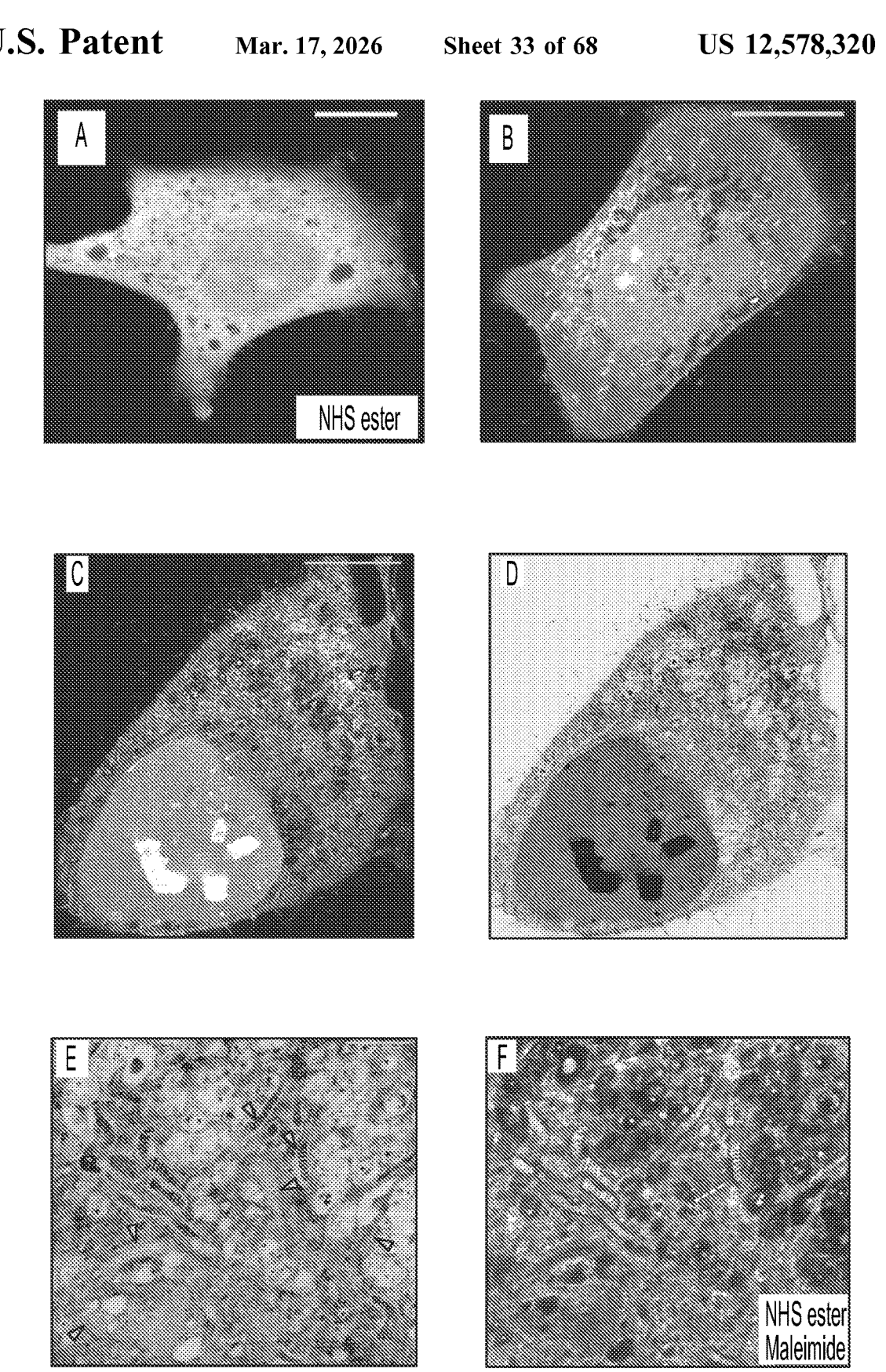
Figure 23:
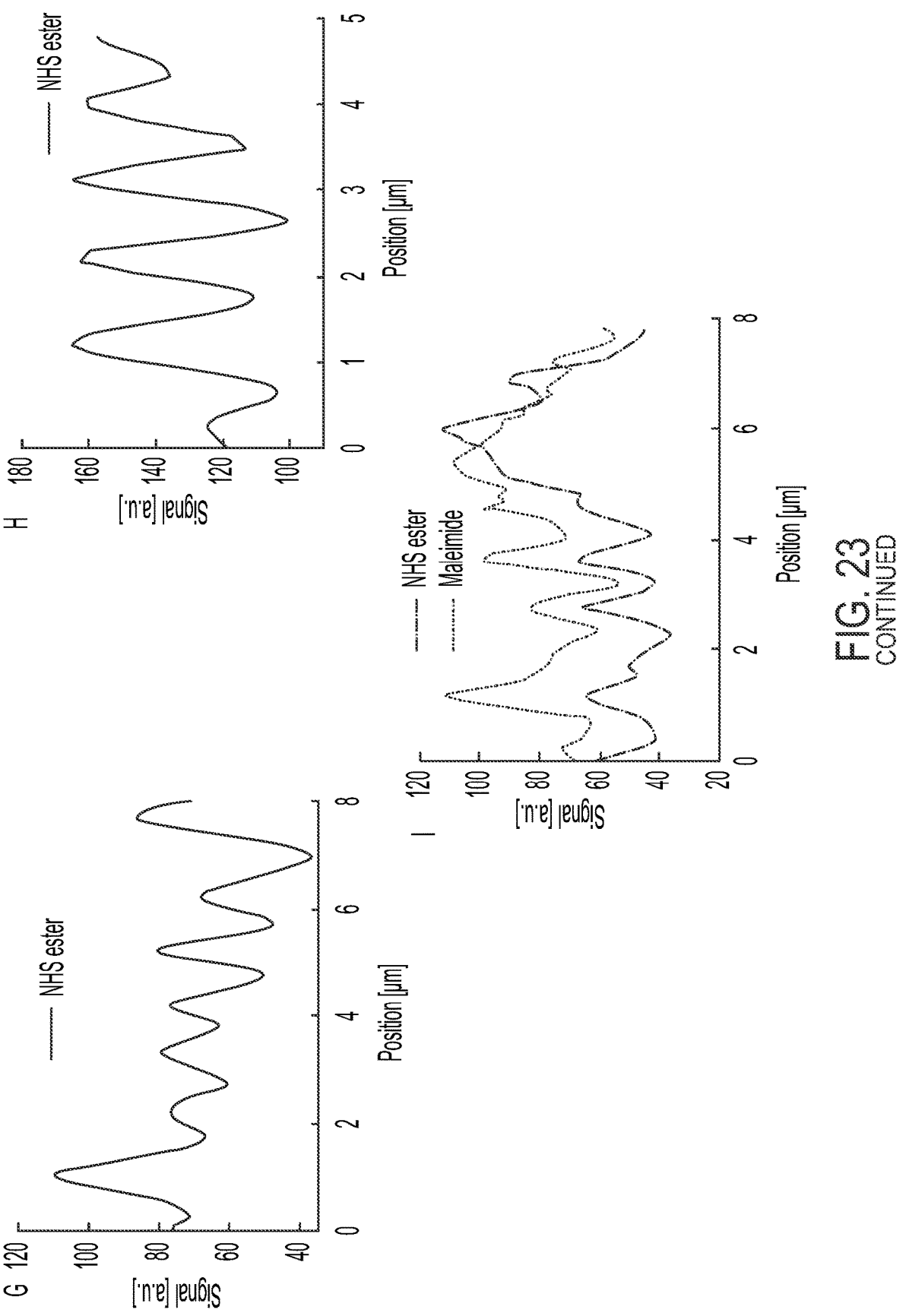

FIG. 23 are images of samples expanded through a pan-expansion technique showing EM-like cellular ultrastructure, according to an embodiment of the claimed invention. Panel A depicts a non-expanded HeLa cell pan-stained with NHS ester dye. Panel B depicts a HeLa cell expanded 4-fold and pan-stained with NHS ester dye. Panel C depicts a pan-ExM expanded HeLa cell pan-stained with NHS ester dye. Panel D depicts the same image as C but shown with an inverted color table. Panel E depicts the area in the box in D reveals hallmark cellular ultrastructure features such as mitochondrial cristae (two top right arrowheads) and Golgi cisternae (remaining arrowheads). Panel F, same image as in E but showing overlay of NHS ester pan-stain channel and maleimide pan-stain channel. Representative images from 3 (A, B) and 11 (C-F) independent experiments are shown. Panel G depicts a line profile along the bottom left dashed line in Panel E revealing Golgi cisternae. Panel H depicts a line profile along the middle dashed line in Panel E revealing mitochondrial cristae. Panel I depicts a line profile along the dashed line in Panel F revealing the change in NHS ester to maleimide staining across a Golgi stack. Panels A-C are displayed with a black-to-white color table. Panels D and E are displayed with a white-to-black color table. Top right scale bars are not corrected for the expansion factor. Scale bars, (A) 10 μm, (B) 40 μm, (C, D) 100 μm, (E, F) 20 μm.

Figure 24:
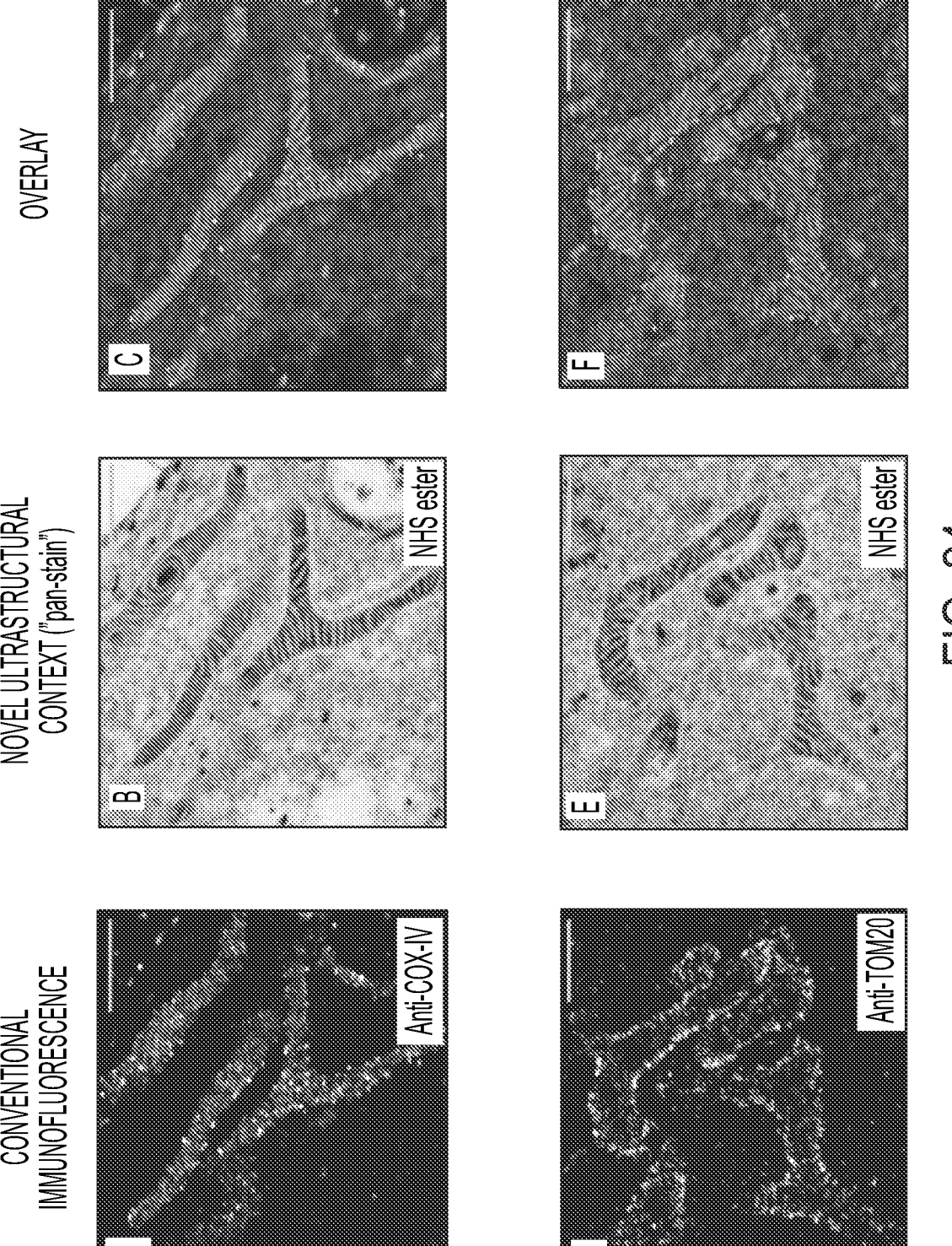

FIG. 24 are images of samples expanded through a pan-expansion technique showing conventional immunofluorescence images of mitochondria overlaid with novel EM-like contextual image, according to an embodiment of the claimed invention. Panel A depicts an anti-COX-IV immunostaining of a mitochondrion. Panel B depicts the same area as in Panel A, showing NHS ester pan-stained HeLa cell. Panel C depicts an overlay of Panels A and B revealing COX-IV localization in the inner membrane of mitochondria. Panel D depicts an anti-TOM20 immunostaining of a mitochondrion. Panel E depicts the same area as in Panel D showing NHS ester pan-stained HeLa cell. Panel F depicts an overlay of Panels D and E revealing that TOM20 is localized on the outer membrane mitochondria. Top right scale bars are not corrected for the expansion factor. Scale bars, (A-C) 15 μm, (D-F) 10 μm.

FIG. 25 are images of samples expanded through a pan-expansion technique showing conventional Golgi immunofluorescence images overlaid with novel EM-like contextual image, according to an embodiment of the claimed invention. Panels A and D depict anti-GFP Golgi immunostaining revealing distinct Golgi cisternae. Panels B and E, same areas as in A and D, showing NHS ester pan-stained HeLa cell, revealing ultrastructural context (e.g., mitochondria, Golgi cisternae, NPCs, nucleus, nucleoli, vacuoles). Panels C and F, overlay images. Top right scale bars are not corrected for the expansion factor. Scale bars, (A-C) 45 μm, (D-F) 20 μm.

Figure 26:
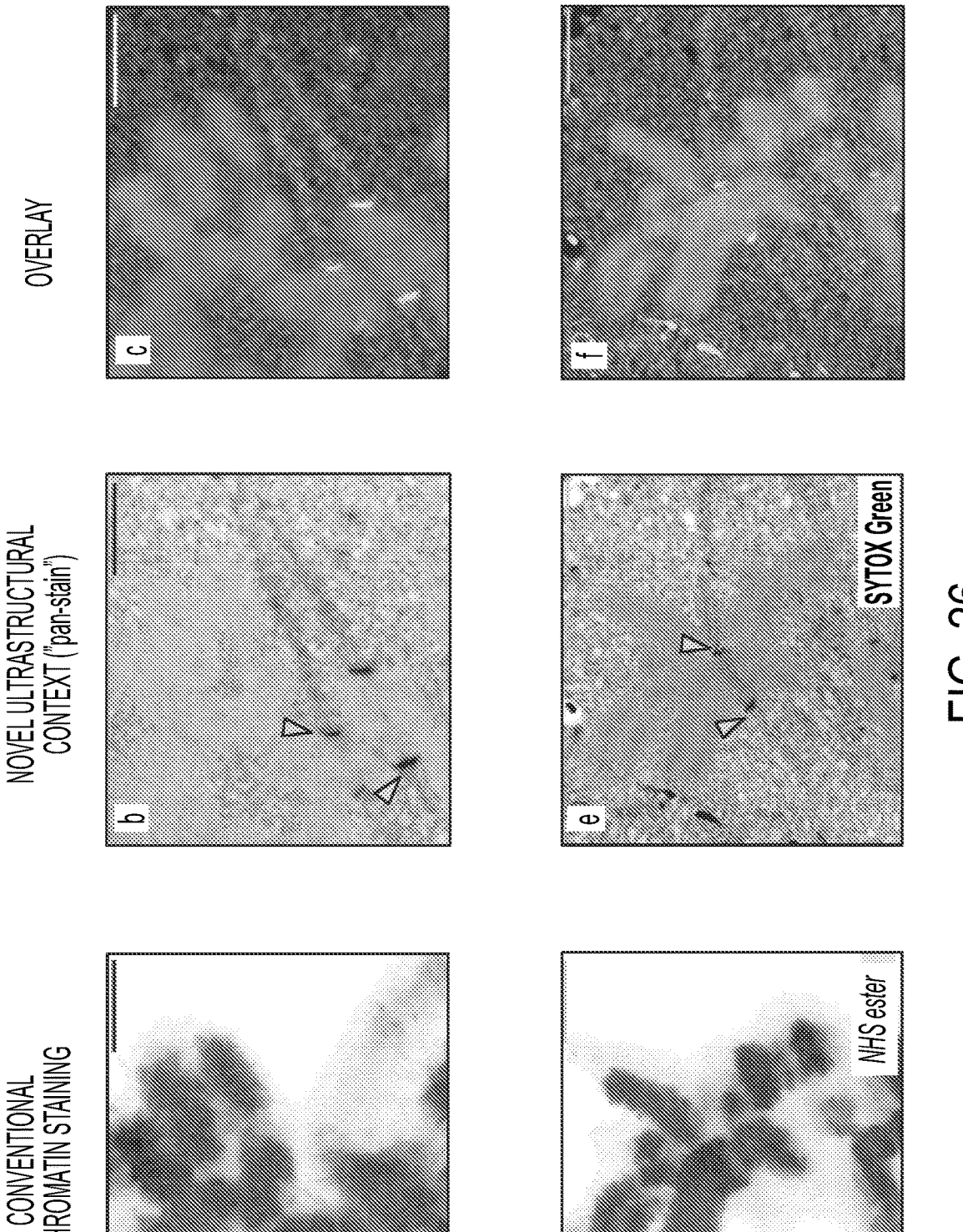

FIG. 26 are images of samples expanded through a pan-expansion technique showing conventional chromosome staining overlaid with novel EM-like contextual image, according to an embodiment of the claimed invention. Panels A and D depict SYTOX Green staining showing chromosomes. Panel B and E depict NHS ester pan-stained HeLa cell showing protein-dense microtubule bundles and kinetochores. Panels C and F depict overlaid images of Panels A and B, and Panels D and E, respectively. Scale bars are corrected for the expansion factor. Scale bars, (A-C) 1 μm, (D-F) 1.5 μm.

Figure 27:
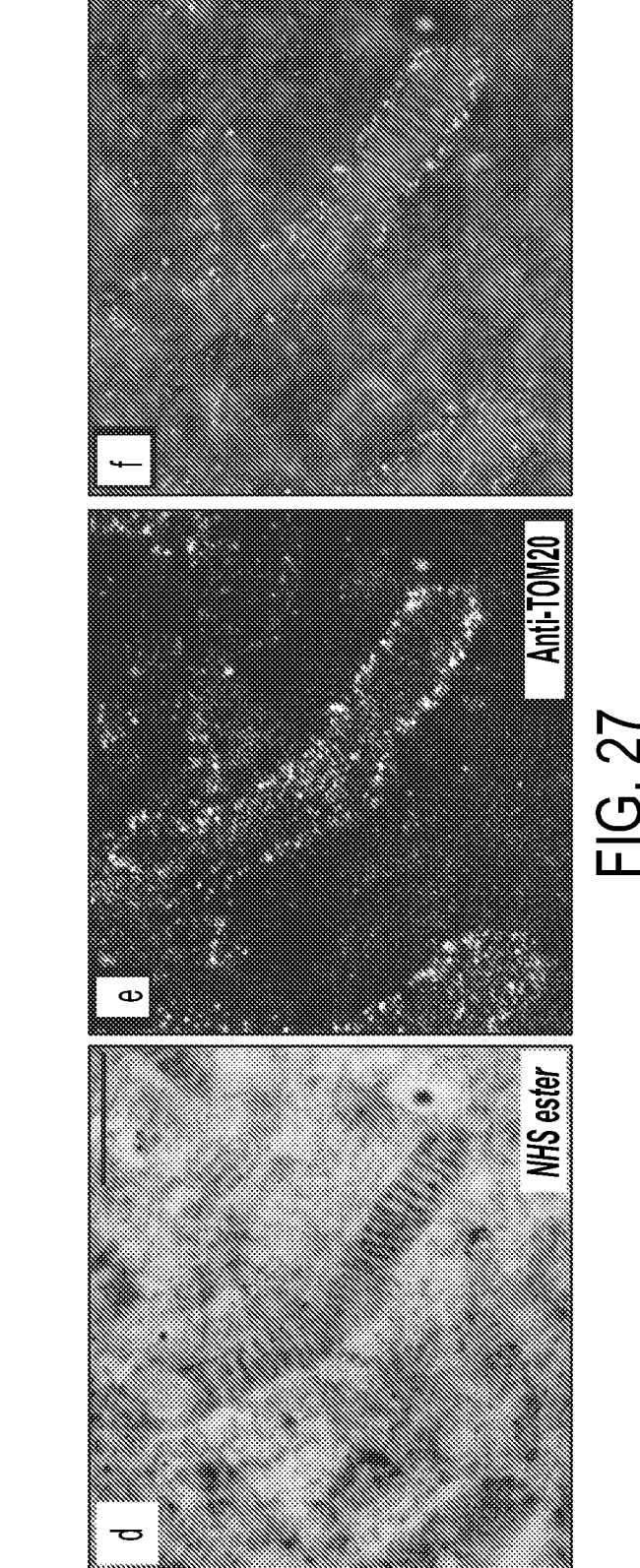
Figure 27:
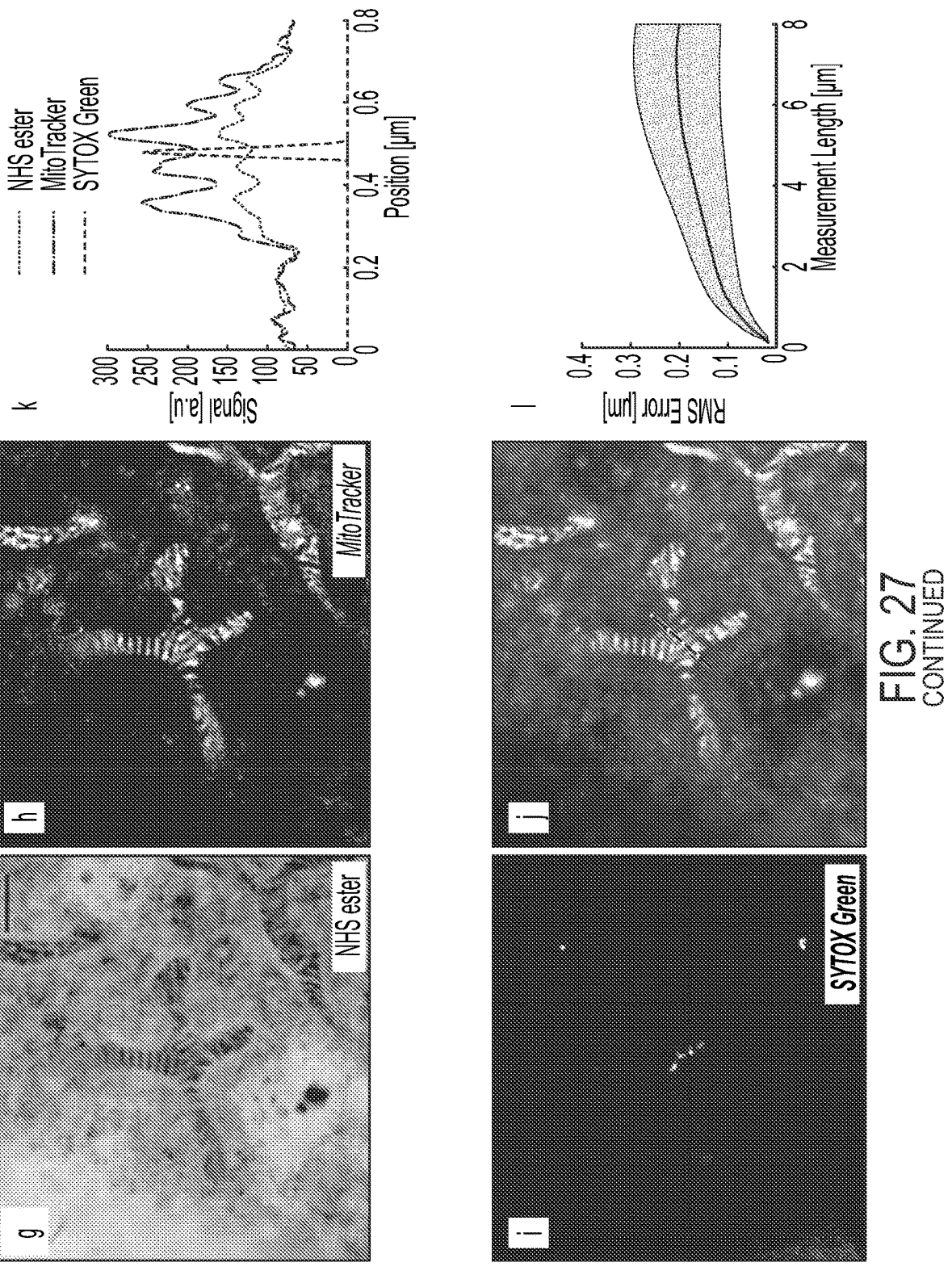

FIG. 27 depict images of samples expanded through a pan-expansion technique, showing specific proteins in the context of cellular ultrastructure, according to an embodiment of the claimed invention. Panel A depicts NHS ester pan-stained HeLa cell. Panel B depicts anti-α-tubulin immunostaining in the same area. Panel C depicts an overlay of Panels A and B. Panel D depicts NHS ester pan-stained mitochondrion. Panel E the same area as in Panel D, showing anti-TOM20 immunostaining and revealing the outer membrane of the mitochondrion. Panel F depicts an overlay of Panels D and E. Panel G depicts NHS ester pan-stained mitochondrion. Panel H depicts MitoTracker Orange stain in the same area as Panel G. Panel I depicts SYTOX Green stain showing DNA in mitochondrial nucleoids. Panel J depicts an overlay of Panels G-I. Panel K depicts a line profile along the dashed line shown in Panel J. Representative images from 3 (A-F) and 5 (G-J) independent experiments are shown. Panel L depicts a plot of root mean square (RMS) error over distance comparing pre- and post-pan-ExM images of microtubules (n=5 cells). The line corresponds to the mean and error bars correspond to the standard deviation. Panels A, D, and G are displayed with a white-to-black color table. Panels B, E, H, and I are displayed with a black-to-white color table. Scale bars show expansion-corrected values. Scale bars, (A-C) 2 μm, (D-F) 1 μm, (G-J) 500 nm.

Figure 28:
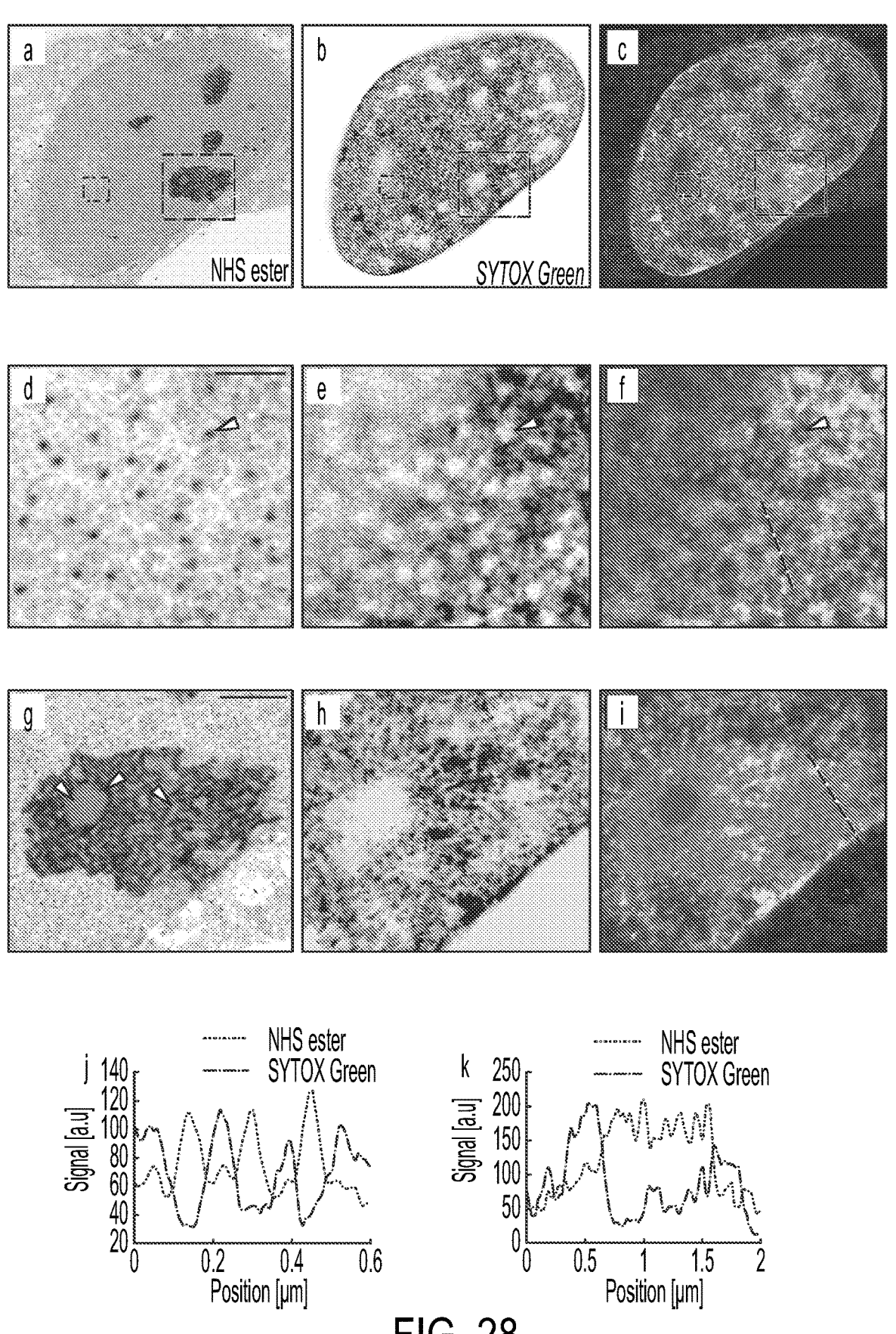

FIG. 28 are images of nuclear ultrastructure through a pan-expansion technique, according to an embodiment of the claimed invention. Panel A depicts an image of NHS ester pan-stained U-2OS cell in interphase. Panel B depicts a SYTOX Green nucleic acid stain image of the same area of Panel A. Panel C depicts an overlay of Panels A and B. Panels D-F depict magnified views of the areas outlined by the boxes in Panels A-C, respectively, showing amine-rich regions corresponding to nuclear pore complexes (NPCs) which coincide with circular channels excluding chromatin in the SYTOX Green image. The arrowheads point at one NPC and the corresponding chromatin channel. Panels G-I depict magnified views of the areas outlined by the green boxes in A-C, respectively, showing ultrastructural details of a nucleolus. The arrowheads point (from left to right) at the fibrillar center (FC), the dense fibrillar component (DFC) and the granular component (GC), respectively. Representative images from 5 (A-I) independent experiments are shown. Panel J depicts a line profile along the dashed line shown in Panel F. Panel K depicts a line profile along the dashed line shown in Panel I. Panels A, B, D, E, G, and H are displayed with a white-to-black color table. All scale bars are corrected for the determined expansion factor. Scale bars, (A-C) 5 μm, (D-F) 250 nm, (G-I), 1 μm.

FIG. 29 are images of mitotic ultrastructure expanded through a pan-expansion technique, according to an embodiment of the claimed invention. Panel A depicts SYTOX Green channel of a mitotic U-2OS cell revealing chromosomes. Panel B depicts anti-α-tubulin immunostaining in the same area as Panel A. Panel C depicts NHS ester pan-staining in the same area as Panels A and B. Panel D depicts an overlay of Panels A-C. Panel E depicts a magnified image of the area outlined by the box in Panel C. Panel F depicts a magnified image of the area outlined by the box in Panel D. The right-most arrowheads highlight individual microtubules within microtubule bundles, and the left-most arrowheads point at kinetochores. Representative images from 3 (A-F) independent experiments. Panel G depicts a line profile along the dashed line shown in Panel E. Panel H depicts a line profile along the dashed line shown in Panel F. Panels A, C, and E are displayed with a white-to-black color table. Panel B is displayed with a black-to-white color table. All scale bars are corrected for the determined expansion factor. Scale bars, (A-D) 2 μm, (E, F) 300 nm.

FIG. 30 depicts images of centrosome ultrastructure expanded through a pan-expansion technique, according to an embodiment of the claimed invention. Panel A depicts a lateral view of a NETS-ester pan-labeled mature centriole in a pan-ExM processed U-2OS cell revealing subdistal appendages (arrowhead). Panel B depicts anti-polyglutamate chain (polyE) immunostaining in the same area as Panel A revealing three distinct polyglutamylated microtubule triplets. Panel C depicts an overlay of Panels A and B. Panel D depicts an axial view of a different NETS-ester pan-stained mature centriole revealing microtubule triplets (top arrowhead) and pericentriolar material (PCM) (bottom arrowhead). Representative images from 4 (A, D) and 1 (B, C) independent experiments. Panels A, B, and D are displayed with white-to-black color tables. All scale bars are corrected for the determined expansion factor. Scale bars, (A-C) 200 nm, (D) 100 nm.

FIG. 31 are images of organelle ultrastructure expanded through a pan-expansion technique, according to an embodiment of the claimed invention. Panel A depicts NHS ester pan-stained mitochondrion in a NHS ester pan-stained HeLa cell. Panel B depicts NHS ester pan-stained HeLa cell expressing ER-membrane localized Sec61β-GFP. Panel C depicts anti-GFP label in the same area of Panel B revealing the ER. Panel D depicts an overlay of Panels A and B. Panel E depicts a magnified image of the area outlined by the box in Panel B, revealing individual ER tubules clearly resolved as hollow tubules (left-most arrowheads) and a dense network of ER tubules (right-most arrowhead). Panel F depicts a STED super-resolution image showing an NHS ester pan-stained Golgi stack in a ManII-GFP expressing HeLa cell. The arrowheads show five distinct Golgi cisternae. Panel G depicts an anti-GFP STED image of the same area as Panel F. The arrowheads show three distinct Golgi cisternae. Panel H depicts an overlay of Panels F and G. The three left-most arrowheads point at ManII GFP-positive Golgi cisternae, and the two right-most arrowheads point at two ManII GFP-negative Golgi cisternae. Representative images from 11 (A), 2 (B-E), and 3 (F-H) independent experiments. Panel I depicts a distribution of distances between neighboring mitochondrial cristae (n=123 line profiles, N=4 independent experiments) calculated from cross-sections like those along the dashed line shown in Panel A. Panel J depicts a distribution of ER tubule diameters (n=142 cross-sections, N=2 cells from 1 independent experiment). Panel K depicts an inter-cisternal distance distribution in Golgi stacks (n=193 line profiles, N=3 independent experiments). Medians and interquartile ranges are shown with whiskers drawn down to the minimum and maximum values. Means±standard deviations are reported. Panels A, B, and F are displayed with a white-to-black color table. Panels C, E, and G are displayed with a black-to-white color table. All scale bars are corrected for the determined expansion factor. Scale bars, (A) 500 nm, (B-E) 1 μm, (F-H) 250 nm.

Figure 32:
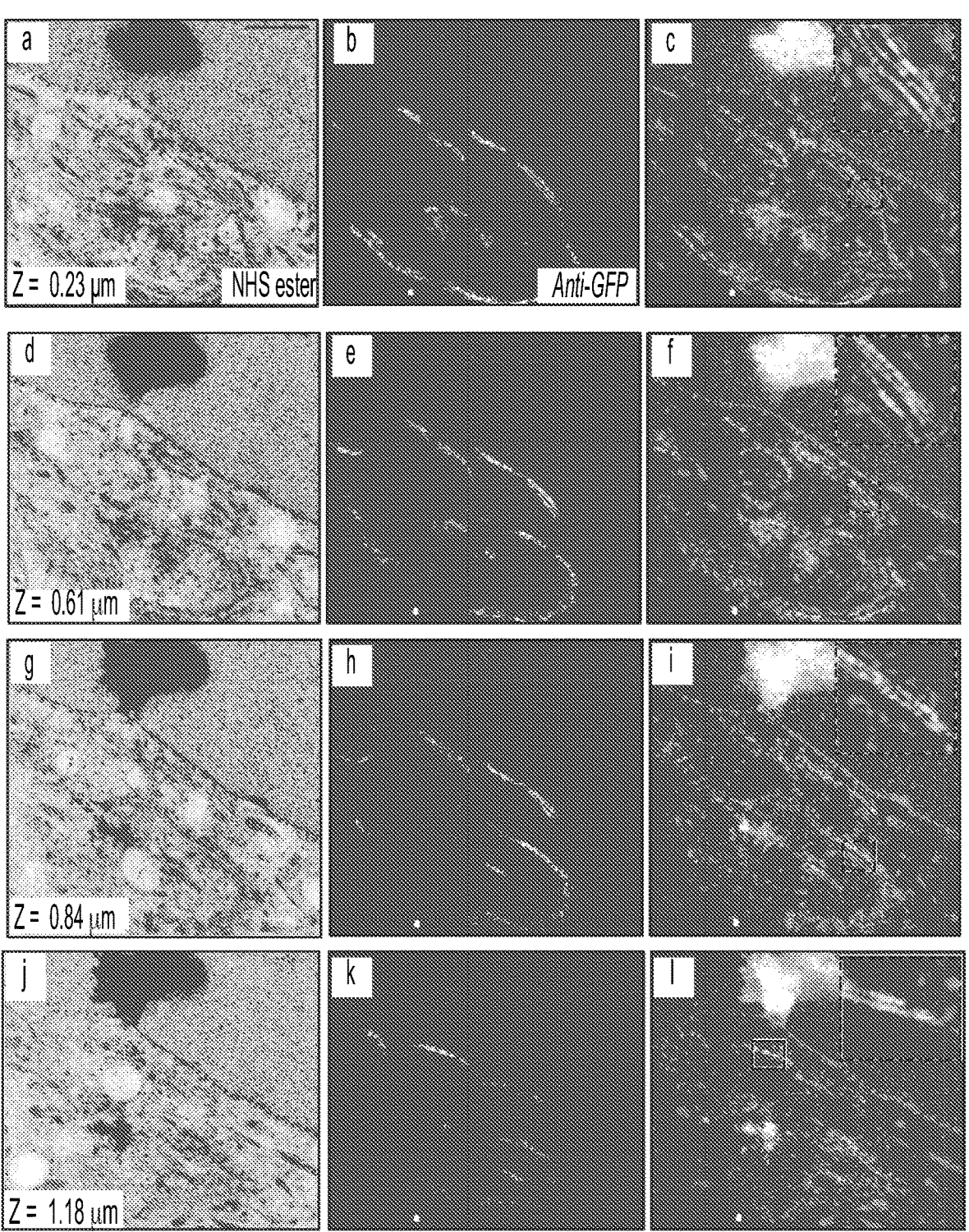

FIG. 32 are images of samples expanded through a pan-expansion technique, showing compatibility with 3D imaging, according to an embodiment of the claimed invention. Panels A-L depict images from a 3D image stack featuring the Golgi complex next to the nucleus in a HeLa cell expressing Golgi-localized ManII-GFP. Panels A, D, G, and J depict NHS ester images at axial positions 0.23, 0.61, 0.84 and 1.18 μm, respectively, displayed with a white-to-black color table. Panels B, E, H, and K depict anti-GFP images of the same fields of view as Panels A, D, G, and J, displayed with a black-to-white color table. Panels C, F, I, and L depict overlays of the NHS ester and anti-GFP images. Representative images from 5 (A-L) independent experiments. The insets show the zoomed-in boxes and reveal individual ManII-positive Golgi cisternae. Panels B, E, H, and K were corrected for crosstalk (see Methods). Scale bar and axial positions are corrected for the determined expansion factor. Scale bars (A-L) 2 μm.

Figure 33:
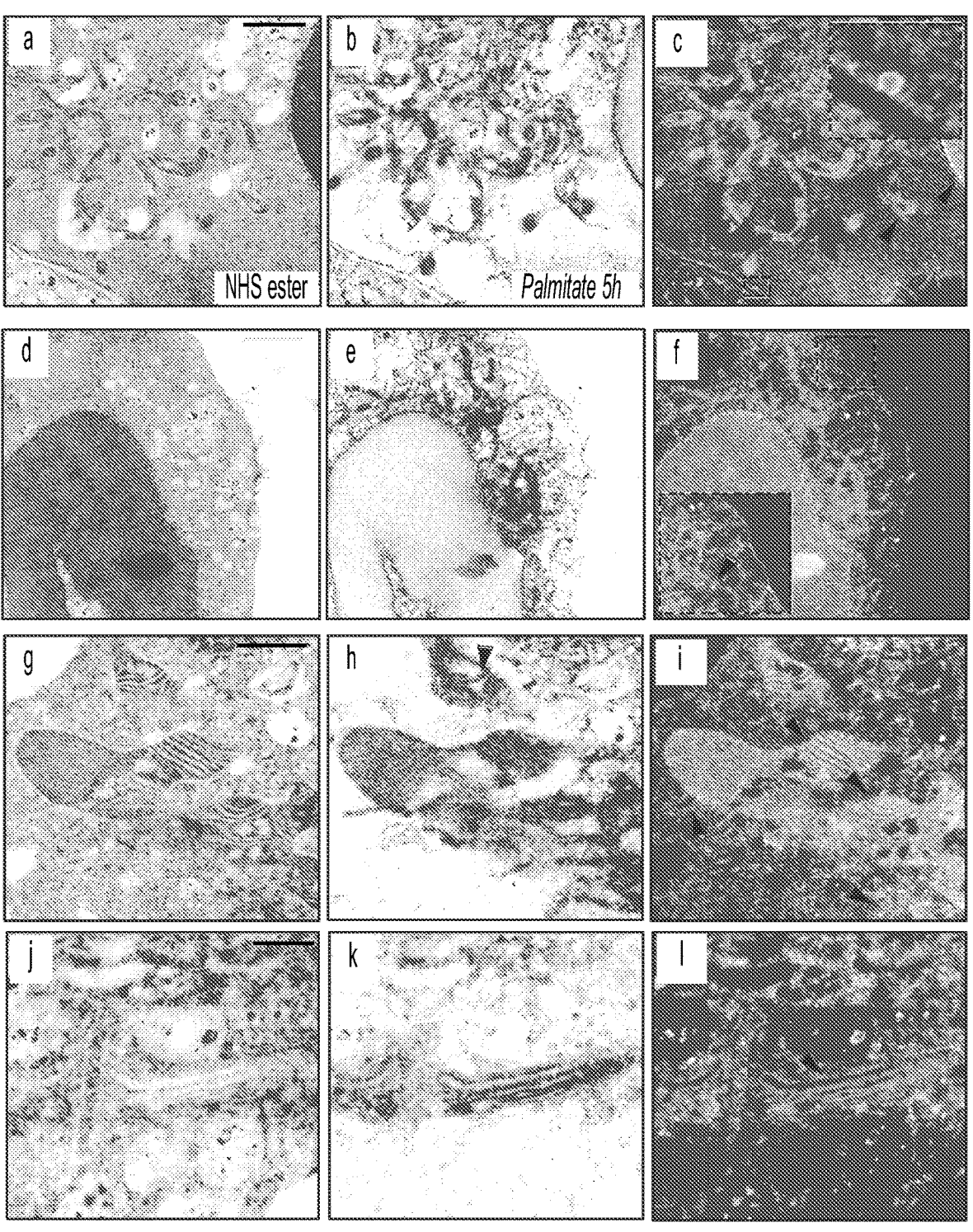

FIG. 33 are images of samples expanded through a pan-expansion technique, demonstrating differential pan-staining of the palmitoylated proteome, according to an embodiment of the claimed invention. Panel A depicts NHS ester pan-stained HeLa cell. Panel B depicts palmitate pan-staining corresponding to the same area as shown in Panel A. Panel C depicts overlay of Panels A and B. The area in the box is shown in the inset and reveals a vesicular structure resembling a clathrin-coated pit. The right-most arrowhead points at the palmitate-rich nuclear envelope. The bottom-most arrowhead points at a tubular structure resembling an ER tubule near a mitochondrion. Panel D depicts a NHS ester pan-stained HeLa cell. Panel E depicts palmitate pan-staining corresponding to the same area as shown in Panel D. Panel F depicts an overlay of Panels D and E. The area in the box is shown in the inset and reveals ER tubules (arrowhead). Panel G depicts a NHS ester pan-stained image of a HeLa cell showing mitochondria. Panel H depicts palmitate pan-staining corresponding to the same area as shown in Panel G. The arrowhead points at a mitochondrial crista with two palmitate-rich membranes. Panel I depicts an overlay of Panel G and H. The two top-most arrowheads point at mitochondrial cristae and the two bottom-most arrowheads point at tubule-like structures resembling ER tubules. Panel J depicts a NHS ester pan-stained image of a HeLa cell showing a Golgi stack. Panel K depicts palmitate pan-staining corresponding to the same area as shown in Panel J. Panel L depicts an overlay of Panels J and K. The arrowhead points at a palmitate-rich Golgi cisterna. Representative images from 2 (A-L) independent experiments. Panels A, B, D, E, G, H, J, and K are displayed with a white-to-black color table. Scale bars are not corrected for the expansion factor. Scale bars, (A-C) 30 μm, (D-F) 50 μm, (G-I) 20 μm, (J-L) 10 μm.

Figure 34:
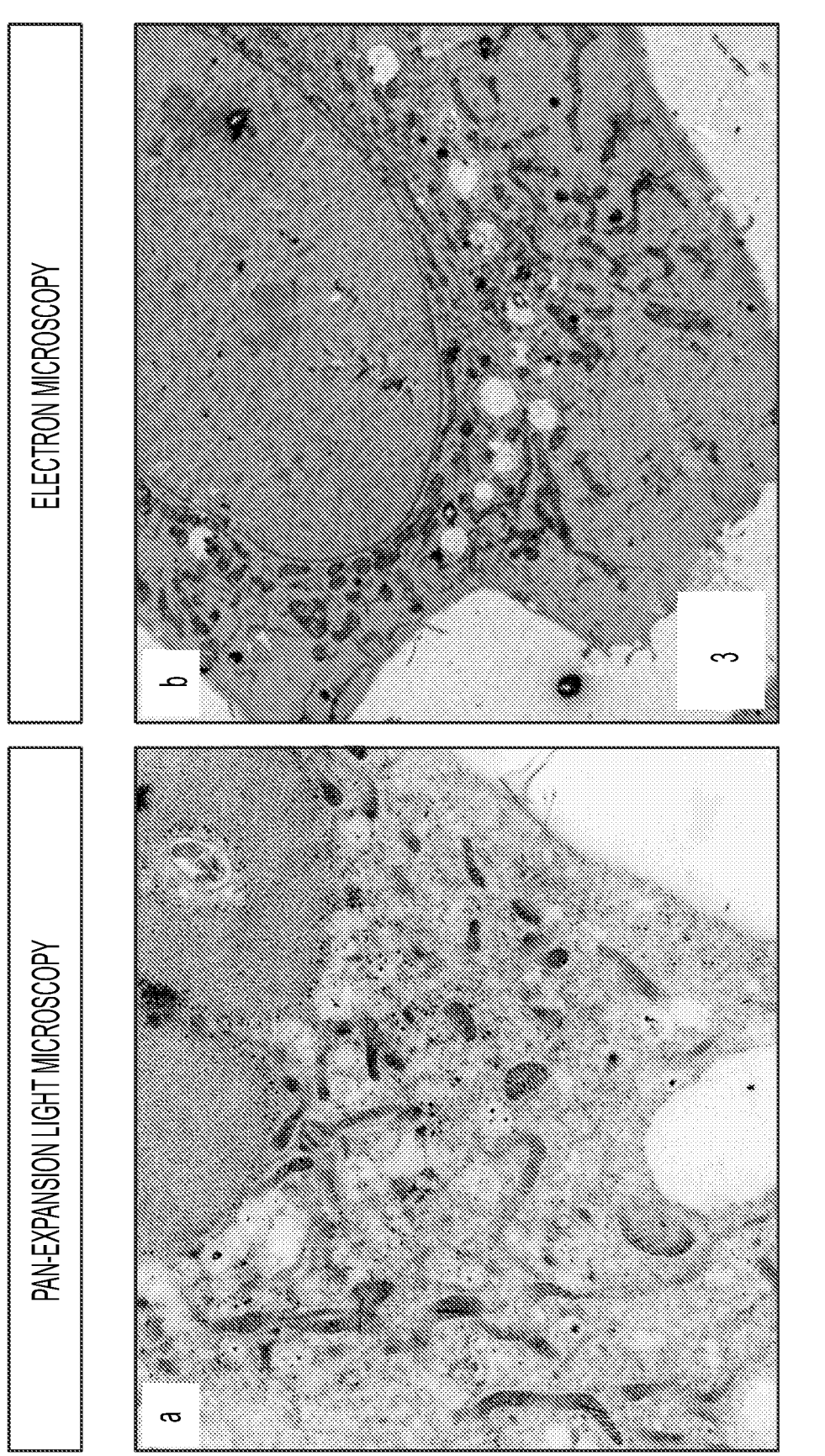

FIG. 34 is an image of a HeLa cell pan-stained with NHS ester (Panel A) displayed with an inverted color table resembling EM images (Panel B) obtained with embodiments of the claimed invention.

FIG. 35 is an image of a HeLa cell nucleus expanded ~40-fold through a pan-expansion technique showing conventional chromosome staining overlaid with novel EM-like contextual image, according to an embodiment of the claimed invention. Panel A depicts a NHS ester pan-stained nucleus showing nucleolus ultrastructure (top-most arrow: dense fibrillar center; right-most arrow: fibrillar component; left-most arrow arrow: granular component). Panel B depicts the same area as in Panel A showing granular SYTOX Green staining corresponding to nucleosomes. Panel C depicts an overlay of Panels A and B. Scale bars are corrected for the expansion factor. Scale bars, (A-C) 800 nm.

Figure 36:
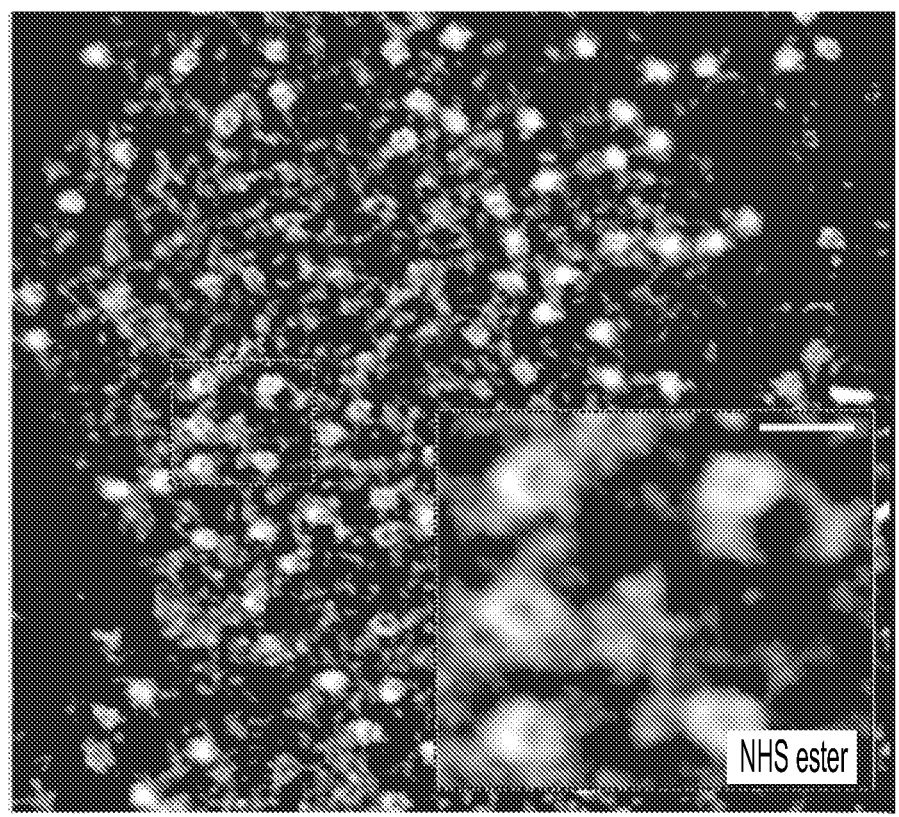

FIG. 36 is an image of a HeLa cell nucleus surface pan-stained with NHS ester showing hollow nuclear pore complexes (NPCs), obtained with embodiments of the claimed invention. Scale bar is corrected for the expansion factor. Scale bars, 70 nm.

Figure 37:
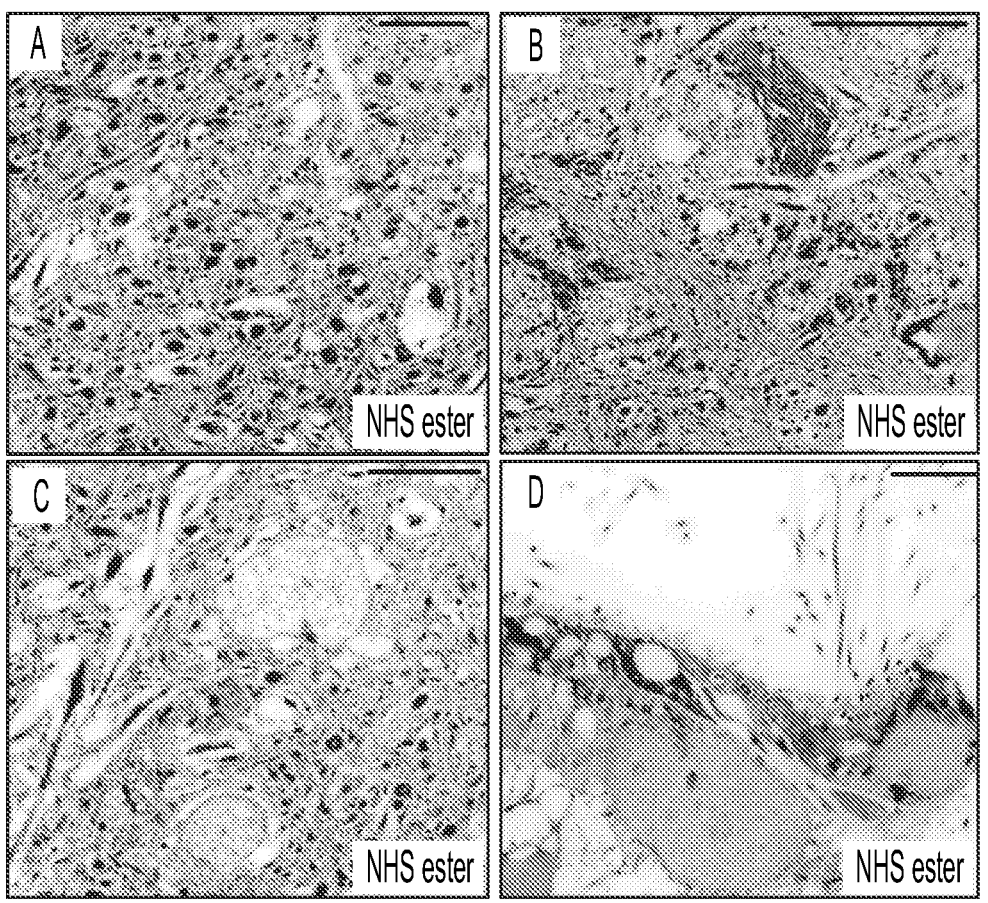

FIG. 37 are images of 50-μm-thick mouse brain tissue sections expanded 14-fold and pan-stained with NHS ester, obtained with embodiments of the claimed invention. Scale bars are not corrected for the expansion factor. Scale bars, (A-D) 50 μm.

FIG. 38 is an image of a 70-μm-thick mouse brain tissue section expanded 5-fold and pan-stained with a lipophilic dye, obtained with embodiments of the claimed invention. Panel A depicts BODIPY-TR Methyl Ester-stained mouse brain tissue section showing lipophilic structures. Panel B depicts the zoomed-in box in Panel A highlighting membranous structures in a neuron soma (top-most arrow: ER tubules; middle arrow: lipid droplet; bottom-most arrow: nuclear envelope). Scale bar is not corrected for the expansion factor. Scale bar, (A) 50 μm.

Figure 39:
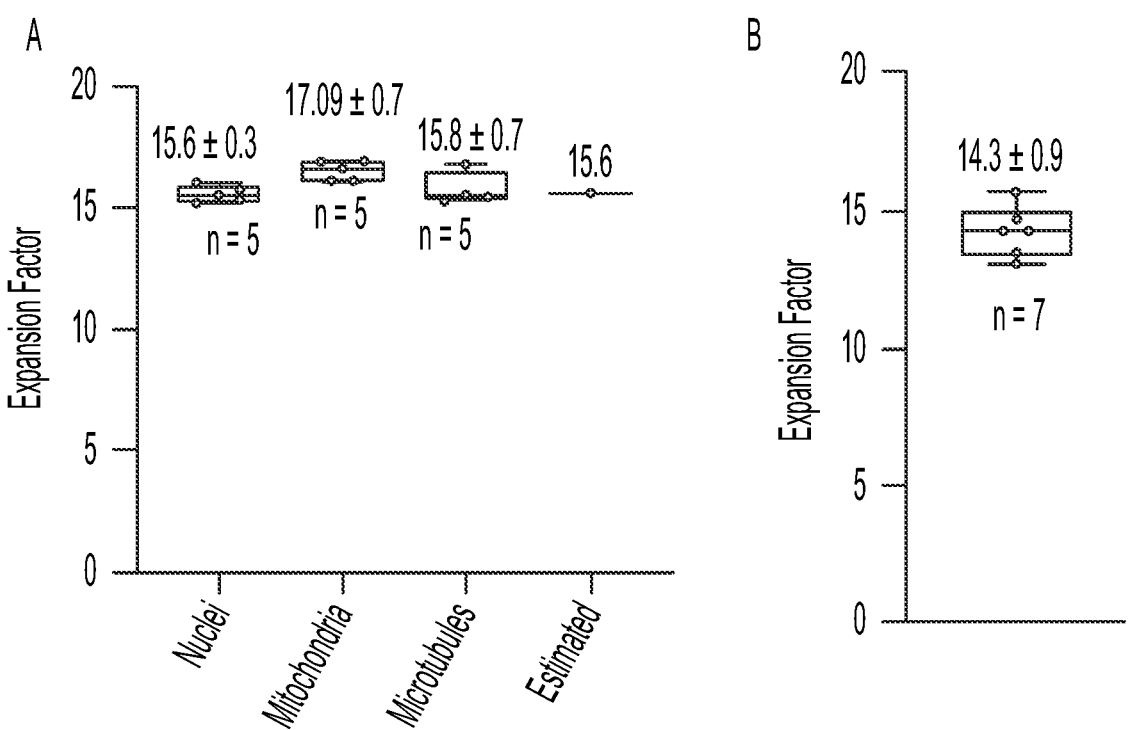

FIG. 39 are measurements of the expansion factors across different structures according to an embodiment of the claimed invention. Panel A depicts an expansion factor determined from registering pre-expansion to post-expansion images of nuclei, mitochondria, and microtubules (Nuclei: n=5 cells; Mitochondria: n=5 cells; Microtubules: n=5 cells, N=1 experiment). The figure also shows the estimated expansion factor determined from averaged nuclei cross-section measurements in the same experiment (n=39 nuclei; N=1 experiment). Panel B depicts an average expansion factor achieved with pan-ExM (n=6 experiments). Panel C depicts a table showing expansion factors calculated from averaged nuclei cross-section measurements from 7 independent experiments. In Experiment 3, the crosslinker N,N'-cystaminebisacrylamide (BAC) was used at 0.1% (w/v) concentration in the final hydrogel instead of N,N'-methylenebisacrylamide (BIS). The expansion factor determined from Experiment 3 was not included in determining the average expansion factor (Panel B). Medians and inter-quartile ranges are shown with whiskers drawn down to the minimum and maximum values. Means±standard deviations are reported.

Figure 40:
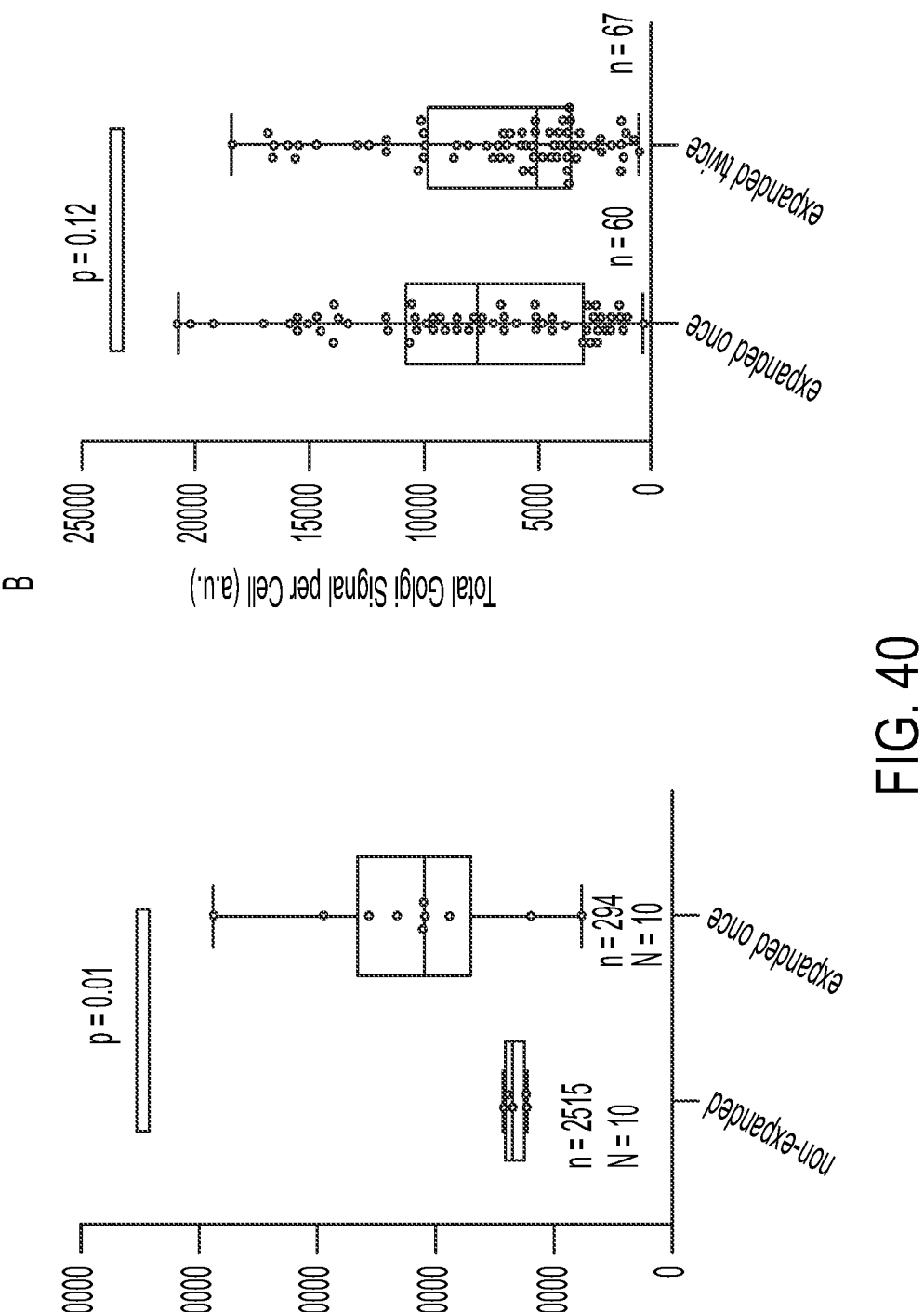

FIG. 40 depicts measurement of protein retention of samples according to an embodiment of the claimed invention. Panel A depicts ER signal comparison in a non-expanded sample with a sample expanded once. (Non-expanded: n=2515 cells, N=10 FOVs; Expanded once: n=294 cells, N=10 FOVs). Panel B depicts Golgi signal comparison in a sample expanded once with a sample expanded twice. (Expanded once: n=60 cells; Expanded twice: n=67 cells). For each distribution, median and inter-quartile range are shown with whiskers drawn down to the minimum and maximum values.

Figure 41:
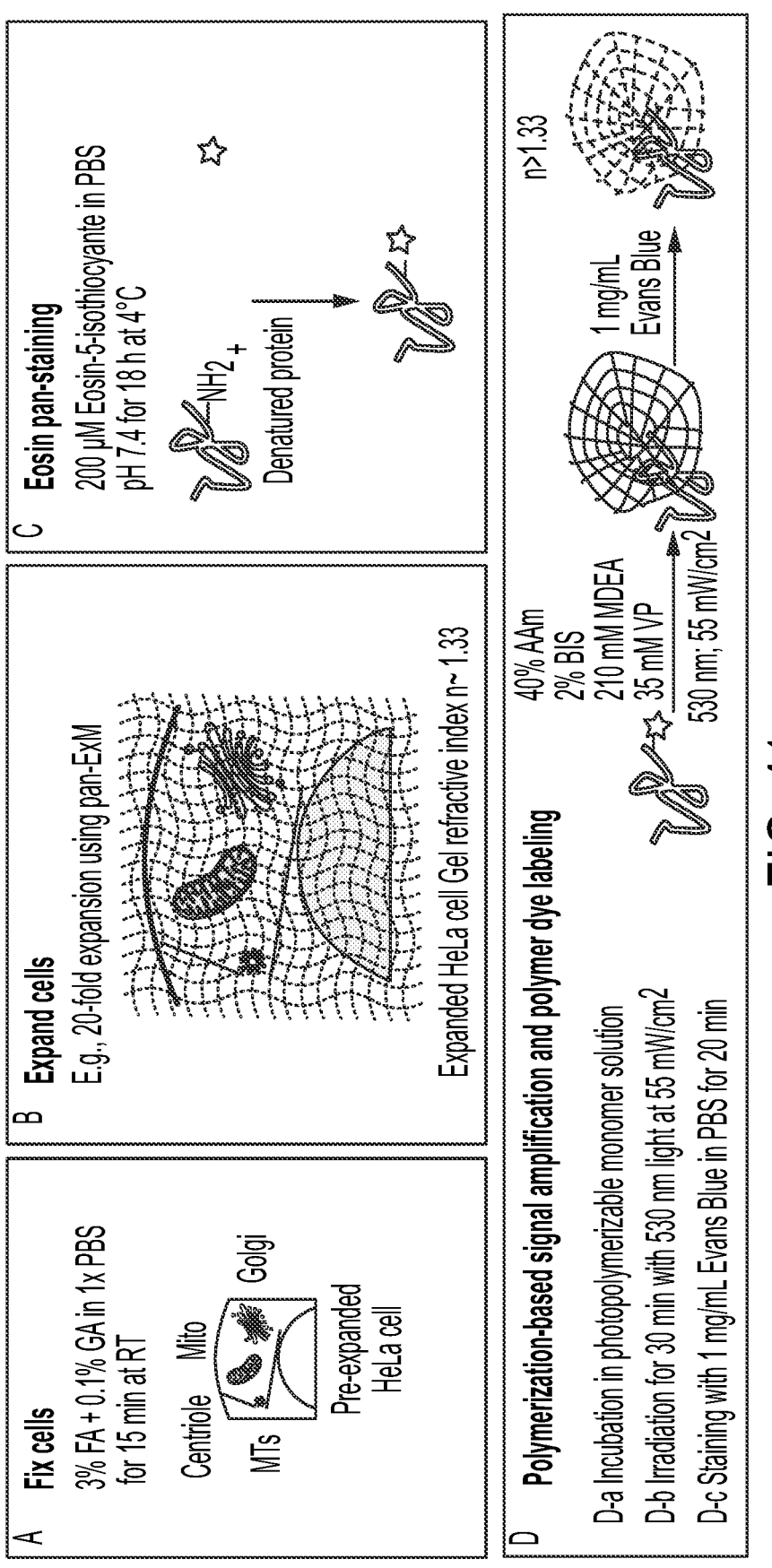

FIG. 41 depicts a schematic for panception, a polymerization-based pan-stain signal amplification technique applied to expanded cells, according to an embodiment of the claimed invention. In Panel A depicts biological samples (e.g., cells) are chemically fixed (e.g., using 4% FA and 0.1% glutaraldehyde (GA)). In Panel B the samples are expanded more than 10-fold (e.g., 20-fold expansion using a pan-ExM protocol). The expanded gel has a refractive index (n) close to that of water (n~1.33). In Panel C the cells are pan-stained with a photoinitiator (e.g., 200 µM amine-reactive eosin-5-isothiocynate). In Panel D the sample is incubated in a photo-polymerizable monomer solution (e.g., 40% AAm+2% BIS+210 mM N-methyldiethanolamine (MDEA)+35 mM N-vinyl-2-pyrrolidone (VP), where AAm and VP are monomers, MDEA is a tertiary amine, and BIS is a cross-linking reagent). The sample is then irradiated with light of appropriate wavelength to initiate free-radical photopoly-merization (e.g., 530 nm light at 55 mW/cm² for 30 min). The formed photopolymer is generally of higher refractive index (n>1.33) than the expansion hydrogel, rendering it visible by the unaided eye. The photopolymer is optionally stained with a visible dye (e.g., 1 mg/mL blue dye Evans Blue) to enhance the visible contrast.

FIG. 42 illustrates the chemicals and reactions involved in panception, according to an embodiment of the claimed invention. Panel A depicts the chemicals used in the photo-polymerization reaction. Panel B depicts the mechanism of light-initiated free-radical generation by eosin and MDEA. Panel C depicts the eosin regeneration reaction in atmospheric oxygen.

Figure 43:
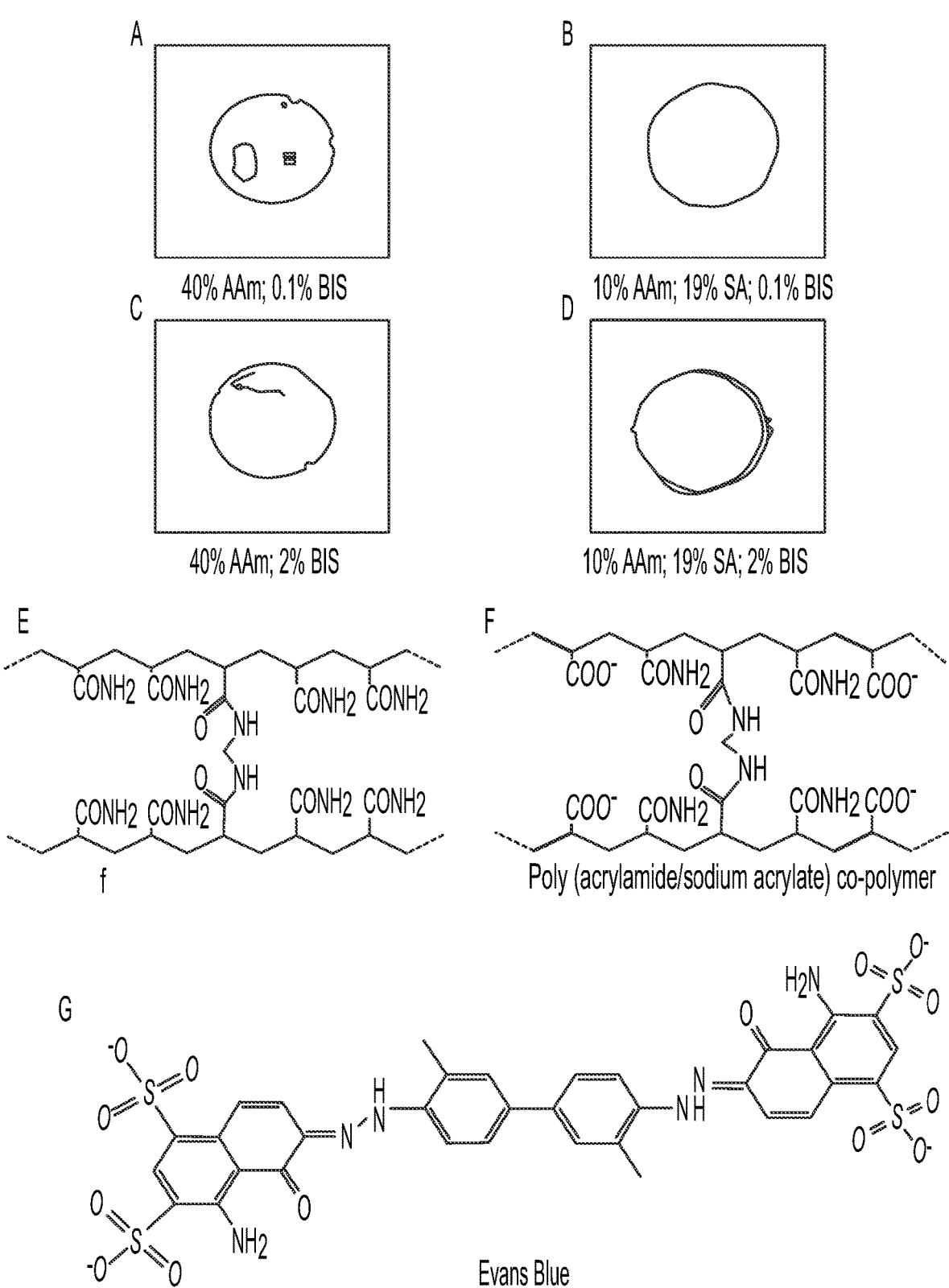

FIG. 43 depicts the justification of using Evans Blue as a visible dye stain in panception, according to an embodiment of the claimed invention. Panels A-B show that Evans Blue, an anionic dye, efficiently stains neutral polyacrylamide hydrogels but not anionic poly(acrylamide/sodium acrylate) co-polymers, regardless of hydrogel crosslinker concentration. Panels A, and C depict photopolymers composed of 210 mM MDEA+35 mM VP+40% AAm+0.1% (A) or 2% (C) BIS % w/w+12.5 µM eosin, photopolymerized with 530 nm LED at 12 mW/cm2 for 10 min on a 35 mm 10 mm glass coverslip and stained with 1 mg/mL Evans Blue for 20 min. Because these hydrogels are neutral, they are efficiently stained with Evans Blue. Panels B and D depict polymers composed of 10% AAm+19% SA+0.1% (B) or 2% (D) BIS % w/v+0.25% APS/TEMED polymerized at RT for 3 h and stained with 1 mg/mL Evans Blue for 20 min. Because these hydrogels are anionic, they are not stained with Evans Blue. Panel E depict chemical structure of polyacrylamide polymer. Panel F depict chemical structure of poly(acrylamide/sodium acrylate) co-polymer (blue: negatively-charged carboxylic groups). Panel G depict chemical structure of Evans Blue dye (blue: negatively-charged sulfate groups that repel carboxylic groups in anionic poly(acrylamide/sodium acrylate) co-polymers). The sulfate groups in Evan Blue repel the carboxylic groups in poly(acrylamide/sodium acrylate) co-polymers), preventing their staining.

Figure 44:
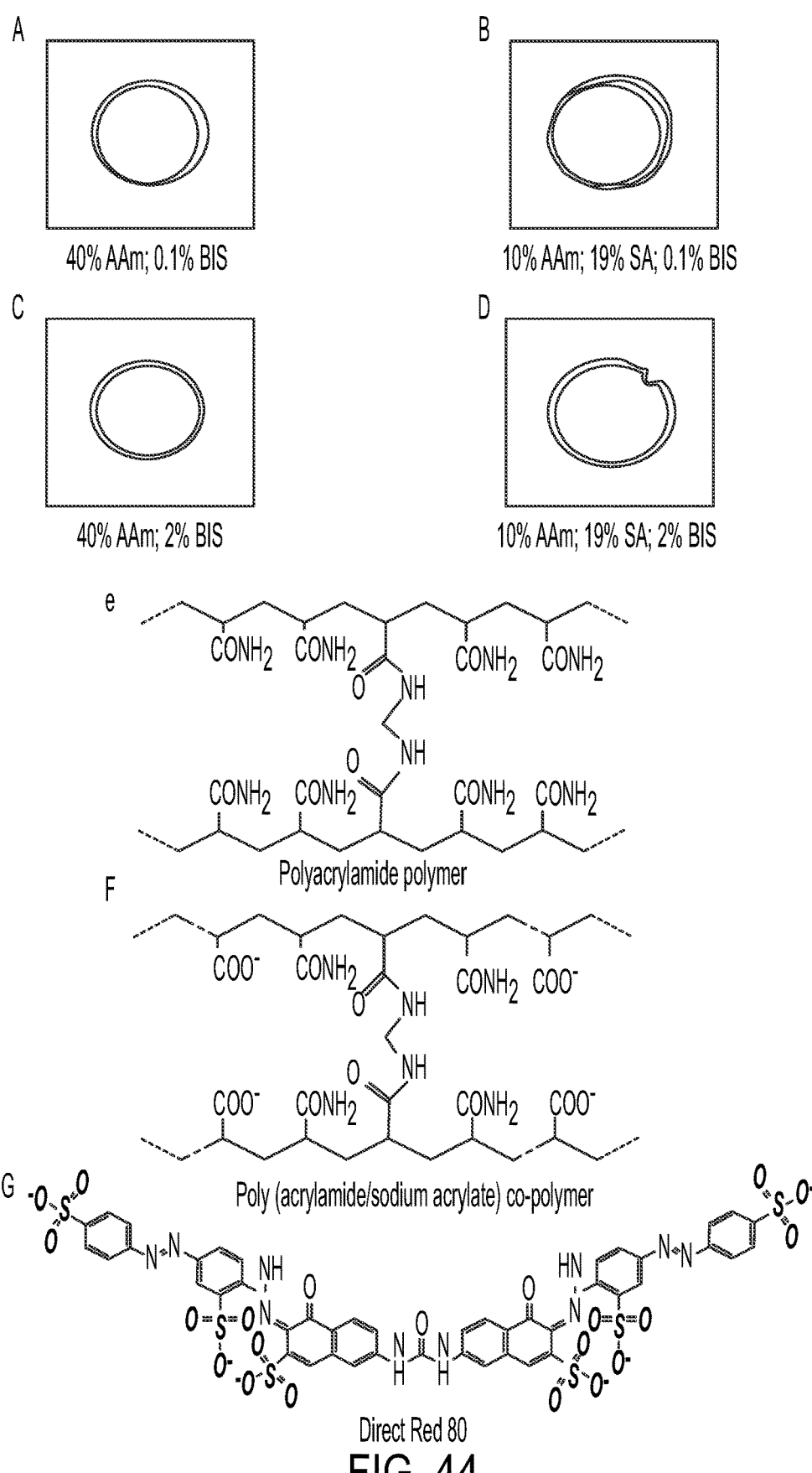

FIG. 44 depicts the justification of using Direct Red 81 as a visible dye stain in panception, according to an embodiment of the claimed invention. Panels A-D depict the same assay as that detailed in FIG. 43, showing that Direct Red 81 stains neutral but not anionic hydrogels. Panel F depict chemical structure of poly(acrylamide/sodium acrylate) co-polymer (shaded: negatively-charged carboxylic groups). Panel G depicts the chemical structure of Evans Blue dye (shaded: negatively-charged sulfate groups that repel car-boxylic groups in anionic poly(acrylamide/sodium acrylate) co-polymers). The sulfate groups in Direct Red 81 repel the carboxylic groups in poly(acrylamide/sodium acrylate) co-polymers), preventing their staining.

Figure 45:
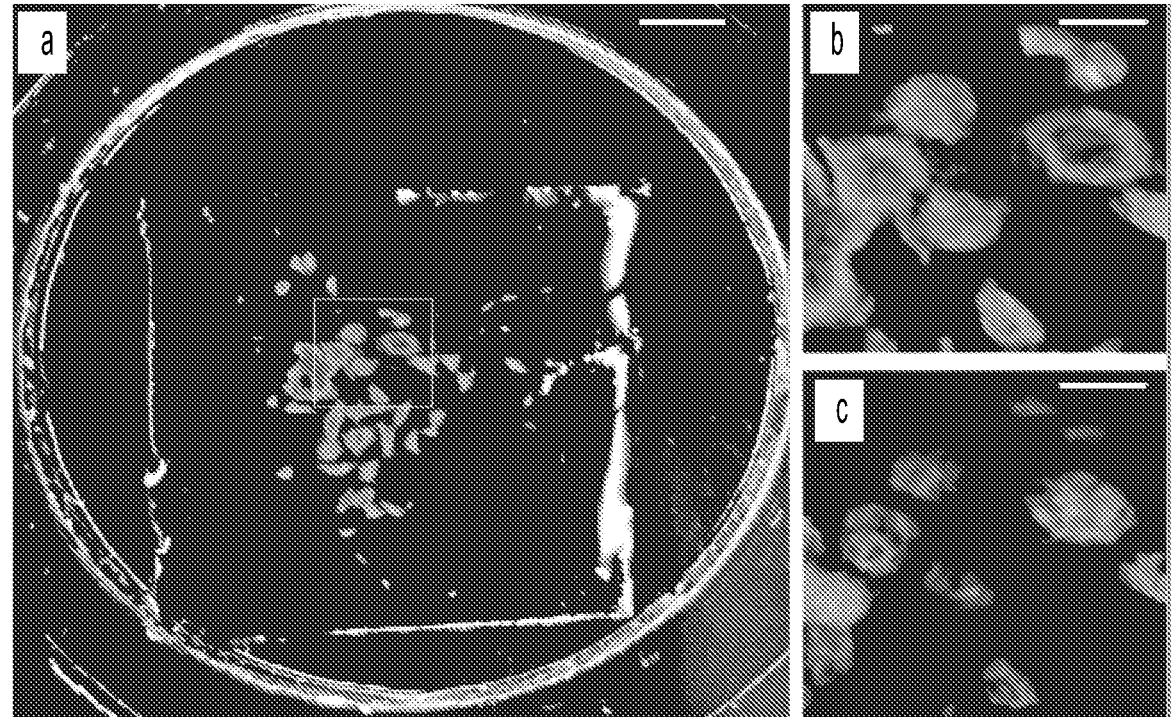

FIG. 45 are images of a panception-processed sample revealing individual HeLa cells with the unaided eye, according to an embodiment of the claimed invention. HeLa cells were expanded 20-fold and stained with 200 µM eosin-5-isothiocyante. Samples were expanded in deionized water and sectioned to ~1 mm thickness. Gels were incubated in photopolymer solution (40% AAm+2% w/w BIS+210 mM MDEA+35 mM VP) and photopolymerized using 530 nm LED light at ~55 mW/cm2 for 15 min. Gels were rinsed in water, imaged on an IPHONE 11 smartphone, stained with 1 mg/mL Evans Blue for 20 min, washed in water, and imaged again. Panel A depicts a panception reveals a visible cluster of ~45 cells stained with Evans Blue dye, placed on a 14 mm MatTek dish, and imaged against a dark background. Panel B depicts an inset in Panel A showing single cells with distinguishable nuclei and cytosol. Panel C depicts same field of view as Panel B after photo-polymerization but before staining with Evans Blue, show-ing visible photopolymer since its refractive index is higher than that of the expansion hydrogel. Images acquired with an iPhone11 and adjusted for contrast. Scale bars are not corrected for sample enlargement factor. Scale bars, (A) 1.5 mm, (B-C) 0.5 mm.

Figure 46:
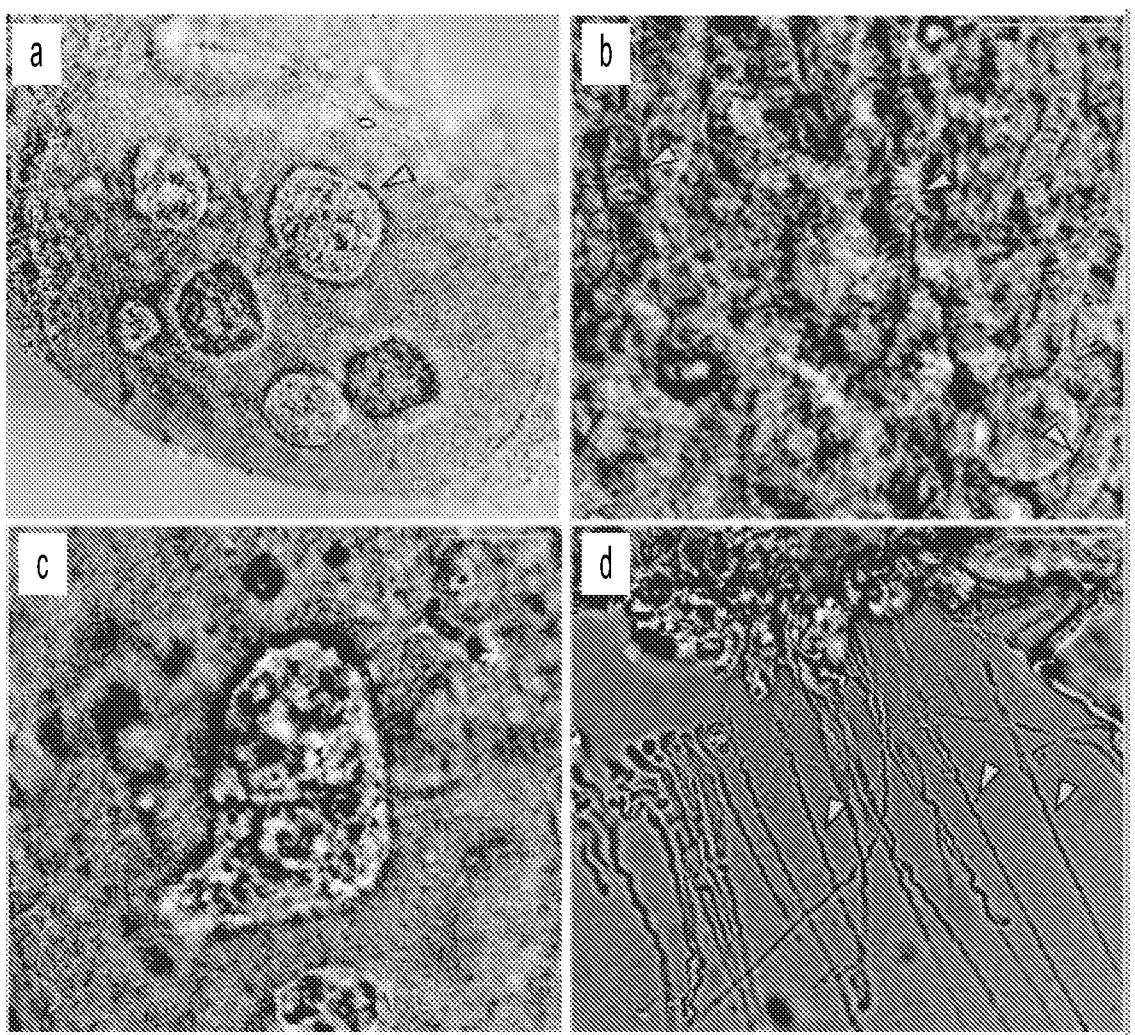

FIG. 46 are images of panception-processed samples imaged with a phase-contrast microscope, according to an embodiment of the claimed invention. Panel A depicts an image of a nucleus in a 20-fold expanded and panception-processed HeLa cell revealing nucleoli (arrowheads). Panel B depicts an image of the cytosol in revealing mitochondria (arrowheads). Panel C depicts zoomed-in image of a nucleolus. Panel D depicts an image of filopodia (arrowheads). Scale bars are not corrected for the expansion factor. Scale bars, (A,C,D) 50 µm, (B) 20 µm.

Figure 47:
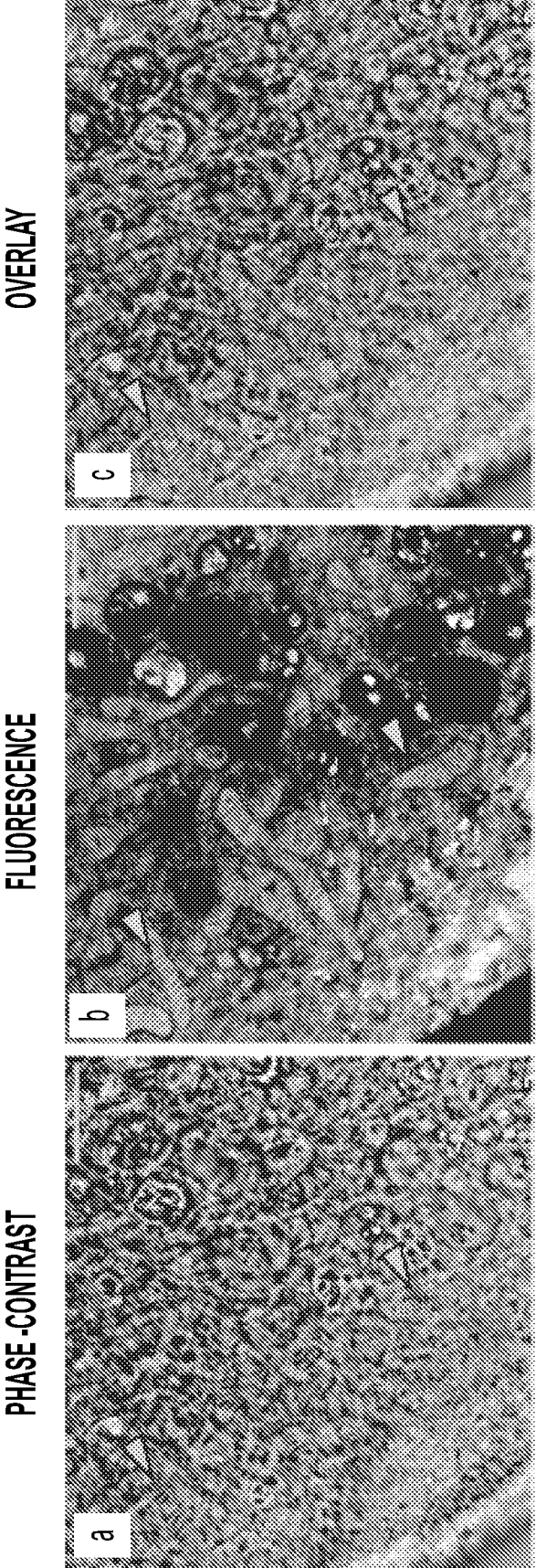

FIG. 47 are images of panception-processed samples imaged with both phase-contrast microscopy and fluorescence microscopy. Panel A depicts a phase-contrast image of a panception-processed HeLa cell cytosol revealing mitochondria. Panel B depicts a fluorescence image of the same area corresponding to Panel A. Panel C depicts an overlay of Panels A and B. Arrowheads reveal correlated images of mitochondria. Scale bars are not corrected for the expansion factor. Scale bars, (A-C) 20 μm.

Figure 48:
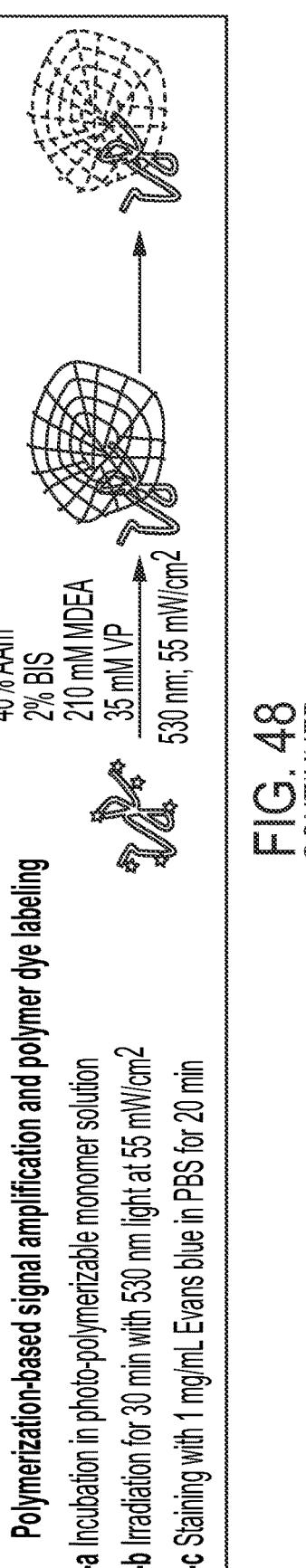

FIG. 48 depicts a schematic for panception in 100-fold expanded cells, according to an embodiment of the claimed invention. Panel A depicts biological samples (e.g., cells) are chemically fixed (e.g., using 4% FA and 0.1% GA). In Panel B, the samples are expanded 20-fold expansion using a pan-ExM protocol. The expanded gel has a refractive index (n) close to that of water (n~1.33). In Panel C, the cells are pan-stained with biotin (e.g., 200 μM amine-reactive NHS ester-PEG4-biotin). In Panel D, the samples are expanded another 5-fold for a final expansion factor of 100, being that the second swellable hydrogel (hydrogel, in Panel B) is synthesized with a cleavable crosslinker that is orthogonal to that used to synthesize the first swellable hydrogel (e.g., N,N'-bis(acryloyl)cystamine (BAC)). In Panel E, the sample is labeled with streptavidin conjugated to a photoinitiator (e.g., eosin) and biotin dendrimers (e.g., 8-arm PEG biotin) are optionally used to amplify the streptavidin staining. Pan-staining with amine-reactive chemicals can occur after 20-fold expansion (as opposed to after 100-fold expansion) because at a higher sample components dilution, the reaction of isothiocyanates (e.g. eosin-5-isothiocyanate) with primary amines on proteins can be significantly less efficient (100-fold expansion corresponds to 1,000,000 fold sample dilution, while 20-fold dilution corresponds to 8,000 sample dilution). Biotin-streptavidin reaction on the other hand has a high reaction dissociation constant ($K_d$~10e-14 M), enabling efficient pan-staining even at very low reactant concentration. Thus, a two-step pan-staining scheme can be used, where high $K_d$ enzymatic reactions such as biotin-streptavidin labeling are used post-100 fold sample expansion. In Panel F, the sample is incubated in a photo-polymerizable monomer solution (e.g., 40% AAm+2% BIS+ 210 mM MDEA)+35 VP). The sample is then irradiated with light of appropriate wavelength to initiate free-radical photopolymerization (e.g., 530 nm light at 55 mW/cm² for 30 min). The formed photopolymer is generally of higher refractive index (n>1.33) than the expansion hydrogel, rendering it visible by the unaided eye. The photopolymer is optionally stained with a visible dye (e.g., 1 mg/mL blue dye Evans Blue) to enhance the visible contrast.

Figure 49:
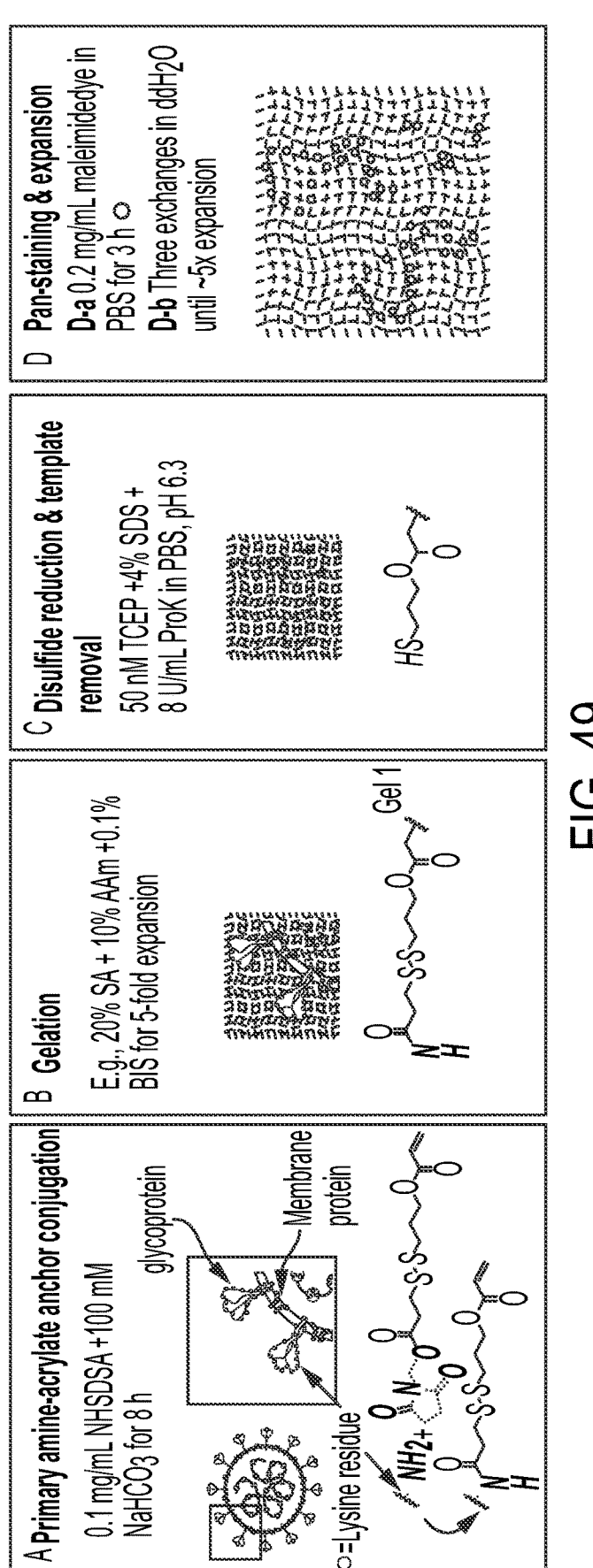

FIG. 49 illustrates a schematic for sample pan-imprint expansion according to an embodiment of the claimed invention. In Panel A, cells are first treated with N-hydroxysuccinimide disulfide acrylate (NHSDSA). In Panel B, the sample is embedded in a swellable hydrogel (e.g., 20% SA+10% AAm+0.1% BIS) such that the positions of the amino acid lysine are imprinted to this polymer network. In Panel C, the template proteome is removed with protease proteolysis (e.g., proteinase K) and denaturants (e.g., SDS) and the anchors are dissociated with a reducing reagent (e.g., tris (2-carboxyethyl) phosphine (TCEP)). In Panel D, the sample interfaces (i.e., imprinted positions of amino acids) are labeled with thiol reactive dyes (e.g., maleimide dyes) and the hydrogel is expanded ~5-fold in water and imaged.

Figure 50:
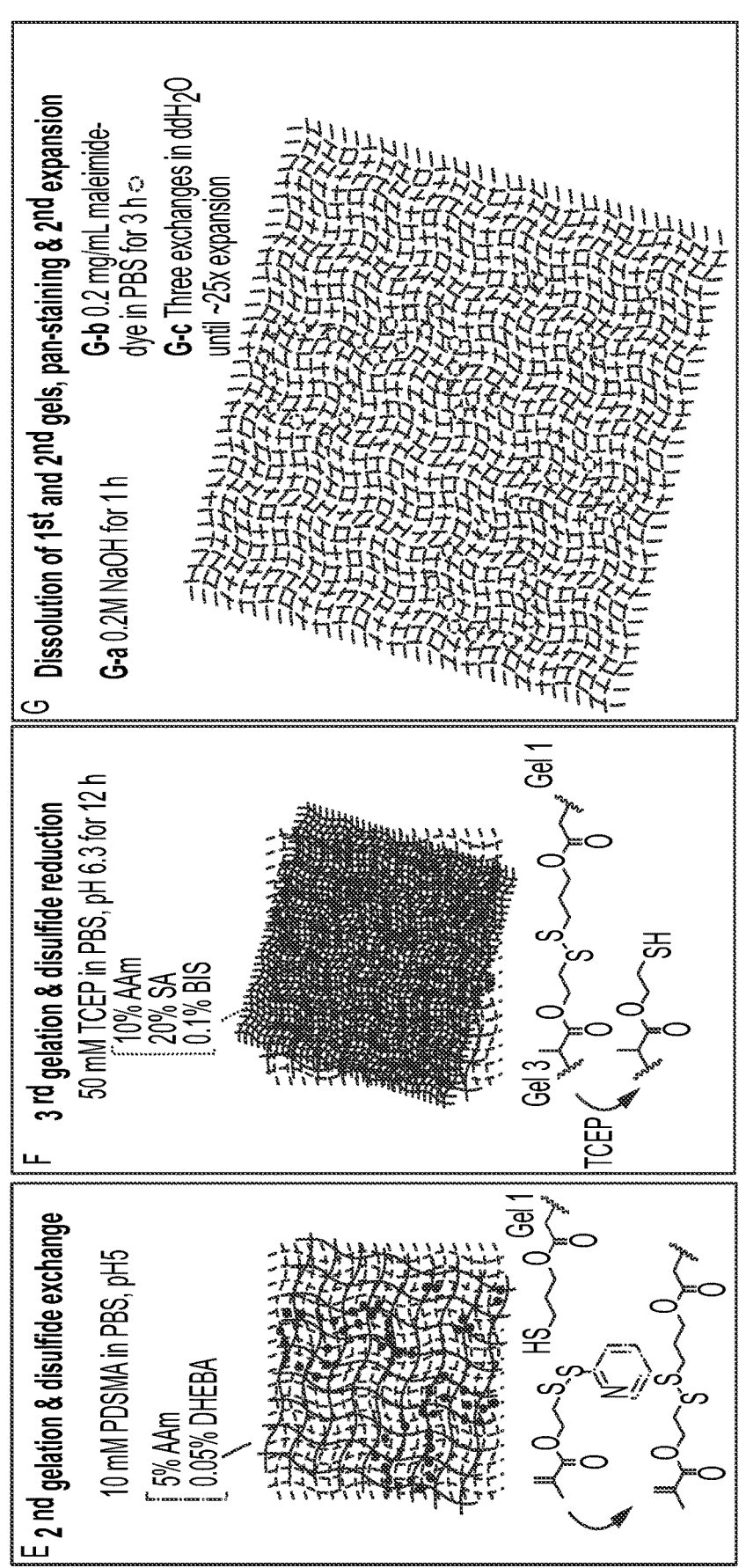

FIG. 50 illustrates a schematic for an iterative form of pan-imprint expansion. Steps in Panels A-D are identical to those illustrated in FIG. 49, except the swellable hydrogel in Step 2 is crosslinked with base-cleavable DHEBA and the sample interfaces are not labeled in Panel D. In Panel E, the expanded sample is embedded in a neutral polyacrylamide polymer crosslinked with DHEBA to hold it in its expanded volume, and pyridyl disulfide ethyl methacrylate (PDSMA)

is introduced in excess to participate in disulfide exchange with the reduced thiol groups. The disulfide exchange process involves attack of the thiol at the disulfide, breaking the —S—S— bond, with subsequent formation of a new disulfide polymer 'anchor' molecule comprising a portion of the original disulfide compound. This way, the position of lysine residues will be re-imprinted with nanometer accuracy in the subsequent swellable hydrogel. In Panel F, the sample is embedded in a second swellable hydrogel and the anchors are dissociated with TCEP reduction. This process (steps in Panels C-F) could be repeated in an iterative fashion using hydrogels with reversible acrylamide crosslinkers that are orthogonal to DHEBA. In Panel G, the reduced thiol molecules are conjugated to maleimide-functionalized dyes and the hydrogel is expanded ~5-fold in pure water for a final expansion factor of ~25-fold.

DEFINITIONS

The instant invention is most clearly understood with reference to the following definitions.

Bulk Labeling

As used herein, the term "bulk label" or "pan-stain" refers to labeling large portions of non-identical molecules in a biological sample. The opposite of a bulk label is a specific label achieved through techniques such as immunofluorescence, immunohistochemistry or immunocytochemistry. Generally, pan-staining is applied after sample expansion to densely label newly exposed binding surfaces on biomolecules. Generally, pan-stains label more than one type of cellular compartment. Preferably, imaging a pan-stained expanded sample reveals the underlying sample ultrastructure (e.g., organelles) without the need for specific labels.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Iterative Expansion Microscopy

Methods and systems described herein relate to spatial expansion of samples for microscopy. A sample can be embedded in a first polymer network. The polymer network can expand the sample spatially, such as to a factor of 4 from the sample's original dimensions. The expanded sample can then be further embedded in a second polymer network, which can further expand the sample spatially. Components of the sample can be preserved through an entanglement of polymer chains arising from the first polymer network and the second polymer network. The sample can thus be significantly expanded in dimensions relative to the sample's original form (e.g., by a factor to 21). This significant expansion can result in high clarity and resolution of the overall sample structure via a fluorescence microscope.

Sample Labeling

The sample can be labeled with a variety of reagents. For example, the sample can be labeled with either a specific reagent or a global (e.g., pan-) reagent, or a combination thereof. Specific reagents can label specific molecules or proteome-specific components of the sample. Examples of specific reagents include, but are not limited to, a lipid-specific reagent, a DNA-specific reagent, a reagent covalently or electrostatically conjugated to a protein, an amine-reactive probe, and the like. Likewise, global reagents can indiscriminately label many of the sample components.

In some cases, the sample can be labeled via bulk labeling. Bulk labeling can include utilizing a reagent that reacts with chemical groups of a certain class such as a hydroxyl class, aldehydes classes, amino classes, and the like. In some cases, the sample can be labeled with specific or molecular-specific labeling. For example, specific or molecular-specific labeling can utilize a reagent that reacts in a highly targeted manner with predefined molecules in the sample such as direct and indirect immunofluorescence and fluorescent proteins.

In some cases, at least one of the reagents is succinimidyl ester (including N-Hydroxysuccinimide (NHS) esters), isocyanate, isothiocyanate, benzoyl fluoride, carboxylic ester, tetrafluorophenyl (TFP) ester, sulfodichlorophenol (SDP) ester, carbonyl azide, or sulfonyl chloride. In some cases, at least one of the reagents is an aldehyde-containing reagent, including coumarins, pyrenes, o-phthaldialdehyde (OPA), and naphthalenedicarboxaldehyde (NDA). In some cases, at least one of the reagents is thiol-reactive, including iodoacetamides, maleimides, 2-thiopyridine, 3-arylpropiolonitrile, benzylic halides, and bromomethylketones. In some cases, at least one of the reagents is an arylating chemical such as NBD halides. In some cases, at least one of the reagents reacts with tyrosine residues such as diazonium salts, and PTAD. In some cases, at least one of the reagents can bind to the N- or C-terminus of a protein. In some cases, at least one of the reagents is capable of biorthogonal modification of proteins containing unnatural amino acids such as L-Azidohomoalanin and L-homopropargylglycine.

In some cases, at least one of the reagents reacts with carboxylic acids on proteins, for example hydrazines, hydroxylamines or amines. In some cases, at least one of the reagents reacts with glutamine residues via transglutaminase-catalyzed transamidation. In some cases, at least one of the reagents binds to proteins via hydrophobic interactions, such as SYPRO orange. In some cases, at least one of the reagents is a lipophilic dye which binds to cellular membranes, such as BODIPY TR Methyl Ester. In some cases, at least one reagent is an antibody. In some cases, at least one reagent is applied to the sample while alive.

In some cases, multiple reagents can label a sample. For example, at least 2 reagents can label the sample, which can then be recorded in at least 2 channels of a sample image. In some cases, at least 2 reagents are represented as different colors.

Further, the sample can be labeled with the one or more reagents at different steps in the expansion technique. For example, the sample can be labeled prior to the embedding the sample into a polymer network. In some cases, a reagent can be embedded within a polymer network, such that the sample can be labeled when embedded into the polymer network. In some cases, the sample can be labeled subsequent to an expansion of the sample. When iteratively expanded, the sample can be labeled subsequent to the first the second expansion, the third expansion, and the like.

In some cases, bulk labeling a sample after 10-fold or more sample expansion allows for identification of cellular organelles based on their morphological characteristics, rendering pan-staining an optical contrast equivalent to heavy metal staining in electron microscopy (EM).

Sample Fixation

In some cases, enzymatic reactions in a sample can be inactivated (e.g., chemically) while preserving its structure, a process called fixation, prior to embedding the sample in a polymer network. Chemical fixation of biological samples can be reversed if the fixative molecule is susceptible to degradation under certain conditions or if changing the temperature, pH, pressure, and/or addition of specific reactants to the equilibrium favors the dissociation reaction. Examples of fixatives that are heat-reversible include commonly used formaldehyde (FA). Examples of degradable fixatives include homobifunctional diimidoesters such as thiol-cleavable dimethyl dithiobispropionimidate (DTBP), base-cleavable dimethyl suberimidate (DMS), dimethyl pimelimidate (DMP), and dimethyl adipimidate (DMA)), homobifunctional amine-reactive crosslinkers including thiol-cleavable dithiobis(succinimidyl propionate) (DSP), hydroxylamine-cleavable ethylene glycol bis(succinimidyl succinate) (EGS), thiol-cleavable 1,5-difluoro-2,4-dinitrobenzene (DFDNB)), and heterobifunctional N-Hydroxysuccinimide-pyridyldithiol crosslinkers including thiol-cleavable succinimidyl 3-(2-pyridyldithio)propionate (SPDP), succinimidyl 6-(3(2-pyridyldithio)propionamido) hexanoate (LC-SPDP), and 4-succinimidyloxycarbonyl-alpha-methyl-α(2-pyridyldithio)toluene (SMPT).

Sample Embedding

The sample can be contacted with a hydrogel composed of a variety of synthetic monomers in the form of ethylenically unsaturated polymerizable molecules. These monomers include, but are not limited to, electrolyte monomers that enable the hydrogel to swell in low-ionicity solutions such as sodium acrylate (SA).

If the sample is fixed with reversible and amine-reactive crosslinkers, the embedded hydrogel preferably contains amine-functionalized monomers in excess of the fixed material to simultaneously quench fixation and react with the modification formed by the fixative. Examples of amine-reactive crosslinkers include formaldehyde (FA), dimethyl suberimidate (DMS), dimethyl pimelimidate (DMP), and dimethyl adipimidate (DMA). Examples of amine-reactive monomers include acrylamide (AAm), allylamine (ADP), 2-vinylpyridine (2-VP), N-(2-aminoethyl)acrylamide hydrochloride (AEM), and 2-aminoethyl methacrylate hydrochloride (AMA).

If the sample is fixed with thiol-cleavable fixatives such as crosslinkers with disulfide bridges, the embedded hydrogel preferably contains thiol-reactive monomers in excess of the fixed material to react with the fixation modification through disulfide exchange. Examples of thiol-reversible fixatives include dithiobis(succinimidyl)propionate (DSP), 1,5-difluoro-2,4-dinitrobenzene (DFDNB), succinimidyl 3-(2-pyridyldithio)propionate (SPDP), succinimidyl 6-(3(2- pyridyldithio)propionamido)hexanoate (LC-SPDP), and 4-succinimidyloxycarbonyl-alpha-methyl-α(2-pyridyldithio)toluene (SMPT). Examples of thiol-reactive monomers include pyridyl disulfide ethyl methacrylate (PDSMA) and pyridyl disulfide ethyl acrylamide (PDSAAm).

In some cases, the sample is conjugated to non-swellable polymer material before being contacted with swellable polymer material. The purpose is to allow the hybrid formed between the non-swellable polymer and the sample to entangle with the swellable polymer, simultaneously preserving and expanding the sample content in this swellable polymer network. In one embodiment, the non-swellable polymer is linear (e.g., non-crosslinked) and composed of polymerizable monomers, such as acrylamide, acrylate, methacrylamide, methacrylates, allylamine, allylalcohol, acrolyl, methacrolyl. In one embodiment, the non-swellable polymer is linear and composed of a,b-unsaturated aldehyde polymers. In one embodiment, the non-swellable polymer is crosslinked with a non-cleavable crosslinker such as N,N'-methylenebis(acrylamide) (BIS), N,N'-methylenediacrylamide, and piperazine diacrylamide. In one embodiment, the non-swellable polymer is crosslinked with cleavable crosslinkers such as N,N'-(1,2-dihydroxythylene)bisacrylamide) (DHEBA), N,N'-bis(acryloyl)cystamine (BAC), and N,N'-diallyl L-tartardiamide (DATD). In this latter embodiment, the crosslinks are generally cleaved after embedding in swellable polymer material and before sample expansion.

Sample Expansion

A sample can be expanded via sample embedding in a polymer network. The polymer network can be swellable, such that when a liquid (e.g., water) is absorbed by the polymer network, the polymer network expands. As the polymer network expands, components of the embedded sample can separate proportionally. Thus, the dimensions of the sample can increase linearly. For example, an expansion using a first polymer can result in an expansion of a cell's dimension by a factor between 3 and 5. In some cases, the polymer network can be a part of a hydrogel. For example, a standard direct expansion can result in an expansion of a cell by a factor between 3 and 5. Using a rigid crosslinker such as piperazine diacrylamide at low concentrations, the sample expansion can be augmented to 8- to 10-fold without compromising hydrogel mechanical stability. Example compositions of the hydrogels can include, but are not limited to, polyacrylamide, polyacrylate, or a combination thereof.

In some cases, the polymer network can be in the shape of a polymeric mesh. The mesh can include interwoven polymer chains. The spacing between the interwoven polymer chains can be on the nanoscale. For example, the mesh size for the polymer network can include 3 nm prior to expansion.

Without being bound by theory, Applicant believes that the expansion methods described herein lower (by spatially distributing) the emission density of the labeled sample. This allows for imaging using relatively simple imaging devices.

Sample Expansion

A sample can be expanded via sample embedding in a polymer network. The polymer network can be swellable by dialysis, such that when a liquid (e.g., water) is absorbed by the polymer network, the polymer network expands. As the polymer network expands, components of the embedded sample can separate proportionally. Thus, the dimensions of the sample can increase linearly. For example, a standard direct expansion can result in an expansion of a cell by a factor between 3 and 5. Using a rigid crosslinker such as piperazine diacrylamide at low concentrations, the sample expansion can be augmented to 8- to 10-fold without compromising hydrogel mechanical stability. Example compositions of the hydrogels can include, but are not limited to, polyacrylamide, polyacrylate, or a combination thereof.

In some cases, the polymer network can be in the shape of a polymeric mesh. The mesh can include interwoven polymer chains. The spacing between the interwoven polymer chains can be on the nanoscale. For example, the mesh size for the polymer network can include 3 nm prior to expansion.

Sample Iterative Expansion by Polymer Entanglement

Polymer chains from one polymer network can entangle with polymer chains from another polymer network when introduced together. For example, embedding a sample within a first polymer network, and subsequently embedding the sample-and-first-polymer-network combination into a second polymer network, can result in polymer chain entanglement. The chain entanglement can physically interlock protein-polymer hybrids in the second polymer network. This interlocking can prevent the proteome of the embedded sample during iterative expansion of the hydrogels from being washed out. Sample expansion techniques described herein can thus iteratively expand the dimensions of a sample by a factor significantly larger than conventional sample expansion techniques (e.g., by a factor of 20).

The combination of at least two orthogonal reversible crosslinkers with polymer entanglement can provide multiple expansion iterations by going back and forth between crosslinkers.

Sample Expansion by Modification of Polymer Networks

In one embodiment, a sample can be embedded in a hydrogel that is either swellable or non-swellable. The original sample-embedded hydrogel can be further modified to increase its size in three-dimension. In some embodiments, the modification of polymer networks can be an elongation of its polymer chains, or an insertion and/or formation of new polymer chains within it, or a combination thereof.

The hydrogel can be subjected to polymer chain elongation to enlarge in size. Polymer chain elongation is an insertion of monomers and/or linear polymers into existing polymer chains to increase their lengths. The elongation factor can be on the order of 2, 5-fold or more. In some embodiments, polymer chains are elongated by reversible addition-fragmentation chain-transfer (RAFT) polymerization of hydrophilic monomers. In some cases, the original sample-embedded polymer network is crosslinked with a trithiocarbonate (e.g., bis[(2-propionate)ethyl methacrylate] trithiocarbonate (bisPEMAT)). In some cases, RAFT polymerization of a trithiocarbonate-crosslinked polymer network occurs in the presence of polymerizable monomers, a photocatalyst, and light irradiation. In some cases, the photocatalyst is phenothiazine (PTH), the light source is a 400 nm LED, and the incorporated monomers are acrylamide and acrylate. In one embodiment, the sample-embedded hydrogel is composed of 10% acrylamide (AAm)+10% sodium acrylate (SA)+0.5% bisPEMAT. In some cases, the hydrogel is incubated in a monomer solution of 20% AAm+8% SA+0.035% PTH and exposed to 400 nm LED light irradiation in an oxygen-free atmosphere for over 6 h. In some cases, the resulting modified hydrogel is washed in deionized water and allowed to reach its maximum size.

In one embodiment, the sample-embedded hydrogel can be modified by polymer chain insertion. Polymer chain insertion can occur either by in situ polymerization of monomer inserts or by insertion of bifunctional linear polymers. The inserted polymer chains can serve as molecular spacers that physically separate the original polymer network chains from each other, thereby enlarging the sample hybrid.

In one embodiment, the sample-embedded hydrogel is synthesized with latent monomer insertion sites. In some cases, the latent insertion site is a chemical group capable of being converted into an ethylenically unsaturated polymerizable group. In some cases, the sample-embedded hydrogel is swellable and synthesized with a cleavable crosslinker. In some cases, the latent insertion sites are clickable handles (e.g., alkyne groups) or protected thiols (e.g., pyridyl disulfides). These sites can be converted into polymerizable groups via reaction with clickable monomers (e.g., azide acrylates) or thiol-reactive monomers (e.g., maleimide acrylate or pyridyl disulfide ethyl methacrylates (PDSMA)), respectively. In some cases, the latent insertion site is not converted into a polymerizable molecule.

In one embodiment, the sample-embedded hydrogel with polymerizable insertion sites has new polymer chains formed within it by in situ polymerization of monomer inserts, in the presence of a polymerization initiator. In some cases, these monomers form polyelectrolytes. In some cases, linear polymers are inserted in lieu of (or along with) monomers. Examples of linear polymers are polyacrylamide (pAAm) and low-persistence length polyethylene glycol (PEG) polymers. In some cases, the crosslinks of the original hydrogel are cleaved after in situ polymerization and before sample expansion. The modified hydrogel with new molecular spacers can be expanded in water. In some cases, the embedded sample is expanded 3-fold or more.

In one embodiment, the sample-embedded hydrogel with latent insertion sites has new polymer chains formed within it by insertion of bifunctional linear polymers. Preferably, the inserted bifunctional linear polymers are conjugated to the insertion sites. Examples of conjugation reactions include but are not limited to covalent binding, enzymatic reactions, electrostatic interactions. In some cases, the conjugation reaction is based on Click Chemistry. In some cases, the inserted bifunctional linear polymers are polyelectrolytes. One example is the insertion of poly(acrylamide-co-acrylic acid) polymer with two azido groups in a hydrogel with alkyne polymer insertion sites. In some cases, the crosslinks of the original hydrogel are cleaved after polymer insertion and before sample expansion.

In one embodiment, the inserted monomers or polymers contain new latent insertion sites, permitting another round of in situ polymerization or insertion of bifunctional linear polymers and thus increased sample enlargement.

Sample Panception (Unaided-Eye Perception)

In one embodiment a sample can be expanded, and its bulk signal (i.e., pan-stain) amplified to the extent its outline and structure becomes visible to the unaided eye. In some cases, a ~50 μm diameter cell is expanded 20-fold in each direction to become ~1 mm in size. The human eye can distinguish structures that are ~200 μm apart. Enlarged cells can be visible with the unaided eye if the signal is of sufficient visible contrast. Typically, a cell enlarged 20-fold with components labeled in a 1:1 ratio is not visible to the unaided eye. Preferably, the sample is bulk labeled with a reagent capable of initiating or catalyzing a signal amplification reaction. In some cases, the initiator initiates a polymerization-based signal amplification reaction where the bulk stain is amplified up to 1,000,000-fold. In some cases, the sample is bulk labeled with an amine-reactive polymerization initiator (e.g., eosin-5-isothiocyanate). In some cases, the polymer formed is of higher refractive index than the background substrate rendering it visible to the unaided eye. In some cases, the polymer formed is labeled with visible dyes such as Evans Blue to enhance its visible contrast. Generally, a cell expanded 20-to 100-fold with its bulk signal amplified by polymerization has its structure and underlying organelles (e.g., nucleus and mitochondria) discernible by the unaided eye.

Sample Pan-Imprint Expansion

In some cases, it is desirable to reveal the structures of individual untargeted proteins in their native ultrastructural context. Instead of expanding proteins in a swellable hydrogel, it is possible to expand the nanoscale protein imprint of the sample via the polymer network(s). In some of these cases, the sample may be too small to allow for proper expansion (e.g., a virus, a protein complex, a protein, etc.). However, an imprint created by the sample (e.g., amino acid positions) on a polymer network can be expanded. After sample embedding, the polymer network can be expanded. While the sample itself may not expand, the imprints left on the polymer network by the sample will expand proportionally with the dimensions of the polymer network. These imprints (e.g., expanded interface surfaces originating from the contact surfaces between the polymer network and the original sample) can be subsequently labeled in bulk, which can then be used to identify structural features or components of the original sample. In some cases, the imprints can be iteratively expanded as described above. A schematic outlining expansion and labeling of surface interfaces is illustrated in FIG. 49.

Additional Sample Preparation

Additional sample preparation steps can be implemented in order to effectuate or facilitate the sample expansion techniques described herein. In some cases, the molecular interactions between sample components are inactivated to allow for sample components to dissociate from each other evenly. In some cases the molecular interactions are electrostatic, or based on van der Waals forces, hydrogen bonding, and hydrophobic binding. For example, samples can be delipidated and/or denatured with heat and sodium dodecyl sulfate after being embedded in a polymer network. The delipidation and/or denaturation can extract lipids and/or unfold protein chains of sample. In some cases, the sample is denatured but not delipidated after being embedded in a polymer network. Examples of denaturants that do not efficiently extract lipids are chaotropic reagents such as urea, thiourea, lithium perchlorate, lithium acetate, magnesium chloride, formamide, trimethylamine, and guanidine hydrochloride. In some cases, the sample is homogenized with proteolysis with proteases such as serine, aspartic acid, mettalo, and cysteine proteases, and amino and carboxy peptidases.

Sample

A variety of samples can be expanded by the techniques described herein. For example, a sample can include, but is not limited to, at least one cell, at least one tissue section, a biofilm, cellular components, a patient-derived sample, a chemically fixed sample, a cryo-preserved sample, and the like.

Microscope

The sample can be prepared for imaging by a microscope. The microscope can be any type of microscope that can detect emitted, transmitted, reflected, or scattered light. For example, the microscope can include a fluorescence light microscope, a super-resolution microscope, and the like.

Sample Imaging

Sample expansion can result in higher quality imaging of the sample's proteome, particularly when imaging a sample's proteome in an ultrastructural context. Conventional microscopy techniques fail to provide the clarity, resolution, or depth required to image sample proteome in an ultra-structural context. While electron microscopy (EM) techniques can image the ultrastructural context of samples three-dimensionally, EM requires correlative microscopy techniques to produce images that combine the ultrastructural context with specific labels, resulting in the use of highly-specialized instruments and days to weeks of continuous data acquisition.

In contrast, imaging of expanded samples using the techniques described herein can be performed by conventional light microscopes, which significantly reduces the equipment costs, computer processing requirements, and time duration of generating an ultrastructural sample image.

Applications

These images of expanded samples can be used in a variety of industries and applications. For example, sample expansion can be used for diagnostic imaging. In these cases, the reagent can include differential protein labeling. The differential protein labeling can include labeling at least one post-translational modification. In some cases, the one post-translational modification can include acetylation, glycosylation, phosphorylation, ubiquitination, alkylation, SUMOylation, biotinylation, glutamylation, glycylation, isoprenylation, lipoylation, phosphopantetheinylation, phosphorylation, sulfation, selenation, C-terminal amidation, or hydroxylation.

Another example for using sample expansion for diagnostic imaging is revealing the spatial distribution of drug candidates in a sample. Another example can include the tracing of compartmentalized signals in a signaling cascade. Another example can include the structural analysis of misfolded protein aggregates involved in neurodegenerative diseases. Another example can include the visualization of the spatial distribution of diverse populations of bacteria in biofilms. Another example can include the identification of chromatin abnormalities in cancer detection.

Software Control

In some cases, at least parts of the techniques described herein can be implemented using software control. Control system 1800 can be an electronic device programmed to control the expansion and labeling of sample. The control system 1800 can be programmed to autonomously carry out a sample expansion regimen without the need for input (either from feedback devices or users) or can incorporate such inputs. The principles of how to use feedback (e.g., from a sensor) in order to modulate operation of a component are described, for example, in Karl Johan Astrom & Richard M. Murray, *Feedback Systems: An Introduction for Scientists & Engineers* (2008).

Control system 1800 can be a computing device such as a microcontroller (e.g., available under the ARDUINO® OR IOIO™ trademarks), general purpose computer (e.g., a personal computer or PC), workstation, mainframe computer system, and so forth. An exemplary control system is illustrated in FIG. 18. The control system 1800 can include a processor device (e.g., a central processing unit or "CPU") 1802, a memory device 1804, a storage device 1806, a user interface 1808, a system bus 1810, and a communication interface 1812.

Processor 1802 can be any type of processing device for carrying out instructions, processing data, and so forth.

Memory device 1804 can be any type of memory device including any one or more of random access memory ("RAM"), read-only memory ("ROM"), Flash memory, Electrically Erasable Programmable Read Only Memory ("EEPROM"), and so forth.

Storage device 1806 can be any data storage device for reading/writing from/to any removable and/or integrated optical, magnetic, and/or optical-magneto storage medium, and the like (e.g., a hard disk, a compact disc-read-only memory "CD-ROM", CD-ReWritable CDRW," Digital Versatile Disc-ROM "DVD-ROM", DVD-RW, and so forth). Storage device 1806 can also include a controller/interface for connecting to system bus 1810. Thus, memory device 1804 and storage device 806 are suitable for storing data as well as instructions for programmed processes for execution on processor 1802.

User interface 1808 can include a touch screen, control panel, keyboard, keypad, display or any other type of interface, which can be connected to system bus 1810 through a corresponding input/output device interface/adapter.

Communication interface 1812 can be adapted and configured to communicate with any type of external device, or with other components of the gas chromatography system. Communication interface 1812 can further be adapted and configured to communicate with any system or network, such as one or more computing devices on a local area network ("LAN"), wide area network ("WAN"), the Internet, and so forth. Communication interface 1812 can be connected directly to system bus 1810 or can be connected through a suitable interface.

Control system 1800 can, thus, provide for executing processes, by itself and/or in cooperation with one or more additional devices, that can include algorithms for controlling components of a microscopy and/or sample expansion system in accordance with the claimed invention. Control system 1800 can be programmed or instructed to perform these processes according to any communication protocol and/or programming language on any platform. Thus, the processes can be embodied in data as well as instructions stored in memory device 1804 and/or storage device 1806, or received at user interface 1808 and/or communication interface 1812 for execution on processor 1802.

Machine Learning

In some cases, machine learning can be trained to identify the components of the proteome of a sample image or a sample expanded according to an expansion technique described herein. A machine learning algorithm can be a part of control system 1800 of FIG. 18. A machine learning algorithm or estimator can be trained to identify an organelle or spatial feature of a labeled and expanded sample.

For example, one or more images of a sample stained with specific label reagents can be inputted into the machine learning algorithm or estimator. Additionally, one or more of the same sample stained with a global label reagent can also be inputted into the machine learning algorithm or estimator. The machine learning algorithm or estimator can identify different components of the sample (e.g., via the label-specific sample) and determine characteristics of the identified components (e.g., patterns of emission intensity from the global label reagent). From these identified characteristics, the machine learning algorithm or estimator can compare these characteristics to components of the globally labeled sample images, and identify components of the globally labeled sample(s) based on the comparison (and without the need for organelle-specific labels).

Although the machine learning algorithm or estimator is particularly useful with the spatial expansion methods described herein, Applicant believes that the machine learning algorithm or estimator (e.g., after training on samples spatially expanded according to the methods described herein) can be applied to conventional samples, whether expanded using conventional ExM protocols or unexpanded.

Example Process Flow #1

Figure 14:
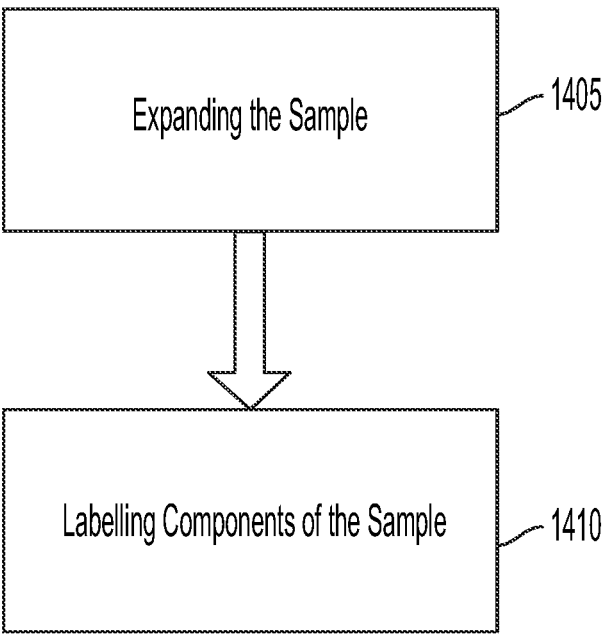

FIG. 14 depicts an example workflow process for preparing a biological sample for the purpose of identifying structural features of the sample, according to an embodiment of the claimed invention.

At Step 1405, the sample can be physically expanded by at least a factor of 2 in at least 1 dimension. The expansion can include embedding the sample into at least one polymer network. The polymer network can include polymer chains crosslinked with crosslinkers. A liquid, such as deionized water, can be introduced to the polymer network, which can increase in size linearly. The embedded sample can also increase in size with the introduction of the liquid.

In some cases, the embedded sample can then be re-embedded into a second polymer network. The second polymer network can include polymer chains that are crosslinked with other crosslinkers. In some cases, these crosslinkers can be orthogonal to the crosslinkers of the first polymer network.

The re-embedding of the sample into the second polymer network can entangle polymer chains of the first polymer network with polymer chains from the second polymer network. This entanglement can preserve or retain the proteome of the sample during expansion.

After re-embedding, a liquid can be introduced to the second polymer network, causing the second polymer network to swell. The expanded sampled can thus be further expanded, such as to a factor of $4^2$. Additionally, as the entanglement of the polymer networks preserved the proteome of the sample, the expanded sample does not significantly degrade during expansion.

At Step 1410, a majority of a plurality of components of the sample can be labeled with at least one reagent. The reagent can be a component-specific reagent, a global reagent, or a combination thereof. As the different components of the expanded sample are spatially distanced from each other, the components are identifiable through the labeling.

Example Process Flow #2

Figure 15:
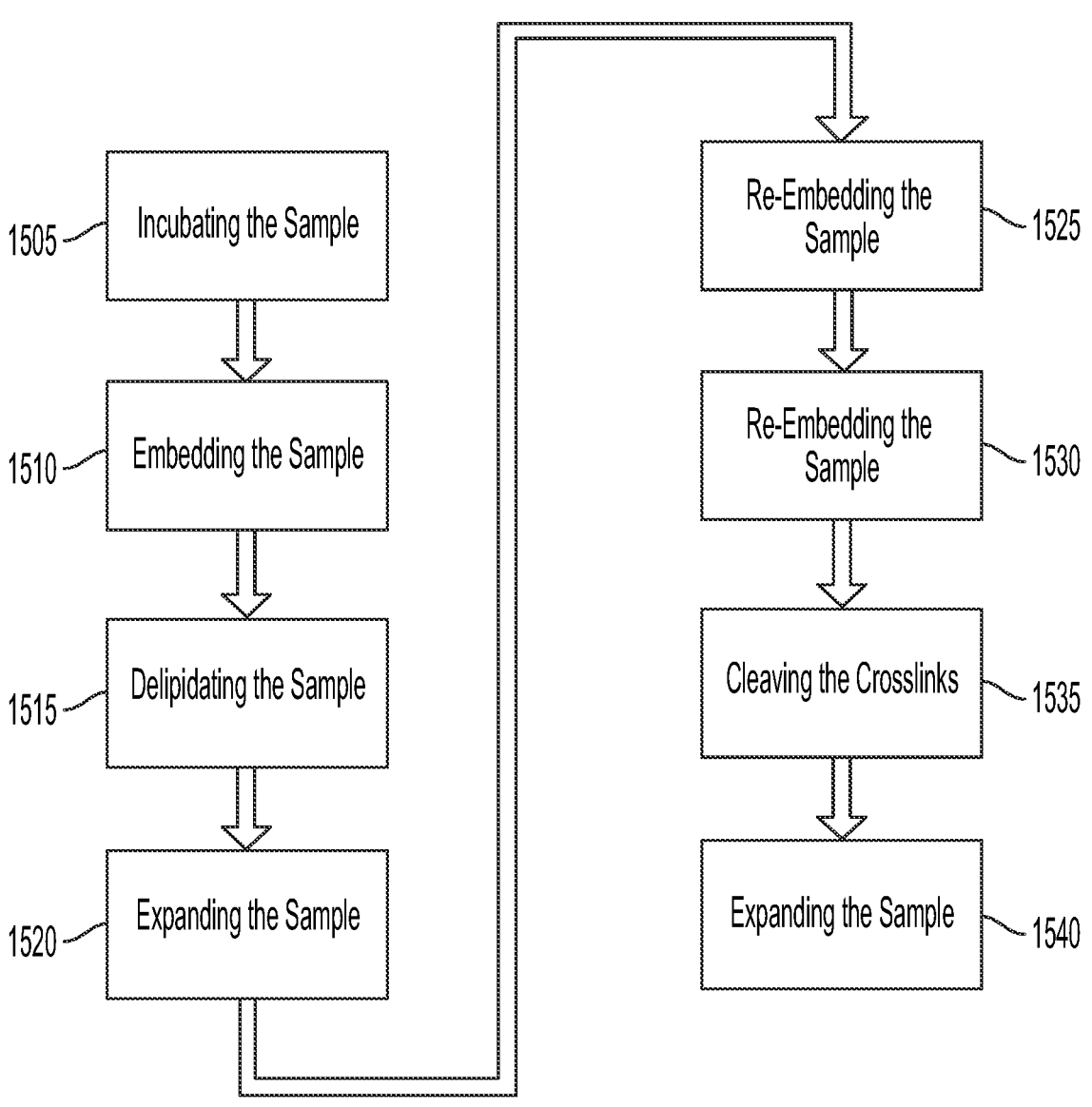

FIG. 15 depicts an example workflow process for preparing a biological sample for the purpose of identifying structural features of the sample, according to an embodiment of the claimed invention.

At Step 1505, a chemically-fixed sample can be incubated with a solution of formaldehyde and acrylamide to prevent protein-protein crosslinking while maximizing the formation of protein-acrylamide conjugates.

At Step 1510, the sample can be embedded in a swellable dense hydrogel crosslinked with cleavable crosslinkers. At Step 1515, the sample can be delipidated and denatured with surfactants and heat. At Step 1520, the sample can be expanded in water. At Step 1525, the sample can be re-embedded in a neutral hydrogel crosslinked with cleavable crosslinkers. At Step 1530, the sample can be re-embedded in a swellable dense hydrogel crosslinked with a crosslinker orthogonal to the crosslinkers in the first and second hydrogels.

At Step 1535, the first and second hydrogel crosslinkers can be cleaved. At Step 1540, the sample can be expanded in water.

Example Process Flow #3

Figure 16:
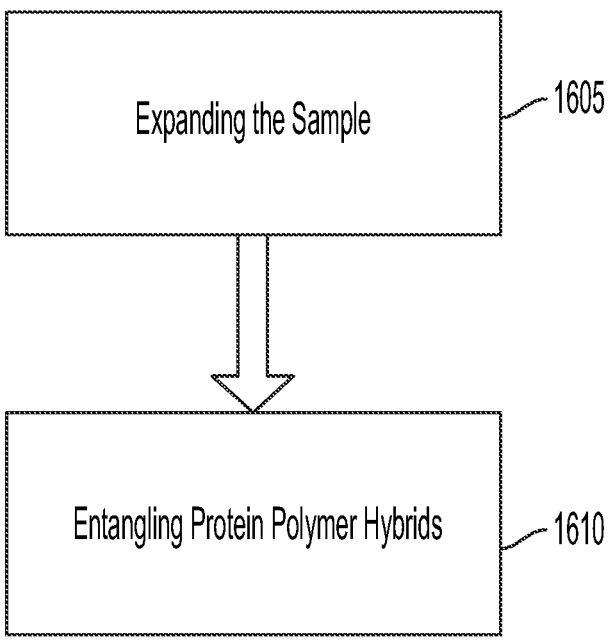

FIG. 16 depicts an example workflow process for preparing a biological sample for the purpose of identifying structural features of the sample, according to an embodiment of the claimed invention.

At Step 1605, the sample can be physically expanded by at least a factor of 2 in at least 1 dimension. The expansion can include embedding the sample into at least one polymer network. The polymer network can include polymer chains crosslinked with crosslinkers. A liquid, such as deionized water, can be introduced to the polymer network, which can increase in size linearly. The embedded sample can also increase in size with the introduction of the liquid.

At Step 1610, protein polymer hybrids of another polymer network can be entangled to retain a majority of the proteome of the sample. The embedded sample can be re-embedded into a second polymer network. The second polymer network can include polymer chains that are crosslinked with other crosslinkers. In some cases, these crosslinkers can be orthogonal to the crosslinkers of the first polymer network.

The re-embedding of the sample into the second polymer network can entangle polymer chains of the first polymer network with polymer chains from the second polymer network. This entanglement can preserve or retain the proteome of the sample during expansion.

After re-embedding, a liquid can be introduced to the second polymer network, causing the second polymer network to swell. The expanded sampled can thus be further expanded, such as to a factor of $4^2$. Additionally, as the entanglement of the polymer networks preserved the proteome of the sample, the expanded sample does not significantly degrade during expansion.

Example Process Flow #4

Figure 17:
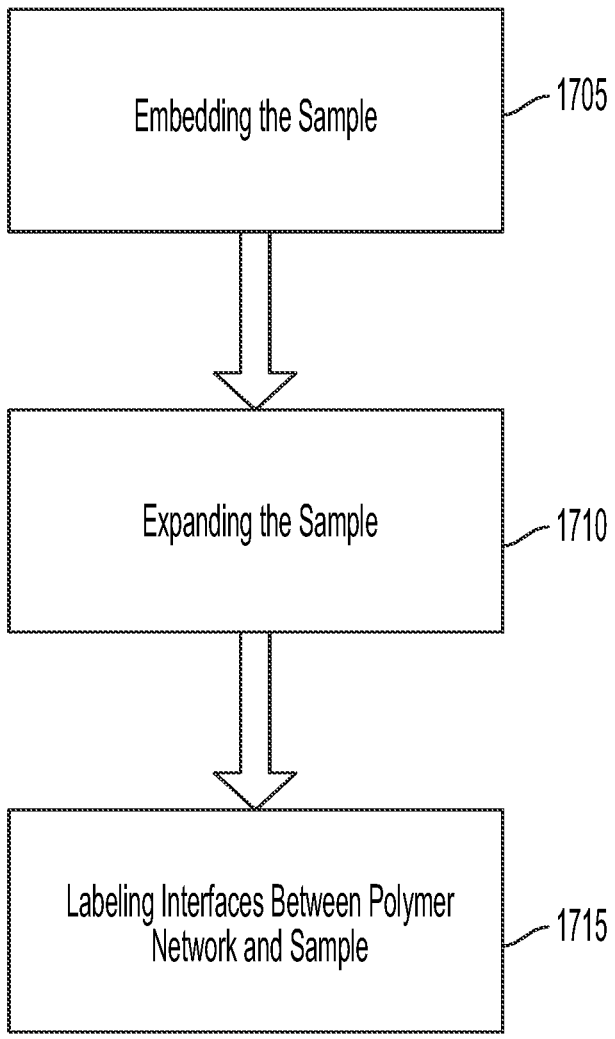

FIG. 17 depicts an example workflow process for preparing a biological sample for the purpose of identifying structural features of the sample, according to an embodiment of the claimed invention.

At Step 1705, the sample can be embedded in a polymer network. The polymer network can include polymer chains crosslinked with crosslinkers.

At Step 1710, the polymer network can be physically expanded by at least a factor of 2 in at least 1 dimension. A liquid, such as deionized water, can be introduced to the polymer network, which can increase in size linearly. The embedded sample can also increase in size with the introduction of the liquid.

At Step 1715, the interfaces between the polymer network and the sample can be labeled with a reagent in order to create an expanded representation of structural features of the embedded sample. The reagent can be a component-specific reagent, a global reagent, or a combination thereof. As the different components of the expanded sample are spatially distanced from each other, the components are identifiable through the labeling.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method for preparing a biological sample, the method comprising:
   (a) fixing the sample with a fixative molecule;
   (b) embedding the biological sample in a swellable polymer containing fixative-modifying monomers;
   (c) disrupting chemical bonds within the biological sample;
   (d) expanding the sample in a solvent to generate an expanded sample; and
   (e) labeling the expanded sample with at least one bulk label and expanding the sample in another solvent, wherein the at least one bulk label labels multiple portions of non-identical molecules in the biological sample.

2. The method of claim 1, wherein fixative molecule comprises an amine-reactive fixative and the swellable polymer contains at least one amine-functionalized monomer.

3. The method of claim 1, wherein fixative molecule comprises a thiol-cleavable fixative and the swellable polymer contains at least one thiol-reactive monomer.

4. The method of claim 2, wherein the amine-reactive fixative comprises:
   A) a heat-reversible fixative, a base-cleavable fixative, or a combination thereof; or B) formaldehyde (FA), dimethyl suberimidate (DMS), dimethyl pimelimidate (DMP) dimethyl adipimidate (DMA), or a combination thereof.

5. The method of claim 2, wherein the at least one amine-functionalized monomer is acrylamide (AAm), allylamine (ADP), 2-vinylpyridine (2-VP), N-(2-Amino-ethyl) acrylamide hydrochloride, 2-aminoethyl methacrylate hydrochloride, or a combination thereof.

6. The method of claim 3, wherein the thiol-cleavable fixative is dithiobis (succinimidyl propionate) (DSP), 1,5-difluoro-2,4-dinitrobenzene (DFDNB), succinimidyl 3-(2-pyridyldithio) propionate (SPDP), succinimidyl 6-(3(2-pyridyldithio) propionamido) hexanoate (LC-SPDP), or 4-succinimidyloxycarbonyl-alpha-methyl-α(2-pyridyldithio) toluene (SMPT), or a combination thereof.

7. The method of claim 3, wherein the at least one thiol-reactive monomer is pyridyl disulfide ethyl methacrylate (PDSMA), pyridyl disulfide ethyl acrylamide (PDSAAm), or a combination thereof.

8. The method of claim 1, wherein the swellable hydrogel is crosslinked with piperazine diacrylamide with concentrations between 0.001% and 0.2%.

9. The method of claim 1, wherein prior to step (b) and/or step (c), the sample is denatured with
   (A) anionic detergents or chaotropic reagents, or
   (B) sodium dodecyl sulfate, urea, guanidine hydrochloride, or a combination thereof.

10. A method for preparing a biological sample, the method comprising:
    (a) fixing the sample;
    (b) embedding the sample in a polymer network containing fixative-modifying monomers;
    (c) disrupting chemical bonds within the sample;
    (d) modifying the polymer network by inserting additional molecules into the polymer network to increase its size; and
    (e) labeling the sample with at least one bulk label and expanding the sample in a solvent.

11. The method of claim 10, wherein the polymer network of step (b) is swellable.

12. The method of claim 10, wherein:
    the polymer network of step (b) comprises at least one insertion site;
    the inserting of the additional molecules in step (d) comprises:
    in situ polymerization of monomer inserts at the insertion site of the polymer network to form an in situ-formed polymer; or
    insertion of a bifunctional linear polymer at the insertion site of the polymer network to form an inserted bifunctional linear polymer; and
    the in situ-formed polymer or inserted bifunctional linear polymer contains at least one additional monomer or polymer insertion site, the additional monomer or polymer insertion site permitting insertion of additional in situ-formed polymer or bifunctional linear polymer through at least one successive round of in situ polymerization or bifunctional linear polymer insertion, or a combination thereof.

13. The method of claim 12, wherein the in situ-formed or inserted bifunctional linear polymer chains are swellable.

14. The method of claim 10, wherein step (d) occurs before step (c) or after step (e).

15. The method of claim 12, wherein the in situ polymerization comprises reversible addition-fragmentation chain-transfer (RAFT) polymerization of hydrophilic monomers.

16. The method of claim 15, wherein the polymer chains are grown by RAFT photopolymerization of a thiocarbonate-crosslinked polymer network in the presence of hydrophilic monomers, a photocatalyst, and a light source.

17. The method of claim 10, wherein the polymer network of step (b) is synthesized with cleavable crosslinkers.

18. The method of claim 12, wherein the at least one insertion site comprises a monomer insertion site, crosslinker insertion site, polymer insertion site, or a combination thereof.

19. The method of claim 18, wherein the insertion site is a polymerizable molecule enabling in situ polymerization of monomer inserts.

20. The method of claim 18, wherein the insertion site is conjugated to a bifunctional linear polymer.

* * * * *